(12) United States Patent
Fink et al.

(10) Patent No.: US 7,417,040 B2
(45) Date of Patent: *Aug. 26, 2008

(54) FUSED TRICYCLIC COMPOUNDS AS INHIBITORS OF 17β-HYDROXYSTEROID DEHYDROGENASE 3

(75) Inventors: Brian E. Fink, West Windsor, NJ (US); Ashvinikumar V. Gavai, Princeton Junction, NJ (US); Gregory D. Vite, Titusville, NJ (US); Wen-Ching Han, Newtown, PA (US); Raj N. Misra, Hopewell, NJ (US); Hai-Yun Xiao, Belle Mead, NJ (US); Derek J. Norris, Pennington, NJ (US); John S. Tokarski, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 318 days.

This patent is subject to a terminal disclaimer.

(21) Appl. No.: 11/066,373

(22) Filed: Feb. 25, 2005

(65) Prior Publication Data

US 2005/0250753 A1 Nov. 10, 2005

Related U.S. Application Data

(60) Provisional application No. 60/548,851, filed on Mar. 1, 2004.

(51) Int. Cl.
*A61K 31/33* (2006.01)
*C07D 225/04* (2006.01)
*C07D 267/22* (2006.01)
*C07D 281/18* (2006.01)
*C07D 291/00* (2006.01)
*C07D 337/16* (2006.01)
*A01N 43/00* (2006.01)

(52) U.S. Cl. ...................... 514/183; 540/466
(58) Field of Classification Search .................. None
See application file for complete search history.

(56) References Cited

U.S. PATENT DOCUMENTS

| | | | |
|---|---|---|---|
| 3,336,293 A | 8/1967 | Cusic et al. | |
| 3,336,303 A | 8/1967 | Coyne et al. | |
| 3,367,930 A | 2/1968 | Schmutz et al. | |
| 3,676,432 A | 7/1972 | Helsley | |
| 3,714,148 A | 1/1973 | Okamoto et al. | |
| 4,209,523 A | 6/1980 | Lafon | |
| 4,888,335 A | 12/1989 | Mohrbacher et al. | |
| 5,112,867 A | 5/1992 | Kinoshita et al. | |
| 5,171,745 A | 12/1992 | De Noble et al. | |
| 5,296,493 A | 3/1994 | Moldt et al. | |
| 5,348,965 A | 9/1994 | Andersen et al. | |
| 5,514,505 A | 5/1996 | Limburg et al. | |
| 5,598,551 A | 1/1997 | Barajas et al. | |
| 5,599,815 A | 2/1997 | Fukuda et al. | |
| 5,998,613 A | 12/1999 | Falch et al. | |
| 6,025,355 A | 2/2000 | Reddy et al. | |
| 6,114,381 A | 9/2000 | Pitzele et al. | |
| 6,235,730 B1 | 5/2001 | Sato et al. | |
| 6,281,212 B1 | 8/2001 | Schwender et al. | |
| 6,323,206 B1 | 11/2001 | Schwender et al. | |
| 6,353,018 B1 | 3/2002 | Jeppesen et al. | |
| 6,534,496 B1 * | 3/2003 | Ishihara et al. | ......... 514/212.07 |
| 6,543,496 B2 | 4/2003 | Woodruff | |
| 6,960,474 B2 | 11/2005 | Salvati et al. | |
| 2004/0176324 A1 | 9/2004 | Salvati et al. | |
| 2005/0191707 A1 | 9/2005 | Lorenzi et al. | |
| 2005/0192310 A1 * | 9/2005 | Gavai et al. | ................. 514/291 |

FOREIGN PATENT DOCUMENTS

| | | |
|---|---|---|
| JP | 06234753 | 8/1994 |
| JP | 07033744 | 2/1995 |
| JP | 2001-247573 | 9/2001 |
| WO | WO 9212133 | 7/1992 |
| WO | WO 9315052 | 8/1993 |
| WO | WO 9315073 | 8/1993 |
| WO | WO 9322302 | 11/1993 |
| WO | WO 9413291 | 6/1994 |
| WO | WO 9509634 | 4/1995 |
| WO | WO 9509858 | 4/1995 |
| WO | WO 9518615 | 7/1995 |
| WO | WO 9605185 | 2/1996 |

(Continued)

OTHER PUBLICATIONS

Fink et al. Bioorganic and Medicinal Chemistry Letters, 2006, 16, 1532-1536.*

(Continued)

*Primary Examiner*—James Wilson
*Assistant Examiner*—Noble Jarrell
(74) *Attorney, Agent, or Firm*—Gary D. Greenblatt

(57) ABSTRACT

Disclosed are fused tricyclic compounds of the following formula I,

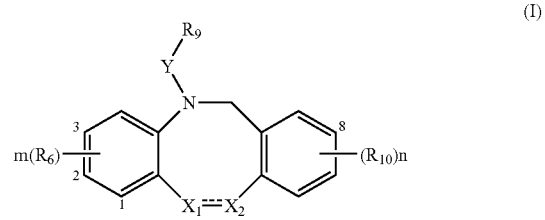

or an enantiomer, diastereomer, tautomer or pharmaceutically acceptable salt thereof. The disclosed compounds are useful as inhibitors of 17β-hydroxysteriod dehydrogenase 3 (17βHSD3). Also disclosed are methods of using such compounds in the treatment of hormone sensitive diseases such as prostate cancer and pharmaceutical compositions comprising such compounds.

13 Claims, No Drawings

FOREIGN PATENT DOCUMENTS

| | | |
|---|---|---|
| WO | WO 9631500 | 10/1996 |
| WO | WO 9722342 | 6/1997 |
| WO | WO 9730054 | 8/1997 |
| WO | WO 9909991 | 3/1999 |
| WO | WO 9920599 | 4/1999 |
| WO | WO 9946279 | 9/1999 |
| WO | WO 0018721 | 4/2000 |
| WO | WO 0020398 | 4/2000 |
| WO | WO 0032193 | 6/2000 |
| WO | WO 0072833 | 12/2000 |
| WO | WO 0200653 | 1/2002 |
| WO | WO 03022835 | 3/2003 |
| WO | WO 2005/094816 | * 10/2005 |

OTHER PUBLICATIONS

Sax et al. Hawley's Condensed Chemical Dictionary, Eleventh Edition, 1987, pp. 1079-1080.*
Patani and LaVoie. Chemical Reviews, 1996, 96, 3147-3176.*
Giuseppe et al. Expert Opinion on Therapeutic Patents, 1997, 7(4), 307-323.*
Vippagunta et a. Advanced Drug Delivery Reviews, 2001, 48, 3-26.*
Kametani et al. Journal of the Chemical Society (C), 1971, pp. 1800-1803.*
Gheiler, E. L., et al., Current concepts in androgen deprivation therapy—is there a "best" endocrine treatment?, World J. Urology., vol. 18, pp. 190-193, (2000).
Inano, H., et al., "Testicular 17β-Hydroxysteroid Dehydrogenase: Molecular Properties and Reaction Mechanism", Steroids, vol. 48(1-2), pp. 1-26, (1986).
Jalsovszky, I., et al., "The extent of transannular sulfur-nitrogen interactions in stereoisomeric 1,5-thiazocine derivatives: a semiempirical MO study", Journal of Molecular Structure, vol. 365, pp. 93-102, (1996).
Jalsovszky, I., et al., "Transannular sulfur-nitrogen interactions in stereoisomeric 1,5-thiazocine derivatives: An ab initio MO study", Journal of Molecular Structure, vol. 418, pp. 155-163, (1997).
Kisel, V. M., "Synthesis and Properties of Novel Dibenz[b,f]Azocines", Translated from Khimiya Geterotsiklicheskikh Soedinenii, No. 1, pp. 92-95, (1991).
Kuti, M., et al., "Transannular sulfur-nitrogen interaction in 1,5-thiazocine derivatives: an X-ray study", Journal of Molecular Structure, vol. 382, pp. 1-11, (1996).
Labrie, F., "At the Cutting Edge Intracrinology", Molecular and Cellular Endocrinology, vol. 78, pp. C113-C118, (1991).
Labrie, F. et al. "History of LHRH agonist and combination therapy in prostate cancer", Endocrine-Related Cancer, vol. 3, pp. 243-278, (1996).
Liu, X., et al., "Androgens Regulate Proliferation of Human Prostate Cancer Cells in Culture by Increasing Transforming Growth Factor-α Receptor", Journal of Clinical Endocrinology and Metabolism, vol. 77(6), pp. 1472-1478.
Luu-The, V., "Characteristics of Human Types 1,2 and 3 17β-Hydroxysteroid Dehydrogenase Activities: Oxidation/Reduction and Inhibition", J. Steroid Biochem. Molec. Biol., vol. 55(5/6), pp. 581-587, (1995).
Maltais, R., et al., "Synthesis and Optimization of a New Family of Type 3 17β-Hydroxysteroid Dehydrogenase Inhibitors by Parallel Liquid-Phase Chemistry", J. Med. Chem., vol. 45, pp. 640-653, (2002).
Pittaway, D. E., "Inhibition of Testosterone Synthesis in the Canine Testis in Vitro", Contraception, vol. 27(4), pp. 431-436, (1983).
Simard, J., et al., "Comparison of in Vitro Effects of the Pure Antiandrogens OH-Flutamide, Casodex, and Nilutamide on Androgen-Sensitive Parameters", Urology, vol. 49(4), pp. 580-589, (1997).
Van Weerden, W.M., "Effects of Low Testosterone Levels and of Adrenal Androgens on Growth of Prostate Tumor Models in Nude Mice", J. Steroid Biochem. Molec. Biol., vol. 6, pp. 903-907, (1990).
Kambe, et al., "Intramolecular 1,3-Dipolar Cycloaddition Strategy for Enantioselective Synthesis of FR-900482 Analogues", Organic Letters, vol. 3(16), pp. 2575-2578, (2001).
Cooper et al., Cyclic Amidines. Part IV. 5:6:22:23-Tetrahydro-5:11-endomethylenephenhomazines and Troger's Base, Journal of the Chemical Society, Abstracts, pp. 991-994, (1955).
PCT International Search Report (PCT/US05/06548) mailed Dec. 7, 2005.
PCT International Search Report (PCT/US05/06549) mailed Dec. 13, 2005.
U.S. Appl. No. 11/255,484, filed Oct. 21, 2005, Bristol Myers Squibb Co.

* cited by examiner

FUSED TRICYCLIC COMPOUNDS AS INHIBITORS OF 17β-HYDROXYSTEROID DEHYDROGENASE 3

RELATED APPLICATION

This application claims priority benefit under Title 35 § 119(e) of U.S. provisional Application No. 60/548,851, filed on Mar. 1, 2004, the contents of which are herein incorporated by reference.

FIELD OF THE INVENTION

The present invention relates to fused tricyclic compounds, to methods of using such compounds in the treatment of hormone sensitive diseases such as prostate cancer, and to pharmaceutical compositions containing such compounds.

BACKGROUND OF THE INVENTION

17β-hydroxysteroid dehydrogenase 3 (17β-HSD3) is an essential enzyme in the biosynthesis of testosterone. It catalyzes the reduction of androstenedione, a weakly active androgen produced by the adrenal glands, to testosterone. Inano et al., *Steroids*, 48, 1-26, (1986) and Luu-The et al., *J. Steroid Biochem. Mol. Biol.*, 55, 581-587 (1995). 17β-HSD3 is expressed predominately in the adult testes and to a lesser extent in seminal vesicles and prostate tissue, an expression pattern consistent with an enzyme involved in both gonadal and peripheral target tissue androgen biosynthesis. 17β-HSD3 is responsible for the synthesis of about 60% of all active androgens in men. Labrie, *Mol. Cell. Endocrinol.* 78, C113-C118 (1991). The development and progression of hormone sensitive diseases, e.g., prostate cancer, is stimulated by androgens such as testosterone. Inhibition of 17β-HSD3 therefore provides a novel means to disrupt testosterone biosynthesis for the treatment of androgen-associated diseases. Van Weerden et al., *J. Steroid Biochem. Mol. Biol.*, 20, 903-907 (1990) and Liu et al., *J. Clin. Endocrinol.*, 77, 1472-1478 (1993).

Current pharmacological treatments to prevent androgen action in androgen-associated diseases such as prostate cancer are centered on the combined use of luteinizing hormone releasing hormone (LHRH) analogues with androgen receptor antagonists ("anti-androgens"). Labrie et al., *Endocr.-Relat. Cancer*, 3, 243-278 (1996); Gheiler et al., *World J. Urol.*, 18, 190-193 (2000); and Simard, et al., *J. Urol.*, 49, 580-586 (1997). LHRH analogues interfere with central nervous system feedback mechanisms to suppress testosterone biosynthesis in the testes to produce chemical castration. However, it is estimated that up to 50% of testosterone levels remain within prostate tissue following chemical or surgical castration indicating the existence of alternate routes of testosterone biosynthesis independent of the testes. Anti-androgens are used to block the action of this remaining testosterone in prostate cancer cells by antagonizing hormone function at the level of receptor binding. Although the combined use of LHRH analogues with anti-androgens has shown success in the management of prostate cancer, these responses are largely restricted to advanced metastatic disease. Further, patients receiving these treatments ultimately become refractory and progress to a more aggressive, hormone-independent state for which there is no effective therapy.

Inhibitors of 17β-HSD3 have been described in the art. See, e.g., Pittaway, *Contraception*, 27, 431 (1983); Labrie et al., WO99/46279; Maltais et al., *J. Med. Chem.*, 45, 640-653 (2002); and Guzi et al., WO03/022835. There remains a need for potent, selective inhibitors of 17β-HSD3 with improved pharmacological properties, physical properties and side effect profiles.

The compounds of the present invention are inhibitors of 17β-HSD3, and therefore have therapeutic use as anti-cancer agents, as well as other therapeutic agents, for example, as anti-fertility agents as described following.

SUMMARY OF THE INVENTION

The present invention provides a fused tricyclic compound of the following formula I, or an enantiomer, diastereomer, tautomer or pharmaceutically acceptable salt or solvate thereof, which compounds are especially useful as inhibitors of 17β-hydroxysteroid dehydrogenase 3 (17β-HSD3):

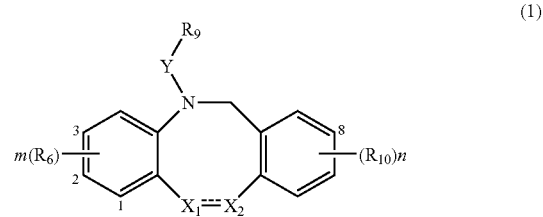

(1)

As used in formula I, and throughout the specification, the symbols have the following meanings unless otherwise indicated, and are, for each occurrence, independently selected:

Y is —C(=O)—, or —S(=O)$_2$—;

X$_1$=X$_2$ is —CR$_1$=CR$_3$—, —CR$_1$R$_2$—CR$_3$R$_4$—, —C(=O)—CR$_3$R$_4$—, —S—CR$_3$R$_4$—, —S(=O)$_2$—CR$_3$R$_4$—, —O—CR$_3$R$_4$—, —NR$_5$—CR$_3$R$_4$—, —CR$_1$R$_2$—S—, —CR$_1$R$_2$—S(=O)—, —CR$_1$R$_2$—S(=O)$_2$—, —CR$_1$R$_2$—C(=O)—, —CR$_1$R$_2$—O—, or CR$_1$R$_2$—NR$_5$—;

R$_2$, R$_4$, R$_6$ and R$_{10}$ are each independently hydrogen, halogen, cyano, nitro, alkyl or substituted alkyl (including CF$_3$), alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, wherein: R$_2$ and R$_4$ together may optionally form a 3-7 membered optionally substituted carbocyclic ring or 3-7 membered optionally substituted heterocyclic ring;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle;

R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $C(\!=\!O)OR_e$, $C(\!=\!O)R_a$, $NR_bR_c$, $NR_bC(\!=\!O)R_a$, $NR_bC(\!=\!O)OR_e$, $C(\!=\!O)NR_bR_c$, $OC(\!=\!O)R_a$, or $OC(\!=\!O)NR_bR_c$, wherein $R_1$ and $R_3$ together may optionally form a 3-7 membered optionally substituted carbocyclic ring or 3-7 membered optionally substituted heterocyclic ring;

$R_5$ is hydrogen, alkyl or substituted alkyl, cycloalkyl or substituted cycloalkyl, heterocycle or substituted heterocycle, aryl or substituted aryl, $OR_a$, $S(\!=\!O)_2R_e$, $C(\!=\!O)OR_e$, $C(\!=\!O)R_a$, or $C(\!=\!O)NR_bR_c$;

$R_9$ is H, alkyl or substituted alkyl (including $CF_3$), cycloalkyl or substituted cycloalkyl, cycloalkenyl or substituted cycloalkenyl, heterocycle or substituted heterocycle, aryl or substituted aryl, $OR_e$, or $NR_bR_c$;

m is 1-4; and n is 1-4;

provided that:

at least one of $R_6$ and $R_{10}$ is not H; and when $X_1\!=\!=\!X_{2X1}\!=\!=\!X_2$ is $-CH_2-CH_2-$, $R_9$ is not aryl or substituted aryl, or heteroaryl or substituted heteroaryl;

when $X_1\!=\!=\!X_2$ is $-S-CR_3R_4-$, each $R_{10}$ is H, and m=1, $R_6$ at the C-3 position is not H, methyl, halogen, OMe, $CF_3$, or $SCF_3$;

when $X_1\!=\!=\!X_2$ is $-NR_5-CR_3R_4-$, m=1, $R_6$ at the C-3 position is not H or halogen or $R_6$ at the C-2 position is not H, halogen, $CF_3$ or OMe; and when $X_1\!=\!=\!X_2$ is $-CR_1R_2-NR_5-$, m=1 and n=1, $R_6$ at the C-2 position is not H, halogen, methyl, or OMe and $R_{10}$ at the C-8 position is not H, halogen or methyl, wherein the C-2, C-3 and C-8 positions are as designated in formula I.

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $Cl_3$), cyano, nitro, cycloalkyl, alkenyl, cycloalkenyl, alkynyl, heterocycle, aryl, $OR_a$, $SR_a$, $S(\!=\!O)R_e$, $S(\!=\!O)_2R_e$, $P(\!=\!O)_2R_e$, $S(\!=\!O)_2OR_e$, $P(\!=\!O)_2OR_e$, $NR_bR_c$, $NR_bS(\!=\!O)_2R_e$, $NR_bP(\!=\!O)_2R_e$, $S(\!=\!O)_2NR_bR_c$, $P(\!=\!O)_2NR_bR_c$, $C(\!=\!O)OR_e$, $C(\!=\!O)R_a$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, $NR_dP(\!=\!O)_2NR_bR_c$, $NR_bC(\!=\!O)R_a$, or $NR_bP(\!=\!O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

Unless otherwise indicated, any heteroatom with unsatisfied valences is assumed to have hydrogen atoms sufficient to satisfy the valences.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art.

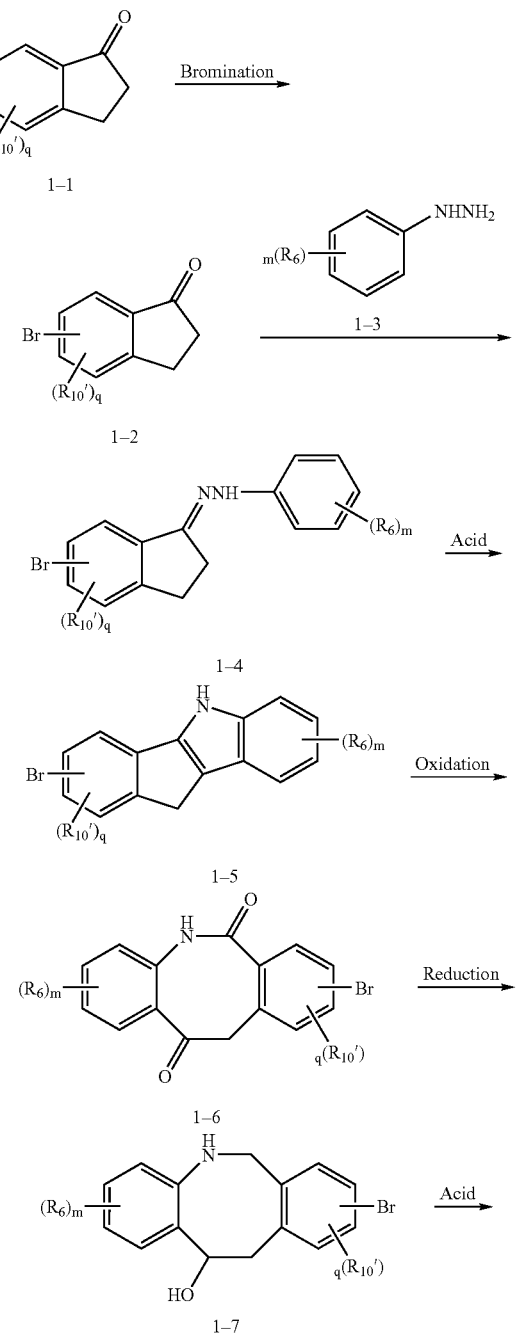

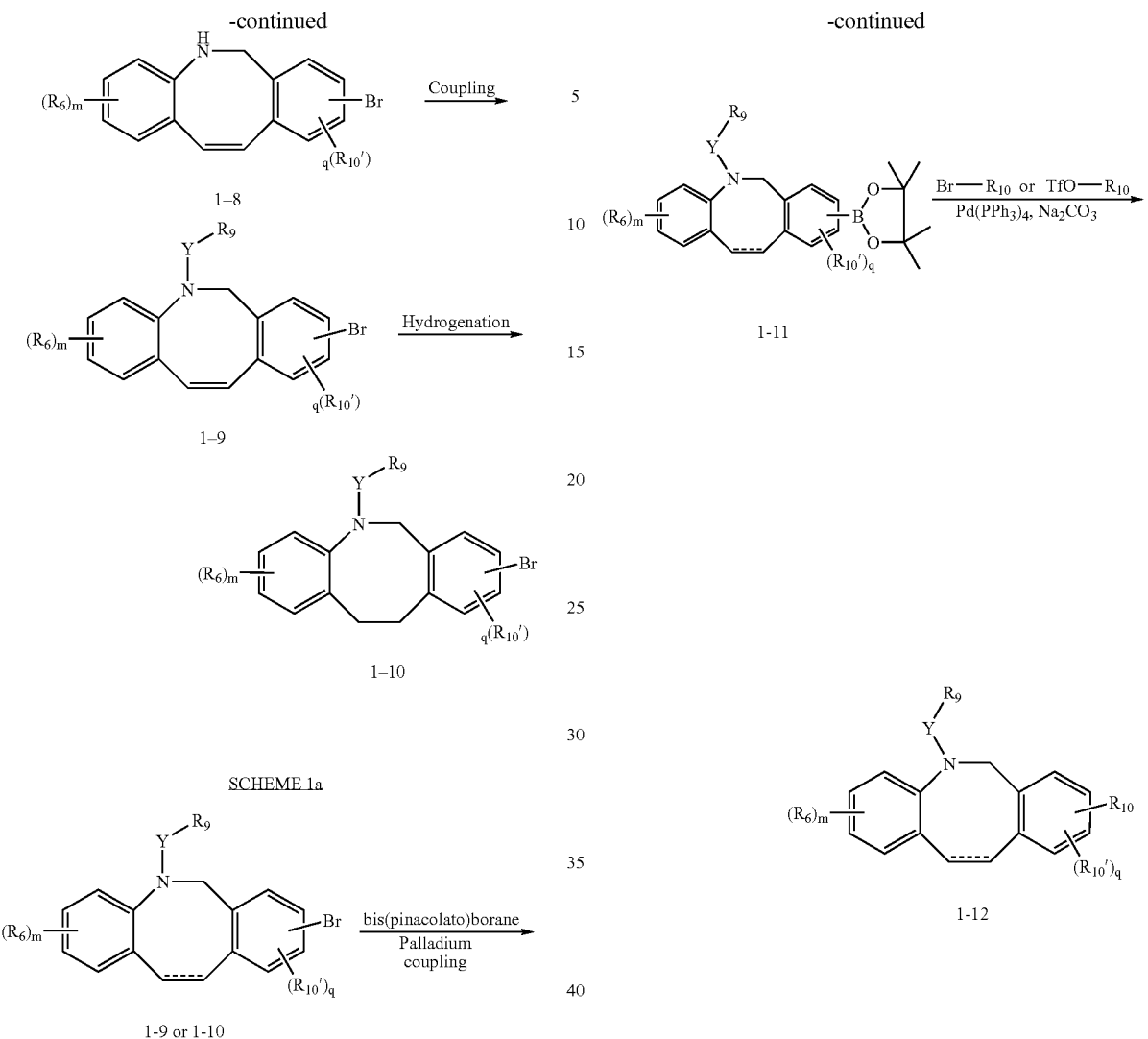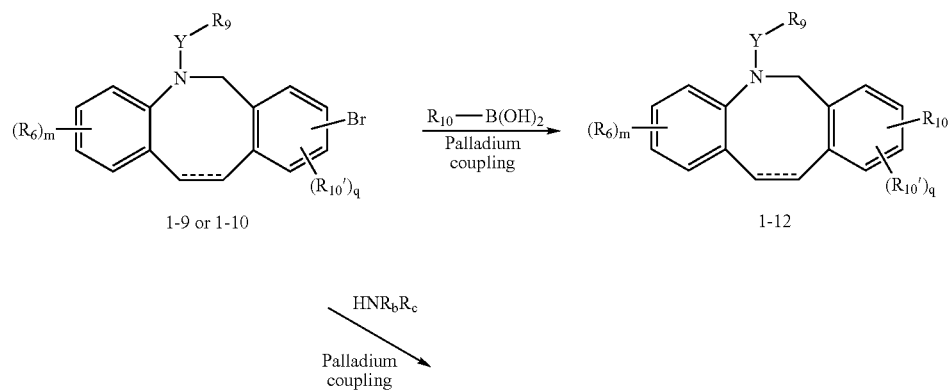

-continued

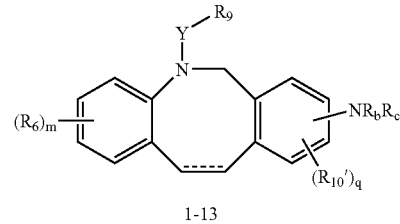

1-13

As illustrated in Schemes 1, 1a and 1b, compounds of formula I can be made from either 1-1 or 1-2. Y, $R_6$, $R_9$, $R_b$, $R_c$ and m are defined as above ($R_6$ is preferably not Br); $R_{10}'$ is hydrogen, halogen (preferably F and Cl), cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)F_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$, $R_b$, $R_c$, $R_d$ and $R_e$ are as defined above; q=1-3; and $R_{10}$ is alkyl or substituted alkyl, alkenyl or substituted alkenyl, alkynyl or substituted alkynyl, cycloalkyl or substituted cycloalkyl, heterocycle or substituted heterocycle, or aryl or substituted aryl. The definition contained herein also applies to Scheme 2 through Scheme 8, unless otherwise noticed.

Treatment of 1-2 with hydrazine 1-3 yields intermediate 1-4, which gives intermediate 1-5 upon treating with acid. Hydrazine 1-3 is either commercially available or can be prepared by one skilled in the art. Oxidation of 1-5 forms intermediate 1-6, which can be reduced to offer compound 1-7. Treatment of 1-7 with acid affords intermediate 1-8, which generates compound 1-9 through coupling with an acid, an acid chloride, an acid anhydride, or a chloroformate, wherein Y is —(C=O)—, or with a sulfonyl chloride or a phenyl isocyanatoformate, wherein Y is —S(=O)$_2$—. Compound 1-10 can be obtained from 1-9 by hydrogenation.

As shown in Scheme 1a, compound 1-12 can be synthesized from 1-9 or 1-10 by preparing intermediate 1-11 though a coupling with a borane reagent, such as bis(pinacolato) borane, followed by a palladium coupling with a bromo-subtitiued compound (Br—$R_{10}$) or a triflate substituted compound (TfO—$R_{10}$). The said Br—$R_{10}$ or TfO—$R_{10}$ is either commercially available or can be prepared by one skilled in the art. According to Scheme 1b, compound 1-12 can also be prepared by reacting 1-9 or 1-10 with $R_{10}$—B(OH)$_2$ using a palladium catalyst. $R_{10}$—B(OH)$_2$ is commercially available or readily prepared by one skilled in the art. Compound 1-13 can be obtained from 1-9 or 1-10 through a palladium coupling with $HNR_bR_c$. The alkene portion (—CH=CH—) of the center ring in compounds 1-12 and 1-13 can also be converted to alkane (—CH$_2$—CH$_2$—) through hydrogenation.

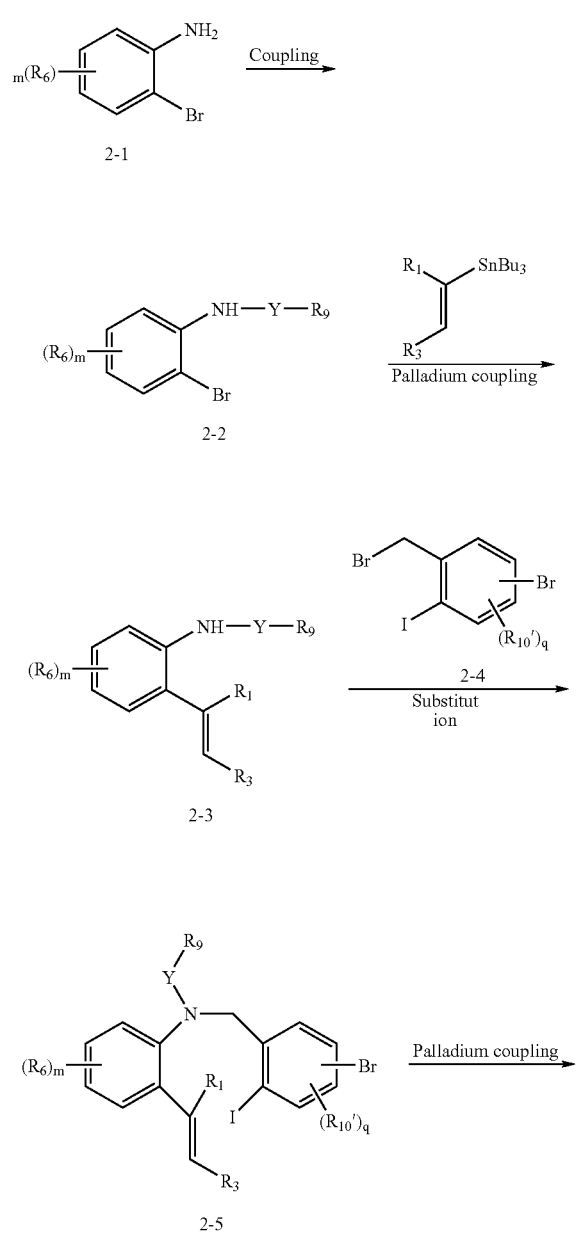

-continued
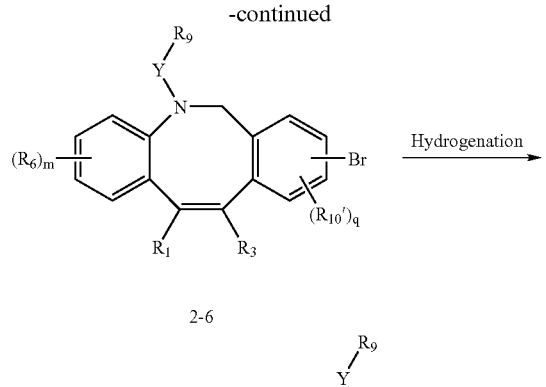
2-6
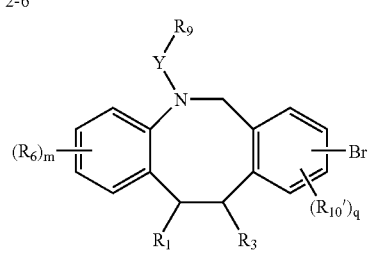
2-7
SCHEME 2a
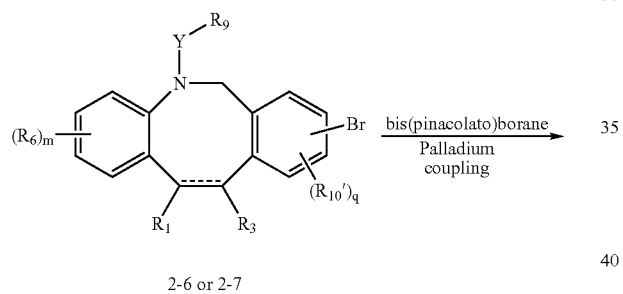
2-6 or 2-7
-continued
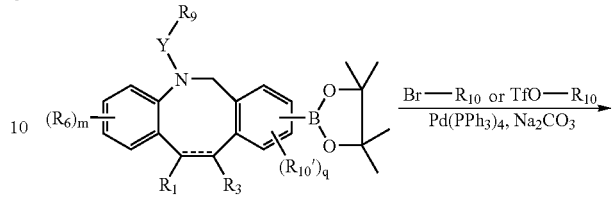
2-8
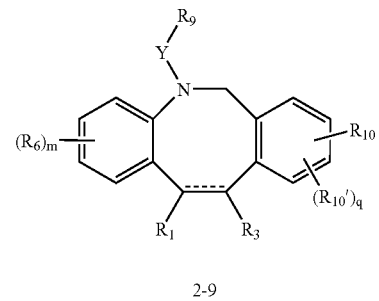
2-9
SCHEME 2b
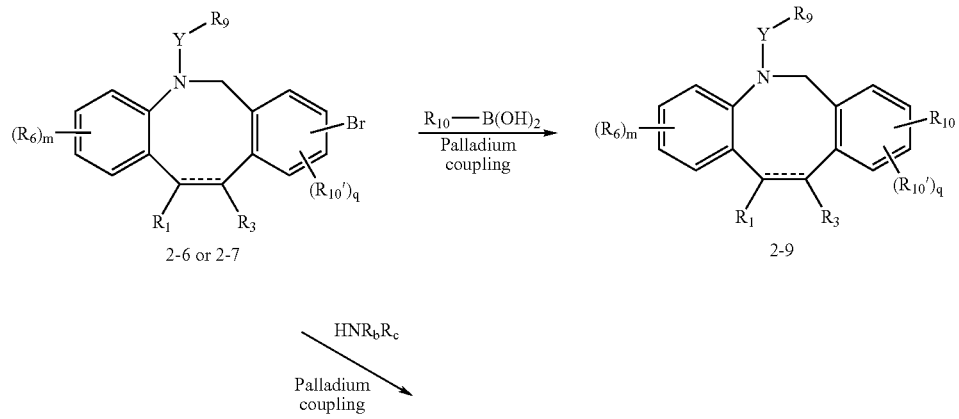

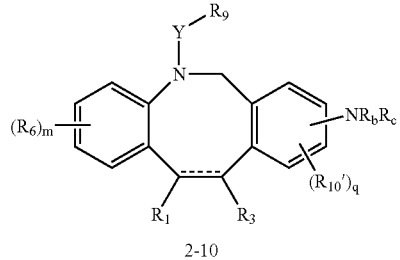

2-10

Alternatively, a compound of formula I can be prepared according to Scheme 2. Coupling of 2-1 with agents such as an acid, an acid chloride, an acid anhydride, a chloroformate, a sulfonyl chloride or a phenyl isocyanatoformate, affords intermediate 2-2, which can be subsequently converted to compound 2-3 via a tin coupling. A nuclear substitution of compound 2-4 with intermediate 2-3 gives intermediate 2-5, which can be transformed to compound 2-6 by a palladium coupling reaction. Hydrogenation of compound 2-6 yields compound 2-7. Additionally, compound 2-9 and 2-10 can be prepared according to Schemes 2a and 2b.

SCHEME 3

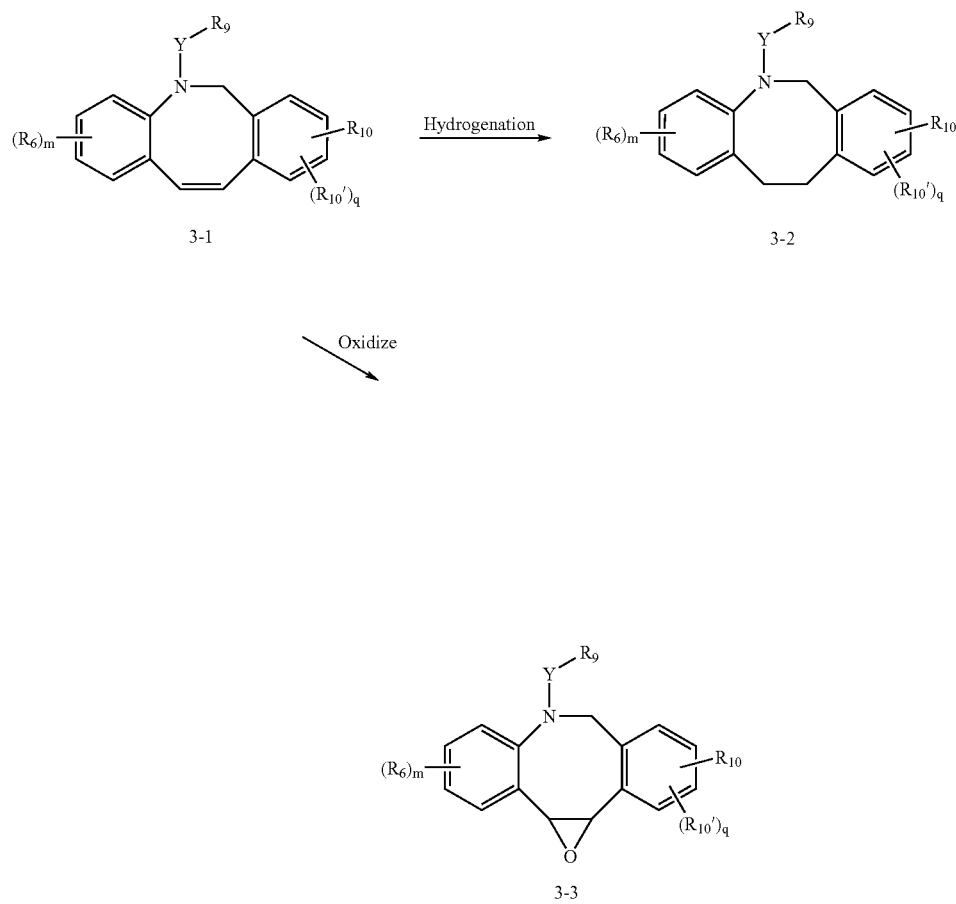

According to Scheme 3, compound 3-2 can also be prepared from 3-1 via hydrogenation. Compound 3-3 can be prepared from 3-1 through oxidation by using agents such as mCPBA.

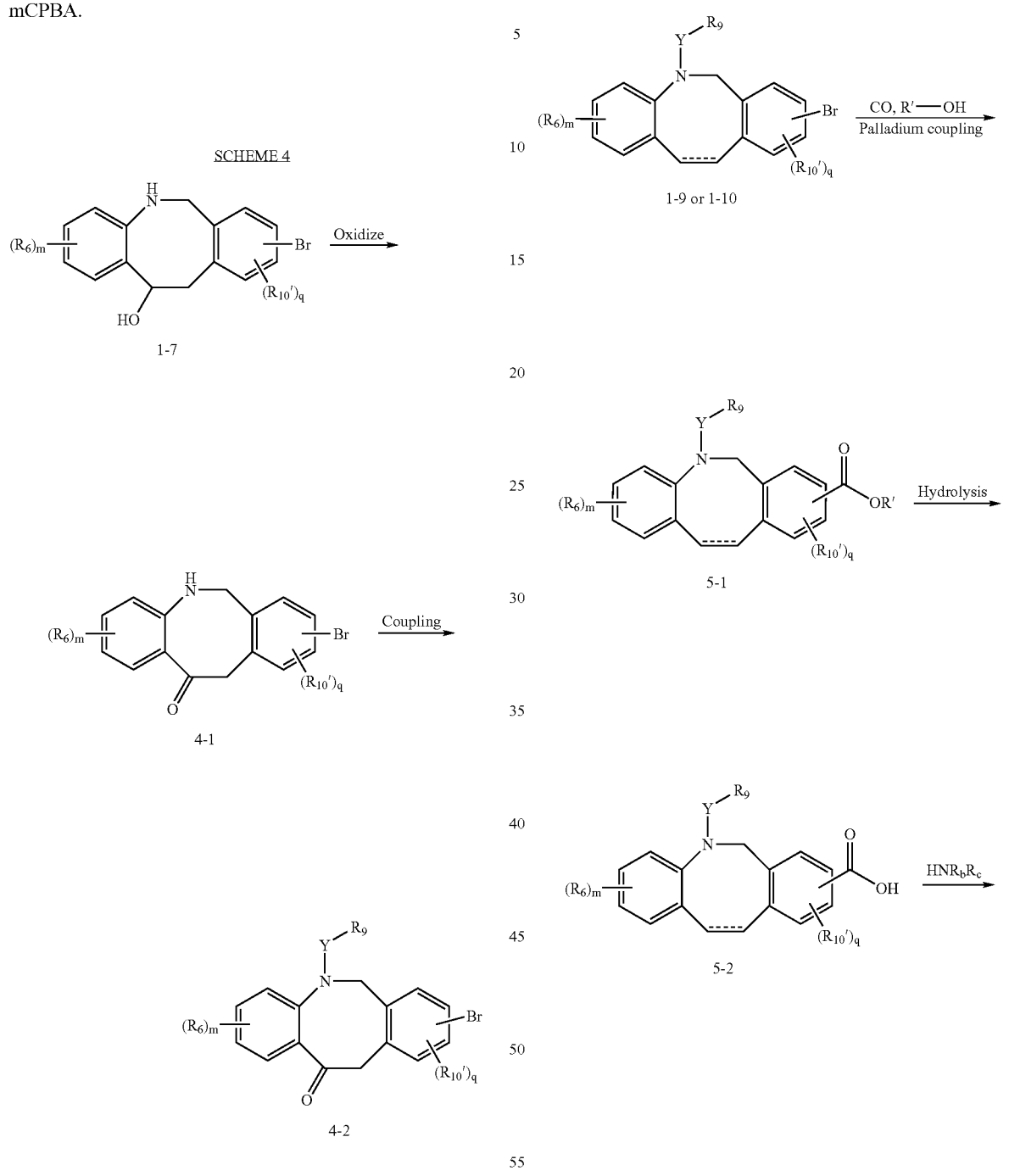

As shown in Scheme 4, a compound of formula I can also be prepared from 1-7. Oxidization of 1-7 gives intermediate 4-1, which can be converted to 4-2 via a coupling as described above. Additional analogues can be synthesized from 4-2 through palladium coupling as illustrated in Schemes 1a and 1b. Substituted esters 5-1 and amides 5-3 can be prepared according to Scheme 5, wherein $R_b$ and $R_c$ are defined as above and R' is $C_1$-$C_4$ alkyl such as methyl, ethyl, propyl, 2-methyl-propyl, or n-butyl.

SCHEME 6
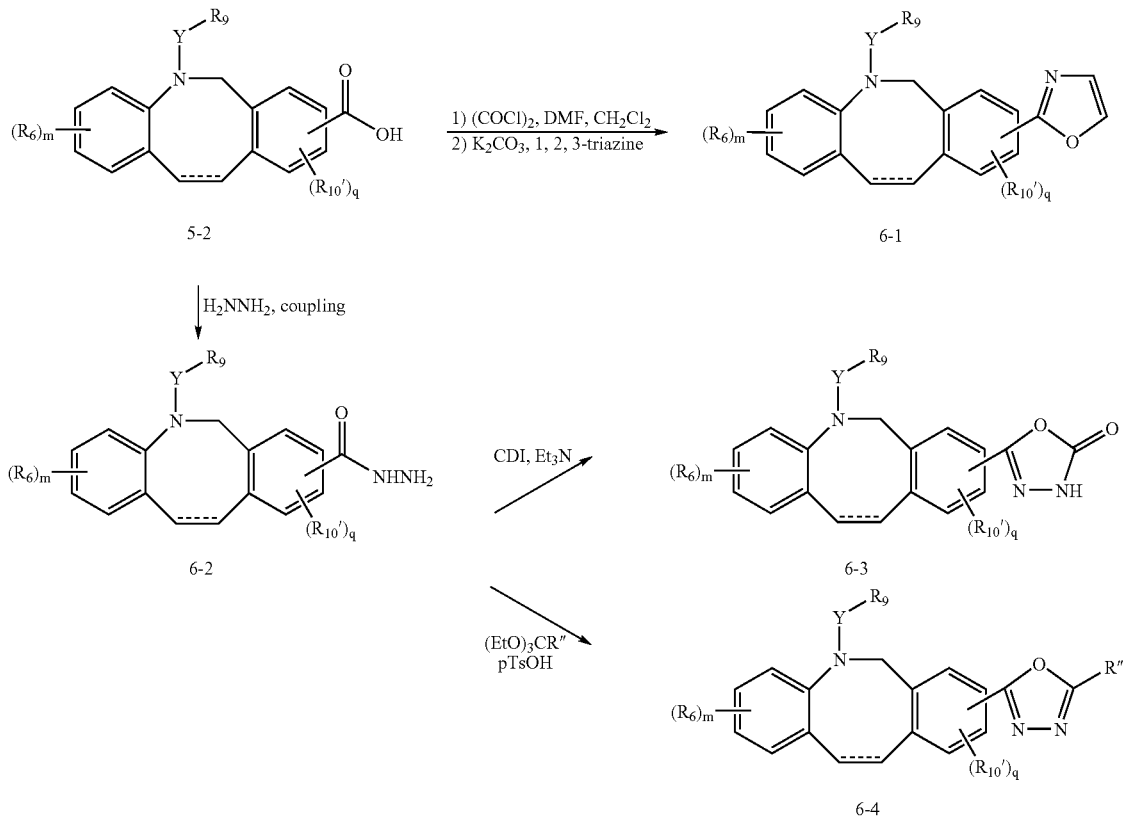
Substituted heterocycles, such as compounds 6-1, 6-3 and 6-4, wherein R″ is H, alkyl (such as methyl or ethyl) or substituted alkyl, or aryl (such as phenyl) or substituted aryl, can be synthesized according to Scheme 6.
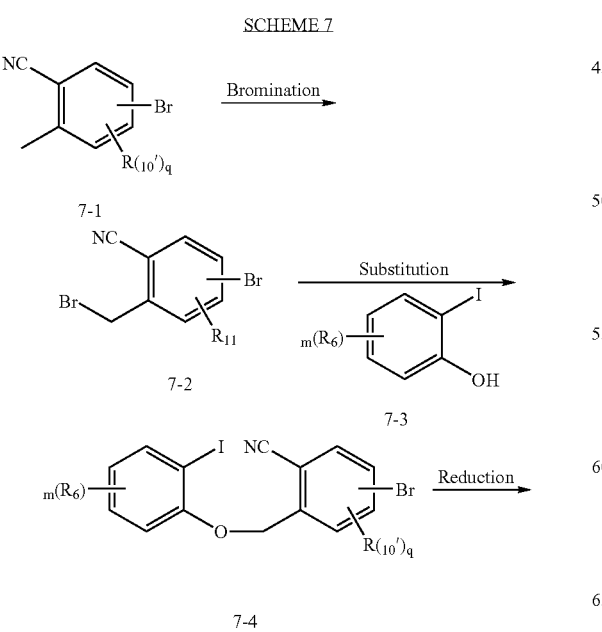
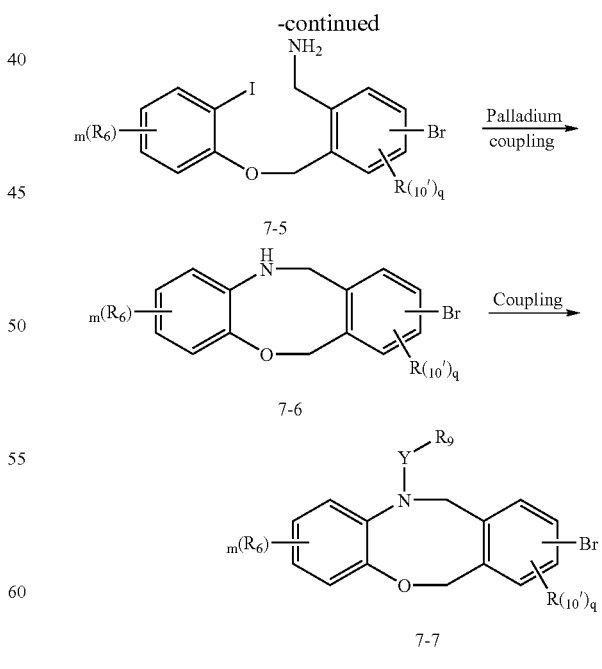
As shown in Scheme 7, compound of formula I wherein $X_1$══$X_2$ is —O—CH$_2$—, can be prepared from starting material 7-1. Bromination of compound 7-1 gives intermediate 7-2, which can be coupled with 7-3 to afford intermediate 7-4. Compound 7-3 is commercially available or can be readily made by one skilled in the art. Reduction of compound 7-4 gives intermediate 7-5, which can be cyclized via an internal palladium coupling. Compound 7-7 can be obtained via a coupling as described above. Additional analogues can be prepared from compound 7-7 as illustrated in Schemes 1a and 1b. Similarly, compound of formula I wherein $X_1$═$X_2$ is —$CH_2$—O—, can be prepared according to Scheme 8.

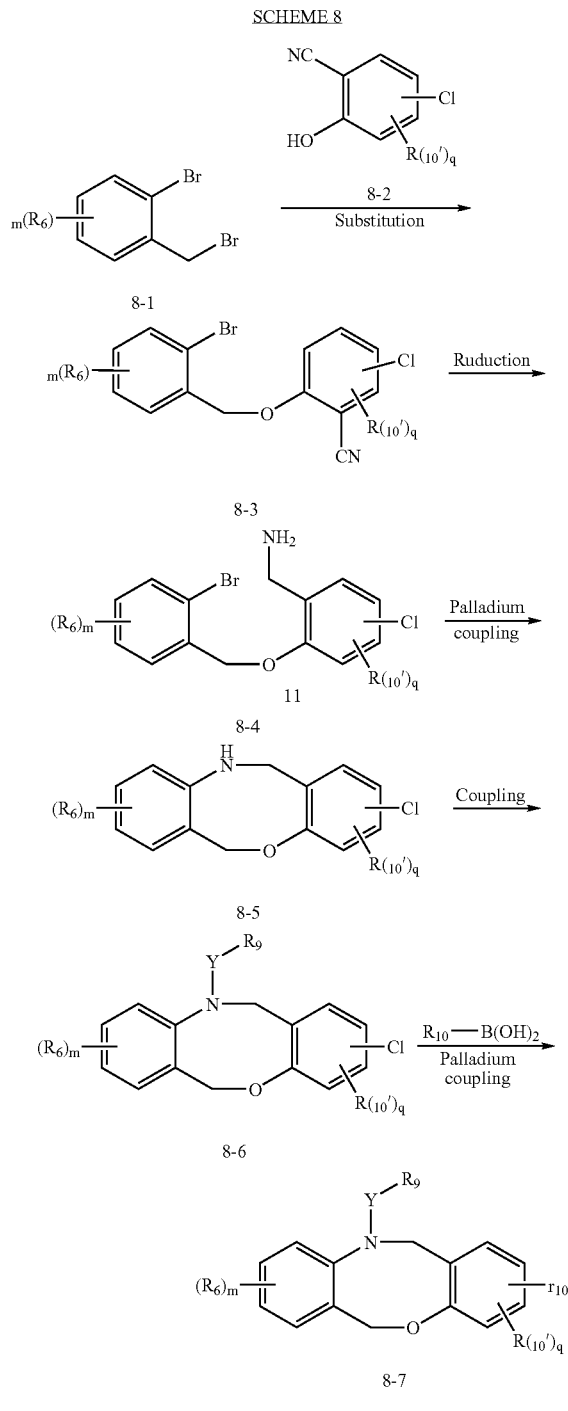

Preferred Compounds

A preferred subgenus of the compounds of the present invention includes compounds of the formula I or salts thereof wherein one or more, preferably all, of the following substituents are as defined below:

Y is —C(═O)—, or —S(═O)$_2$—;
$X_1$═$X_2$ is —$CR_1$═$CR_3$—, —$CR_1R_2$—$CR_3R_4$—, —C(═O)—$CR_3R_4$—, —S—$CR_3R_4$—, —S(═O)—$CR_3R_4$—, —S(═O)$_2$—$CR_3R_4$—, —O—$CR_3R_4$—, —$CR_1R_2$—S—, —$CR_1R_2$—S(═O)—, —$CR_1R_2$—S(═O)$_2$—, —$CR_1R_2$—C(═O)—, or —$CR_1R_2$—O—;

$R_2$, $R_4$, $R_6$ and $R_{10}$ are each independently hydrogen, cyano, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(═O)R_e$, $S(═O)_2R_e$, $S(═O)_2OR_e$, $NR_bR_c$, $NR_bS(═O)_2R_e$, $S(═O)_2NR_bR_c$, $C(═O)OR_e$, $C(═O)R_a$, $C(═O)NR_bR_c$, $OC(═O)R_a$, $OC(═O)NR_bR_c$, $NR_bC(═O)OR_e$, $NR_dC(═O)NR_bR_c$, $NR_dS(═O)_2NR_bR_c$, or $NR_bC(═O)R_a$,
wherein: $R_2$ and $R_4$ together may optionally form a 3-7 membered optionally substituted carbocyclic ring or 3-7 membered optionally substituted heterocyclic ring, and wherein $R_a$, $R_b$, $R_c$, $R_d$ and $R_e$ are as defined above;

$R_1$ and $R_3$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(═O)R_e$, $S(═O)_2R_e$, $C(═O)OR_e$, $C(═O)R_a$, $NR_bR_c$, $NR_bC(═O)R_a$, $C(═O)NR_bR_c$, $OC(═O)R_a$, or $OC(═O)NR_bR_c$,
wherein $R_1$ and $R_3$ together may optionally form a 3-7 membered unsaturated carbocyclic ring or 3-7 membered unsaturated heterocyclic ring, and wherein $R_a$, $R_b$, $R_c$ and $R_e$ are as described hereinabove;

$R_9$ is H, alkyl or substituted alkyl (including $CF_3$), cycloalkyl or substituted cycloalkyl, or $NR_bR_c$, and wherein $R_b$ and $R_c$ are as described hereinabove;

m is 1-4; and
n is 1-4;
provided that:
at least one of $R_6$ and $R_{10}$ is not H; and
when $X_1$═$X_2$ is —S—$CR_3R_4$—, each $R_{10}$ is H, and m=1, $R_6$ at the C-3 position is not H, methyl, halogen, OMe, $CF_3$, or $SCF_3$.

A more preferred subgenus of the compounds of the invention includes compounds of the formula I or an enantiomer, diastereomer, tautomer or pharmaceutically acceptable salt or solvate thereof, wherein one or more, preferably all, of the following substituents are as defined below:

Y is —C(═O)—, or —S(═O)$_2$—;
$X_1$═$X_2$ is —$CR_1$═$CR_3$—, —$CR_1R_2$—$CR_3R_4$—, —C(═O)—$CR_3R_4$—, —S—$CR_3R_4$—, —S(═O)—$CR_3R_4$—, —O—$CR_3R_4$—, —$CR_1R_2$—S—, —$CR_1R_2$—S(═O)—, —$CR_1R_2$—C(═O)—, or —$CR_1R_2$—O—;

$R_6$ and $R_{10}$ are each independently hydrogen, cyano, nitro, alkyl or substituted alkyl (including CF3), cycloalkyl or substituted cycloalkyl, heterocycle or substituted heterocycle, aryl or substituted aryl, $OR_a$, $SR_a$, $S(═O)R_e$, $S(═O)_2R_e$, $S(═O)_2OR_e$, $NR_bR_c$, $NR_bS(═O)_2R_e$, $S(═O)_2 NR_bR_c$, $C(═O)OR_e$, $C(═O)R_a$, $C(═O)NR_bR_c$, $OC(═O)R_a$, $OC(═O)NR_bR_c$, $NR_bC(═O)OR_e$, $NR_dC(═O)NR_bR_c$, $NR_dS(═O)_2NR_bR_c$, or $NR_bC(═O)R_a$,
wherein $R_a$, $R_b$, $R_c$, $R_d$ and $R_e$ are as described hereinabove;

$R_2$ and $R_4$ are each independently hydrogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $NR_bR_c$, $NR_bS(\!=\!O)_2R_e$, $S(\!=\!O)_2NR_bR_c$, $C(\!=\!O)OR_e$, $C(\!=\!O)R_a$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, or $NR_bC(\!=\!O)R_a$, wherein $R_2$ and $R_4$ together may optionally form a 3-6 membered optionally substituted carbocyclic ring or 3-6 membered optionally substituted heterocyclic ring, and wherein $R_a$, $R_b$, $R_c$, $R_d$ and $R_e$ are as described hereinabove;

$R_1$ and $R_3$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $C(\!=\!O)OR_e$, $C(\!=\!O)R_a$, $NR_bR_c$, $NR_bC(\!=\!O)R_a$, $C(\!=\!O)NR_bR_c$, $OC(\!=\!O)R_a$, or $OC(\!=\!O)NR_bR_c$, wherein $R_1$ and $R_3$ together may optionally form a 3-7 membered unsaturated carbocyclic ring or 3-7 membered unsaturated heterocyclic ring; and wherein $R_a$, $R_b$, $R_c$ and $R_e$ are as described hereinabove;

$R_9$ is H, $C_1$-$C_4$ alkyl or substituted $C_1$-$C_4$ alkyl (including $CF_3$), cycloalkyl or substituted cycloalkyl, or $NR_bR_c$, wherein $R_b$ and $R_c$ are as described hereinabove;

m is 1-4; and n is 1-4;

provided that:

at least one of $R_6$ and $R_{10}$ is not H; and when $X_1\!=\!\!=\!X_2$ is —S—$CR_3R_4$—, each $R_{10}$ is H, and m=1, $R_6$ at the C-3 position is not H, methyl, halogen, OMe, $CF_3$, or $SCF_3$.

Another more preferred subgenus of the compounds of the invention includes compounds of the formula I having the following structure Ia, or an enantiomer, diastereomer, tautomer or pharmaceutically acceptable salt or solvate thereof, wherein one or more, preferably all, of the following substituents are as defined below:

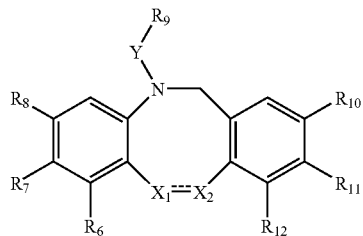

(Ia)

Y is —C(=O)—, or —S(=O)$_2$—;

$X_1\!=\!\!=\!X_2$ is —$CR_1\!=\!CR_3$—, —$CR_1R_2$—$CR_3R_4$—, —C(=O)—$CR_3R_4$—, —S—$CR_3R_4$—, —O—$CR_3R_4$—, —$CR_1R_2$—S—, or —$CR_1R_2$—O—;

$R_6$, $R_7$, $R_8$, $R_{10}$, $R_{11}$, and $R_{12}$ are each independently hydrogen, halogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $S(\!=\!O)_2OR_e$, $NR_bR_c$, $NR_bS(\!=\!O)_2R_e$, $S(\!=\!O)_2NR_bR_c$, $C(\!=\!O)OR_e$, $C(\!=\!O)R_a$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, or $NR_bC(\!=\!O)R_a$, wherein $R_a$, $R_b$, $R_c$, $R_d$ and $R_e$ are as described hereinabove;

$R_2$ and $R_4$ are each independently hydrogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $NR_bR_c$, $NR_bS(\!=\!O)_2R_e$, $S(\!=\!O)_2NR_bR_c$, $C(\!=\!O)OR_e$, $C(\!=\!O)R_a$, $C(\!=\!O)NR_bR_c$, $OC(\!=\!O)R_a$, $R_2$ and $R_4$ are each independently hydrogen, cyano, alkyl or substituted alkyl (including $CF_3$), cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $NR_bR_c$, $NR_bS(\!=\!O)_2R_e$, $S(\!=\!O)_2NR_bR_c$, $C(\!=\!O)OR_e$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, or $NR_bC(\!=\!O)R_a$, wherein $R_2$ and $R_4$ together may optionally form a 3-6 membered carbocyclic ring or 3-6 membered heterocyclic ring, and wherein $R_a$, $R_b$, $R_c$, $R_d$ and $R_e$ are as described hereinabove;

$R_1$ and $R_3$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $C(\!=\!O)OR_e$, $C(\!=\!O)R_a$, $NR_bR_c$, $NR_bC(\!=\!O)R_a$, $C(\!=\!O)NR_bR_c$, $OC(\!=\!O)R_a$, or $OC(\!=\!O)NR_bR_c$, wherein $R_1$ and $R_3$ together may optionally form a 3-6 membered unsaturated carbocyclic ring or 3-6 membered unsaturated heterocyclic ring; and wherein $R_a$, $R_b$, $R_c$ and $R_e$ are as described hereinabove; and $R_9$ is H, $C_1$-$C_4$ alkyl or substituted $C_1$-$C_4$ alkyl (including $CF_3$), cycloalkyl or substituted cycloalkyl, or $NR_bR_c$, wherein $R_b$ and $R_c$ are as described hereinabove;

provided that:

at least one of $R_6$, $R_7$, $R_8$, $R_{10}$, $R_{11}$, and $R_{12}$ is not H; and when $X_1\!=\!\!=\!X_2$ is —S—$CR_3R_4$—, each $R_{10}$ is H, and m=1, $R_6$ at the C-3 position is not H, methyl, halogen, OMe, $CF_3$, or $SCF_3$.

A particularly preferred subgenus of the compounds of the invention includes compounds of the formula I having the following structure Ib, or an enantiomer, diastereomer, tautomer or pharmaceutically acceptable salt or solvate thereof, wherein one or more, preferably all, of the following substituents are as defined below:

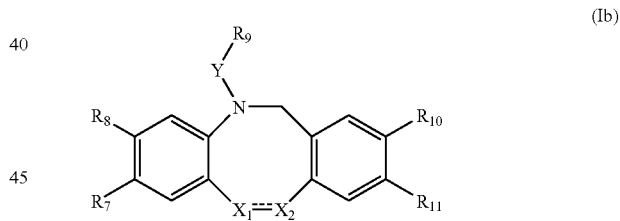

(Ib)

Y is —C(=O)—, or —S(=O)$_2$—;

$X_1\!=\!\!=\!X_2$ is —$CR_1\!=\!CR_3$—, —$CR_1R_2$—$CR_3R_4$—, or —C(=O)—$CR_3R_4$—;

$R_7$, $R_8$, $R_{10}$ and $R_{11}$ are each independently hydrogen, halogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $S(\!=\!O)_2OR_e$, $NR_bR_c$, $NR_bS(\!=\!O)_2R_e$, $S(\!=\!O)_2NR_bR_c$, $C(\!=\!O)OR_e$, $C(\!=\!O)R_a$, $C(\!=\!O)NR_bR_c$, $OC(\!=\!O)R_a$, $OC(\!=\!O)NR_bR_c$, $NR_bC(\!=\!O)OR_e$, $NR_dC(\!=\!O)NR_bR_c$, $NR_dS(\!=\!O)_2NR_bR_c$, or $NR_bC(\!=\!O)R_a$, wherein $R_a$, $R_b$, $R_c$, $R_d$ and $R_e$ are as described hereinabove;

$R_2$ and $R_4$ are each independently hydrogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(\!=\!O)R_e$, $S(\!=\!O)_2R_e$, $NR_bR_c$, $NR_bS(\!=\!O)_2R_e$, $S(\!=\!O)_2NR_bR_c$, $C(\!=\!O)OR_e$, $C(\!=\!O)R_a$, $C(\!=\!O)NR_bR_c$, $OC(\!=\!O)R_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_2$ and R$_4$ together may optionally form a 3-6 membered carbocyclic ring or 3-6 membered heterocyclic ring, and wherein R$_a$, R$_b$, R$_c$, R$_d$ and R$_e$ are as described hereinabove;

R$_1$ and R$_3$ are each independently hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein R$_1$ and R$_3$ together may optionally form a 3-6 membered unsaturated carbocyclic ring or 3-6 membered unsaturated heterocyclic ring; and wherein R$_a$, R$_b$, R$_c$ and R$_e$ are as described hereinabove; and R$_9$ is H, alkyl or substituted alkyl (including CF$_3$), cycloalkyl or substituted cycloalkyl, heterocycle or substituted heterocycle, aryl or substituted aryl, or NR$_b$R$_c$, wherein R$_b$ and R$_c$ are as described hereinabove;

provided that:

at least one of R$_7$, R$_8$, R$_{10}$ and R$_{11}$ is not H; and when X$_1$═══X$_2$ is —CH$_2$—CH$_2$—, R$_9$ is not aryl or substituted aryl, or heteroaryl or substituted heteroaryl.

Within this particularly preferred subgenus, especially preferred compounds include the following substituents as defined below:

Y is —C(=O)—;

X$_1$═══X$_2$ is —CH$_2$═CH$_2$—, —CH$_2$—CH$_2$—, or

R$_7$ and R$_8$ are each independently hydrogen, halogen, cyano, nitro, SMe, S(=O)$_2$Me, or OMe;

R$_{10}$ and R$_{11}$ are each independently hydrogen, halogen, cyano, alkyl or substituted alkyl (including CF$_3$), cycloalkyl or substituted cycloalkyl, heterocycle or substituted heterocycle, aryl or substituted aryl, OR$_e$, SR$_e$, S(=O)Re, S(=O)$_2$R$_e$, NR$_b$R$_c$, C(=O)OR$_e$, C(=O)R$_a$, C(=O)NR$_b$R$_c$, NR$_b$C(=O)OR$_e$, or NR$_b$C(=O)R$_a$, wherein R$_a$, R$_b$, R$_c$ and R$_e$ are as described hereinabove; and R$_9$ is methyl.

Another particularly preferred subgenus of the compounds of the invention includes compounds of the formula I having the structure Ib as shown above, or an enantiomer, diastereomer, tautomer or pharmaceutically acceptable salt or solvate thereof, wherein one or more, preferably all, of the following substituents are as defined below:

Y is —C(=O)—, or —S(=O)$_2$—;

X$_1$═══X$_2$ is —S—CR$_3$R$_4$—;

R$_7$, R$_8$, R$_{10}$ and R$_{11}$ are each independently hydrogen, cyano, nitro, alkyl or substituted alkyl (including CF$_3$), cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_a$, R$_b$, R$_c$, R$_d$ and R$_e$ are as described hereinabove; and R$_3$ and R$_4$ are each independently hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein R$_a$, R$_b$, R$_c$, and R$_e$ are as described hereinabove; and R$_9$ is H, alkyl or substituted alkyl (including CF$_3$), cycloalkyl or substituted cycloalkyl, heterocycle or substituted heterocycle, aryl or substituted aryl, or NR$_b$R$_c$, wherein R$_b$ and R$_c$ are as described hereinabove;

provided that:

at least one of R$_7$, R$_8$, R$_{10}$ and R$_{11}$ is not H; and when R$_7$, R$_{10}$ and R$_{11}$ are each H, R$_8$ is not H, methyl, halogen, OMe, CF$_3$, or SCF$_3$.

Within this particularly preferred subgenus, especially preferred compounds include the following substituents as defined below:

X$_1$═══X$_2$ is —S—CH$_2$—;

R$_7$ and R$_8$ are each independently hydrogen, halogen, cyano, nitro, SMe, S(=O)$_2$Me, or OMe;

R$_{10}$ and R$_{11}$ are each independently hydrogen, halogen, cyano, alkyl or substituted alkyl (including CF$_3$), cycloalkyl or substituted cycloalkyl, heterocycle or substituted heterocycle, aryl or substituted aryl, OR$_e$, SR$_e$, S(=O)R$_e$, S(=O)$_2$R$_e$, NR$_b$R$_c$, C(=O)OR$_e$, C(=O)R$_a$, C(=O)NR$_b$R$_c$, NR$_b$C(=O)OR$_e$, or NR$_b$C(=O)R$_a$, wherein R$_a$, R$_b$, R$_c$ and R$_e$ are as described hereinabove; and R$_9$ is methyl.

Another particularly preferred subgenus of the compounds of the invention includes compounds of the formula I having the structure Ib as shown above, or an enantiomer, diastereomer, tautomer or pharmaceutically acceptable salt or solvate thereof, wherein one or more, preferably all, of the following substituents are as defined below:

Y is —C(=O)—, or —S(=O)$_2$—;

X$_1$═══X$_2$ is —O—CR$_3$R$_4$—, —CR$_1$R$_2$—S—, or —CR$_1$R$_2$—O—;

R$_7$, R$_8$, R$_{10}$ and R$_{11}$ are each independently hydrogen, halogen, cyano, nitro, alkyl or substituted alkyl (including CF$_3$), cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_a$, R$_b$, R$_c$, R$_d$ and R$_e$ are as described hereinabove;

R$_2$ and R$_4$ are each independently hydrogen, cyano, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_a$, R$_b$, R$_c$, R$_d$ and R$_e$ are as described hereinabove;

R$_1$ and R$_3$ are each independently hydrogen, cyano, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, C(=O)NR$_b$R$_c$, OC(=O)R$_a$, or OC(=O)NR$_b$R$_c$, wherein R$_a$, R$_b$, R$_c$ and R$_e$ are as described hereinabove; and $R_9$ is H, alkyl or substituted alkyl (including $CF_3$), cycloalkyl or substituted cycloalkyl, heterocycle or substituted heterocycle, aryl or substituted aryl, or $NR_bR_c$, wherein $R_b$ and $R_c$ are as described hereinabove;

provided that at least one of $R_7$, $R_8$, $R_{10}$ and $R_{11}$ is not H.

Within this particularly preferred subgenus, especially preferred compounds include the following substituents as defined below:

$X_1 = X_2$ is $-O-CH_2-$, $-CH_2-S-$, or $-CH_2-O-$;

$R_7$ and $R_8$ are each independently hydrogen, halogen, cyano, nitro, SMe, $S(=O)_2Me$, or OMe;

$R_{10}$ and $R_{11}$ are each independently hydrogen, halogen, cyano, alkyl or substituted alkyl (including $CF_3$), cycloalkyl or substituted cycloalkyl, heterocycle or substituted heterocycle, aryl or substituted aryl, $OR_e$, $SR_e$, $S(=O)R_e$, $S(=O)_2R_e$, $NR_bR_c$, $C(=O)OR_e$, $C(=O)R_a$, $C(=O)NR_bR_c$, $NR_bC(=O)OR_e$, or $NR_bC(=O)R_a$, wherein $R_a$, $R_b$, $R_c$ and $R_e$ are as described hereinabove; and $R_9$ is methyl.

Use and Utility

The compounds of present invention are inhibitors of 17β-hydroxysteroid dehydrogenase 3 (17β-HSD3). They are useful in the treatment of androgen-associated conditions. An "androgen-associated condition," as used herein, denotes a condition or disorder that is caused or aided by modulation of the activity of the androgen receptor. The androgen-associated conditions can be treated by the reduction of androgen biosynthesis through inhibiting 17β-HSD3, wherein treatment comprises prevention, partial alleviation or cure of the condition or disorder.

The present compounds are also useful in the treatment of estrogen-associated conditions. An "estrogen-associated condition," as used herein, refers to a condition or disorder that is caused or aided by modulation of the activity of the estrogen receptor. The estrogen-associated conditions can also be treated by the reduction of androgen biosynthesis through inhibiting 17β-HSD3 because many androgens are precursors to estrogens. The treatment herein comprises prevention, partial alleviation or cure of the condition or disorder.

Further, estrogen-associated conditions may respond differently to androgens, i.e., they may respond adversely, favorably or neutrally to androgens. Similarly, androgen-associated conditions may vary in their responses to estrogens. Hence, treatment of a hormone sensitive disorder may adjust (i.e., increase or decrease) androgenic activity depending on whether the disorder reacts favorably or adversely toward androgenic activity. Likewise, treatment may also employ adjusting (i.e., increasing or decreasing) estrogenic activity depending on whether the disorder reacts favorably or adversely toward estrogenic activity. For example, prostate cancer responds adversely to androgenic activity and favorably to estrogenic activity; and breast cancer responds favorably to androgenic activity and adversely to estrogenic activity.

The treatment in both androgen- and estrogen-associated conditions may occur locally, for example, within certain tissues of the subject, or more extensively throughout a subject being treated for such a condition disorder.

The compounds of the present invention are useful for the treatment of a variety of conditions and disorders including, but not limited to, those described following.

Compounds of formula I can be used as inhibitors of 17β-HSD3 enzyme, preferably selectively to that enzyme, in an array of androgen-associated conditions. Applications of said compounds include but are not limited to: prostate cancer, hirsutism, acne, seborrhea, precocious puberty, Alzheimer's disease, androgenic alopecia, hypogonadism, hyperpilosity, benign prostate hypertrophia, benign prostatic hyperplasia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers modulation of VCAM expression and applications therein for the treatment of heart disease, inflammation and immune modulations, modulation of VEGF expression and the applications therein for use as antiandrogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients.

Compounds of formula I can also be applied in an array of estrogen-associated conditions. Applications of said compounds include but are not limited to: osteoporosis, hot flushes, vaginal dryness, breast cancer, ovarian cancer, uterine cancer, endometrial cancer, cancers expressing the estrogen receptor such as the aforementioned cancers and others, endometriosis, endometrial leiomyoma, contraception, pregnancy termination, menopause, amennoreahea, and dysmennoreahea.

The present invention thus provides methods for the treatment of androgen-associated or estrogen-associated conditions, comprising the step of administering to a subject in need thereof at least one compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with or following the administration of the compound(s) of the present invention.

The present invention also provides pharmaceutical compositions comprising at least one of the compounds of the formula I capable of treating an androgen-associated or estrogen-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention are, without limitation as to their mechanism of action, useful in treating any of the conditions or disorders listed or described herein such as inflammatory diseases or cancers, or other proliferate diseases, and in compositions for treating such conditions or disorders. Such conditions and disorders include, without limitation, any of those described previously, as well as those described following such as: maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic malagia; treatment of acute fatigue syndrome and muscle loss following elective surgery (e.g., post-surgical rehabilitation); acceleration of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength; and the conditions, diseases, and maladies collectively referenced to as "Syndrome X" or Metabolic Syndrome as detailed in Johannsson *J. Clin. Endocrinol. Metab.*, 82, 727-34 (1997).

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosupressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a compound of the formula I attenuates any actual inflammation (such as, for example, the rejection of a transplanted organ or tissue).

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms that may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methylcellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 1 to 100 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to androgen-associated and/or estrogen-associated conditions.

As mentioned above, the compounds of the present invention can be employed alone or in combination with each other and/or other suitable therapeutic agents useful in the treatment of androgen-associated and/or estrogen-associated conditions, e.g., an antibiotic or other pharmaceutically active material.

For example, the compounds of the present invention can be combined with growth promoting agents, such as, but not limited to, TRH (Thyroid Receptor Hormone), diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention can also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

A further use of the compounds of this invention is in combination with progesterone receptor agonists ("PRA"), such as levonorgestrel, medroxyprogesterone acetate (MPA).

The compounds of the present invention can be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Pat. No. 6,548,529 filed Mar. 6, 2000, glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, steroidal or non-steroidal progesterone receptor agonists, RANK ligand antagonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), and WO 99/00353 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®) integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epothilones, cisplatin and carboplatin.

Compounds of the present invention can further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

In addition, compounds of the present invention can be used in combination with therapeutic agents used in the treatment of sexual dysfunction, including but not limited to PDE5 inhibitors, such as sildenafil or IC-351; with an antiresorptive agent, hormone replacement therapies, vitamin D analogues, calcitonins, elemental calcium and calcium supplements, cathepsin K inhibitors, MMP inhibitors, vitronectin receptor antagonists, Src $SH_2$ antagonists, vacular —$H^+$-ATPase inhibitors, progesterone receptor agonists, ipriflavone, fluoride, RANK antagonists, PTH and its analogues and fragments, Tibolone, HMG-CoA reductase inhibitors, SERM's, p38 inhibitors, prostanoids, 17-beta hydroxysteroid dehydrogenase inhibitors and Src kinase inhibitors.

Compounds of the present invention can be used in combination with male contraceptives, such as nonoxynol 9 or therapeutic agents for the treatment of hair loss, such as minoxidil and finasteride or chemotherapeutic agents, such as with LHRH agonists.

For their preferred anticancer or antiangiogenic use, the compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; $5\alpha$ reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR (nuclear hormone receptor) modulators such as AR (androgen receptor) modulators, ER (estrogen receptor) modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

As it pertains to the treatment of cancer, the compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists or antagonists or with surgical castration.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The compounds of the present invention can be employed as AR antagonists in complete ablation therapy, alone or in combination with other AR antagonists such as Flutamide, Casodex, Nilutamide, or Cyproterone acetate.

Another application of the present compounds is in combination with antibody therapy such as but not limited to antibody therapy against PSCA. An additional application is in concert with vaccine/immune modulating agents for the treatment of cancer.

Compounds of the present invention can be employed in accordance with the methods described in U.S. Pat. No. 6,960,474, entitled "Selective Androgen Receptor Modulators and Methods for their Identification, Design and Use" filed Jun. 20, 2001, which Patent is incorporated herein by reference in its entirety; U.S. Patent Application Publication No. US 2004/0176324 A1, entitled "used Heterocyclic Succinimide Compounds and Analogs Thereof, Modulators of Nuclear Hormone Receptor Function" filed Jun. 20, 2001, which Patent Application Publication is incorporated herein by reference in its entirety; and U.S. patent application Ser. No. 09/885,798, now abandoned, entitled "Fused Cyclic Modulators of Nuclear Hormone Receptor Function" filed Jun. 20, 2001, which Patent Application is incorporated herein by reference in its entirety (including, but not limited to, reference to all specific compounds within formula I of the present invention).

The above other therapeutic agents, when employed in combination with the compounds of the present invention, can be used, for example, in those amounts indicated in the Physicians' Desk Reference (PDR) or as otherwise determined by one of ordinary skill in the art.

The following assays can be employed in ascertaining the activity of a compound as a 17β-HSD3 inhibitor. Various compounds of the present invention were determined to have 17β-HSD3 inhibition activity utilizing the enzymatic and transactivation assays as described below.

Assays

17β-HSD3 enzymatic activity and its inhibition through various compounds were determined in cell extracts using a scintillation proximity assay (SPA) or within cells using a 17β-HSD3 driven secreted alkaline phosphatase (SEAP) reporter assay. In the 17β-HSD3 SPA assay, 17β-HSD3 enzyme was prepared from HEK293 cells, a human kidney epithelial cell line that does not express endogenous 17β-HSD3 protein, engineered to over express a cDNA clone encoding full length human 17β-HSD3. Stable clonal populations of HEK293 cells expressing 17β-HSD3 were established upon antibiotic selection with G418 (500 µg/ml). Individual 17β-HSD3 HEK293 transfectants were analyzed by Western blotting for 17β-HSD3 protein levels and assay for androstenedione to testosterone conversion activity. Clonal populations with significant 17β-HSD3 activity were expanded and cellular lysates were prepared by homogenization followed by high-speed centrifugation for use in the 17β-HSD3 SPA.

The inhibitory activity of compounds was first evaluated in the 17β-HSD3 SPA format. Briefly, HEK293 lysates containing recombinant 17β-HSD3 were incubated with {3H} androstenedione for 60 minutes with gentle rocking in the presence or absence of compound (up to 30 µM) in a total volume of 30 µl. The enzymatic reaction of 17β-HSD3 was terminated by the addition of 10 µl of 0.1 N HCL. The {3H}-testosterone converted by 17β-HSD3 was captured and quantified using a monoclonal antibody against testosterone that was pre-conjugated to anti-mouse IgG Yttrium silicate SPA beads.

A 17β-HSD3-driven cell based assay was established using MB-MDA231 cells and an androgen-responsive gene promoter reporter construct. In this assay, 17β-HSD3 converted testosterone is monitored by the transcriptional activity of the endogenous androgen receptor through the introduction of androgen responsive prostate specific antigen (PSA) promoter. To set up this system, MB-MDA23 1, which do not express 17β-HSD3, were transfected with human 17β-HSD3 and clonal populations were selected and analyzed as described above. Clonal cell lines showing moderate androstenedione to testosterone conversion activity by thin layer chromatography (TLC) analysis were used to determine the inhibitory activity of compounds. 17β-HSD3-MB-MDA-23 1 transfectants were transfected with a PSA SEAP reporter and grown in cell culture overnight. The PSA promoter contains several androgen receptor-binding elements which are sufficient to drive an androgen responsive transcriptional response. The following day, 17β-HSD3 transfectants containing the PSA-SEAP promoter were incubated with 10 nM androstenedione in the presence or absence of compound for 18 hours. Cellular media was harvested and analyzed for alkaline phosphatase activity by standard methods.

EXAMPLES

Abbreviations
The following abbreviations are used herein.

| | |
|---|---|
| Ac | Acetyl |
| AcOH | Acetic acid |

-continued

| | |
|---|---|
| aq. | Aqueous |
| BH₃·DMS | Borane-dimethyl sulfide complex |
| BINAP | 2,2'-bis(diphenylphosphino)-1,1'-binaphthylbenzyl |
| Bn | Benzyl |
| Boc | tert-Butoxycarbonyl |
| BOP | Benzotriazol-1-yloxytris(dimethylamino)phosphonium hexaflurophosphate |
| n-BuOH | n-Butanol |
| CDI | Carbonyldiimidazole |
| DIEA | N,N-Diisopropyl ethylamine |
| DMAP | Dimethylaminopyridine |
| DMF | Dimethylformamide |
| DMSO | Dimethylsulfoxide |
| EDCI | 1-(3-Dimethylaminopropyl)-3-ethylcarbodiimide hydrochloride |
| Et | Ethyl |
| Et₂O | Ether |
| EtOAc | Ethyl acetate |
| EtOH | Ethanol |
| h | Hours |
| HOBt | 1-Hydroxybenzotriazole |
| HPLC | High pressure liquid chromatography |
| i | iso |
| LC/MS | High performance liquid chromatography/mass spectrometry |
| LDA | Lithium diisopropylamide |
| mCPBA | 3-Chloroperoxybenzoic acid |
| Me | Methyl |
| MeI | Methyl iodide |
| MeOH | Methanol |
| min. | Minutes |
| m/z | Mass spectrometry |
| n | Normal |
| Pd/C | Palladium on carbon |
| Ph | Phenyl |
| Prep HPLC | Preparative reverse phase HPLC |
| p-TsOH | para-Toluenesulonic acid |
| Rh/C | Rhodium on carbon |
| R$_t$ | Retention time |
| rt or RT | Room temperature |
| sat. | Saturated |
| Tf | trifluoromethanesulfonyl |
| TFA | Trifluoroacetic acid |
| THF | Tetrahydrofuran |
| YMC | YMC Inc, Wilmington, NC 28403 |

HPLC condition: YMC S5 ODS column 4.6×50 mm, 10-90% aqueous methanol over 4 minutes containing 0.2% H₃PO₄, 3 mL/min, monitoring at 220 nm. This is the default HPLC condition unless otherwise noticed.

Conditions with Note:

(a) (YMC S5 ODS column 4.6×50 mm, 50-90% aqueous methanol over 2 minutes containing 0.2% H₃PO₄, 3 mL/min, monitoring at 220 nm)

(b) (YMC S5 ODS column 4.6×50 mm, 10-90% aqueous methanol over 2 minutes containing 0.2% H₃PO₄, 3 mL/min, monitoring at 220 nm)

(c) YMC S5 ODS column 4.6×50 mm, 10-90% aqueous methanol over 4 minutes containing 0.2% TFA, 3 mL/min, monitoring at 220 nm.

(d) YMC PRO S5 ODS column 4.6×33 mm, 10-90% aqueous methanol over 2 minutes containing 0.2% TFA, 3 mL/min, monitoring at 220 nm Compounds prepared are referred to in places hererin by the step with which they are prepared. For example, the compound prepared in step 2A is referred to herein as "2A." The title compound of an Example can be referred to by the Example number (e.g., "Example 64").

Example 1

5-Acetyl-8-bromo-2-chloro-5,6-dihydro-dibenz[b,f]azocine

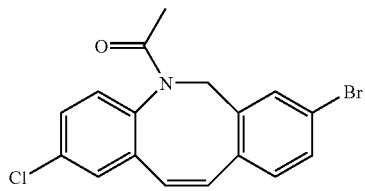

Method One:

1A. Preparation of 6-Bromo-indan-1-one

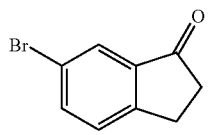

To a 3-neck 250 mL round bottom flask equipped with a mechanical stirrer and charged with anhydrous aluminum chloride (16.6 gm, 0.125 mole) was added indanone (6.6 gm, 0.05 mole) in-two portions over 3 minutes. The reaction mixture was stirred for 10 minutes before bromine (9.7 g, 0.06 mole) was added dropwise over 10 minutes. The reaction mixture was heated to 80° C. for 5 minutes. The resulting mixture was poured into a mixture of ice (100 g) and concentrated HCl (20 mL). The resulting mixture was extracted with ether. The ether layer was separated, washed with water, dried (Na₂SO₄), filtered and concentrated. The crude material was purified by flash chromatography over silica gel eluting with 15% ether/hexanes to afford 6-Bromo-indan-1-one(2.0g, 19%). $^1$HNMR(CDCl₃) δ 7.81 (d, 1H, J=1.76 Hz),7.62 (dd, 1H, J=8.36, 2.20 Hz), 7.30 (d, 1H, J=8.30 Hz), 3.03 (t, 2H, J=6.16 Hz), 2.65 (t, 2H, J=6.20 Hz). HPLC R$_t$=3.09 min.

1B. Preparation of N-(6-Bromo-indan-1-ylidene)-N'-(4-chloro-phenyl)-hydrazine

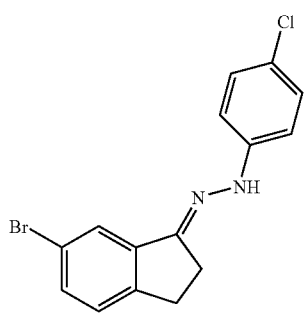

To a mixture of 6-Bromo-indan-1-one (0.58 g, 2.7 mmole) in ethyl alcohol (5 mL) was added (4-Chloro-phenyl)-hydrazine (0.492 g, 2.7 mmole) and 5 drops of acetic acid. The reaction mixture was refluxed for 30 minutes then cooled to room temperature. The resulting solid precipitate was filtered and washed with ice cold methanol to give N-(6-Bromo-indan-1-ylidene)-N'-(4-chloro-phenyl)-hydrazine (0.92 gm, 100%). HPLC $R_t$=4.69 min. m/z=335 (M+H$^+$).

1C. Preparation of 3-Bromo-8-chloro-5,10-dihydro-indeno[1,2-b]indole

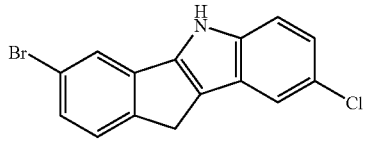

To a mixture of N-(6-Bromo-indan-1-ylidene)-N'-(4-chloro-phenyl)-hydrazine (0.92 g, 2.7 mmole) in acetic acid (5 mL) was added sulfuric acid (0.242 g, 2.46 mmole). The reaction mixture was heated to 90° C. for 3 hours then cooled to room temperature. The resulting solid precipitate was filtered, washed with cold water and dried in vacuo to give 3-Bromo-8-chloro-5,10-dihydro-indeno[1,2-b]indole (0.638 g, 73%). $^1$HNMR (DMSO-d$_6$) δ7.76 (d, 1H, J=1.65 Hz), 7.62 (d, 1H, J=2.2 Hz), 7.51 (m, 2H), 7.39 (dd, 1H, J=8.20, 1.65 Hz), 7.12 (dd, 1H, J=8.20, 2.20 Hz), 3.68 (s, 2H). HPLC $R_t$=4.71 min.

1D. Preparation of 8-Bromo-2-chloro-5H,11H-dibenzo[b,f]azocine-6-12-dione

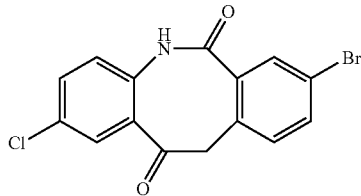

To a solution 3-Bromo-8-chloro-5,10-dihydro-indeno[1,2-b]indole (4.2 g, 13 mmol) in chloroform (150 mL) and 5% aqueous NaHCO$_3$ (56 mL) was added mCPBA (7.5 g, 43 mmol) in chloroform (150 mL) dropwise over 30 minutes. The reaction mixture was stirred at room temperature for 2 hours and the layers were separated. The organic layer was washed with saturated aqueous NaHCO$_3$, dried (Na$_2$SO$_4$), filtered and concentrated. The resulting oil was triturated with ether and filtered. The filter cake was washed with ether and dried in vacuo to give 8-Bromo-2-chloro-5H,11H-dibenzo[b,f]azocine-6-12-dione (2.0 g, 43%). $^1$HNMR (CDCl$_3$) δ 7.67 (d, 1H, J+2.20 Hz), 7.59 (d, 1H, J=1.76 Hz), 7.42 (dd, 1H, J=7.92, 1.76 Hz), 7.32 (dd, 1H, J=8.01, 2.20 Hz), 7.02 (m, 2H), 4.44 (d, 1H, J=15.40 Hz), 3.85 (d, 1H, J=14.96 Hz). HPLC $R_t$=3.65 min.

1E. Preparation of 8-Bromo-2-chloro-5,6,11,12-tetrahydro-dibenzo[b,f]azocine-12-ol

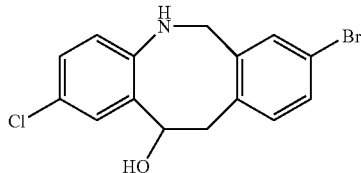

To a mixture of 8-Bromo-2-chloro-5H,11H-dibenzo[b,f] azocine-6-12-dione (2.0 g, 5.7 mmole) in THF (20 mL) was added a 2.0M solution of BH$_3$.DMS in THF (6.9 mL, 14.3 mmole). The reaction mixture was heated to 70° C. for 6 hours. The reaction was quenched by slow addition of methanol and stirred at room temperature for 40 minutes. The residue obtained after concentration was triturated with methanol, filtered and dried in vacuo to give 8-Bromo-2-chloro-5,6,11,12-tetrahydro-dibenzo[b,f]azocine-12-ol (0.85 g, 44%). HPLC $R_t$=3.31 min. m/z=338 (M+H$^+$).

1F. Preparation of 8-Bromo-2-chloro-5,6-dihydro-dibenzo[b,f]azocine

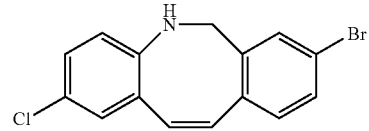

To a mixture of 8-Bromo-2-chloro-5,6,11,12-tetrahydro-dibenzo[b,f]azocine-12-ol (0.85 g, 2.5 mmole) in dioxane (10 mL) was added concentrated HCl (1 mL). The reaction was heated to reflux for 24 hours. The reaction mixture was concentrated and the residue obtained was dissolved in ethyl acetate, washed with saturated aqueous NaHCO$_3$, dried (Na$_2$SO$_4$), filtered and concentrated to give 8-Bromo-2-chloro-5,6-dihydro-dibenzo[b,f]azocine (0.7 g, 87%). HPLC $R_t$=4.33 min. m/z=320 (M+H$^+$).

Example 1

Preparation of 1-(8-Bromo-2-chloro-6H-dibenzo[b,f]azocin-5-yl)-ethanone

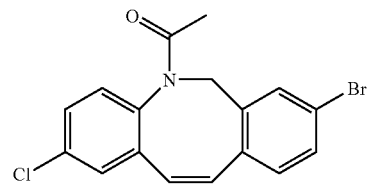

To a mixture of 8-Bromo-2-chloro-5,6-dihydro-dibenzo[b,f]azocine (0.8 g, 2.5 mmole) in toluene (10 mL) was added acetic anhydride (1.2 mL, 12.5 mmole) and N,N-dimethylaminopyridine (1.51 g, 12.5 mmole). The reaction mixture was refluxed for 2 hours, concentrated and purified by flash chromatography over silica gel eluting with 30% ethyl acetate/hexane to give 1-(8-Bromo-2-chloro-6H-dibenzo[b,f]azocin-5-yl)-ethanone (0.65 g, 72%). $^1$HNMR (CDCl$_3$) δ7.32 (d, 1H, J=1.76 Hz), 7.23 (dd, 1H, J=7.70, 1.76 Hz), 7.19 (m, 2H), 7.06 (d, 1H, J=8.80 Hz), 6.91 (d, 1H, J=8.36 Hz), 6.68 (d, 1H, J=13.16 Hz), 6.47 (d, 1H, J=12.76 Hz), 5.42 (d, 1H, J=14.96 Hz), 4.08 (d, 1H, J=15.36 Hz), 1.68 (s, 3H). HPLC $R_t$=4.05 min. m/z=362 (M+H$^+$).

Method Two:

1G. Preparation of (5-Bromo-2-iodo-phenyl)-m-ethanol

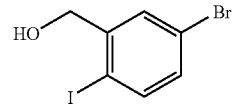

To a stirred mixture of acid 2-iodo-5-bromobenzoic acid (15.0 g, 45.9 mmol) in dry THF (100 mL) under argon was added neat BH$_3$.DMS (16.0 mL, 169 mmol) dropwise over 20 minutes. The resulting mixture was heated at 65° C. for 8 hours, cooled to room temperature and quenched by the dropwise addition of water (40 mL). The reaction mixture was concentrated in vacuo. The crude alcohol was diluted with of EtOAc (300 mL), washed with 1N NaOH (2×30 mL), 1N HCl (1×30 mL), saturated aqueous NaHCO$_3$ solution (1×30 mL) and brine (1×30 mL). The EtOAc layer was dried (MgSO$_4$), filtered and concentrated in vacuo to give 2-iodo-5-bromobenzyl alcohol (13.8 g, 96%). $^1$H NMR (CDCl$_3$): δ 7.56 (d, 1H, J=8.25 Hz), 7.54 (s, 1H), 7.04 (d, 1H, J=8.25 Hz), 4.47 (s, 2H). HPLC: R$_t$=3.12 min. m/z=312 (M+H$^+$).

1H. Preparation of 4-Bromo-2-bromomethyl-1-iodo-benzene

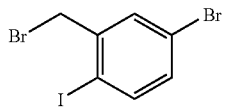

To a stirred mixture of (5-Bromo-2-iodo-phenyl)-methanol (9.14 g, 29.2 mmol) in CH$_3$Cl (150 mL) under argon was added 1M PBr$_3$ in CH$_2$Cl$_2$ (35.0 mL, 35.0 mmol). The reaction mixture was stirred at room temperature for 20 min and then poured into a mixture of ice and saturated NaHCO$_3$ solution (300 mL). The pH was adjusted to basic by addition of solid NaHCO$_3$. This aqueous layer was extracted with EtOAc (1×600 mL, 2×400 mL). The combined EtOAc extracts were washed with brine (1×100 mL). The organic layer was dried (MgSO$_4$), filtered and concentrated in vacuo to give 4-bromo-2-bromomethyl-1-iodo-benzene (5.69 g, 52%). $^1$H NMR (CDCl$_3$): δ 7.68 (d, 1H, J=8.80 Hz), 7.59 (s, 1H), 7.18 (d, 1H, J=8.80 Hz), 4.51 (s, 2H). HPLC: R$_t$=3.87 min.

1I. Preparation of N-(2-Bromo-4-chloro-phenyl)-acetamide

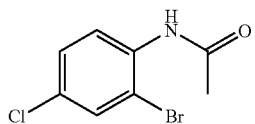

To a stirred mixture of 2-bromo-4-chloroaniline (5 g, 24 mmol) and catalytic DMAP in CH$_2$Cl$_2$ (15 mL) was add acetic anhydride (2.3 mL, 24 mmol) at room temperature. The reaction mixture was stirred overnight then washed with saturated aqueous NaHCO$_3$ solution. The CH$_2$Cl$_2$ layer was dried (MgSO$_4$), filtered, concentrated in vacuo. The crude material was triturated with Hexane/Et$_2$O and the solid filtered and dried in vacuo to give N-(2-bromo-4-chloro-phenyl)-acetamide (5.2 g, 86%). HPLC: R$_t$=2.26 min. m/z=248 (M+H$^+$).

1J. Preparation of N-(4-Chloro-2-vinyl-phenyl)-acetamide

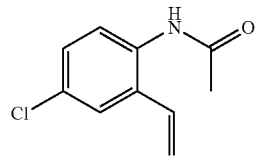

To a stirred solution of N-(2-bromo-4-chloro-phenyl)-acetamide (2 g, 8 mmol) in toluene (20 mL) was added tributyl (vinyl)tin (3.05 mL, 10.5 mmol) and dichlorobis(triphenylphosphine)palladium (II) (1.41 g, 2 mmol). The reaction mixture was heated at 95° C. for 1 hour, and the solvent removed in vacuo. The residue obtained was purified by flash chromatography eluting with 20% ethyl acetate/CH$_2$Cl$_2$ to give N-(4-Chloro-2-vinyl-phenyl)-acetamide (1 g, 64%). HPLC: R$_t$=2.16 min. m/z=196 (M+H$^+$).

1K. Preparation of N-(4-Chloro-2-vinyl-phenyl)-N-(2,5-dibromo-benzyl)-acetamide

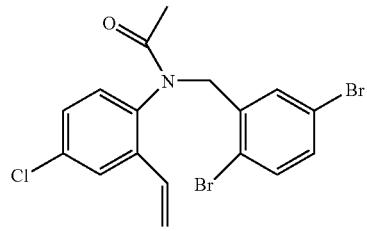

To a stirred mixture of N-(4-Chloro-2-vinyl-phenyl)-acetamide (0.26 g, 1.33 mmol) and 4-bromo-2-bromomethyl-1-iodo-benzene (0.5 g, 1.33 mmol) in DMF (5 mL) was added NaH (32 mg) at room temperature. The reaction mixture was stirred for 30 minutes then poured into H$_2$O (50 mL) and extracted with Et$_2$O(20 mL). The Et$_2$O layer was washed with H$_2$O (2×20mL) and brine (20 mL), dried (MgSO$_4$), filtered and concentrated in vacuo to give N-(4-chloro-2-vinyl-phenyl)-N-(2,5-dibromo-benzyl)-acetamide(0.55 g, 84%).

Example 1

Preparation of 1-(8-Bromo-2-chloro-6H-dibenzo[b,f]azocin-5-yl)-ethanone

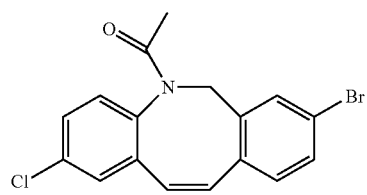

To a stirred solution of N-(5-Bromo-2-iodo-benzyl)-N-(4-chloro-2-vinyl-phenyl)-acetamide (0.55 g, 1.5 mmol) and Et$_3$N (0.63 mL, 4.5 mmol) in DMF (25 mL) was added PdCl$_2$ (40 mg, 0.23 mmol) and the reaction was heated to 60° C. When the reaction was complete by HPLC the mixture was poured into H$_2$O and extracted with Et$_2$O. The Et$_2$O layer was washed with H$_2$O (2×20mL) and brine (20 mL), dried (MgSO$_4$), filtered and concentrated in vacuo. The residue obtained was purified by flash chromatography eluting with CH$_2$Cl$_2$ to give 1-(8-Bromo-2-chloro-6H-dibenzo[b,f]azocin-5-yl)-ethanone (0.24 g, 60%).

Examples 2 to 20

The compounds listed in Table 1 were prepared according to Example 1 by either Method 1 or Method 2.

TABLE 1

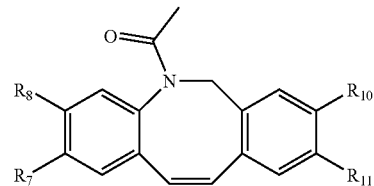

| Example No. | R$_7$ | R$_8$ | R$_{10}$ | R$_{11}$ | Compound Name | [M + H] | HPLC Ret Time (min) |
|---|---|---|---|---|---|---|---|
| 2 | H | H | H | Br | 5-Acetyl-9-bromo-5,6-dihydro-dibenz[b,f]azocine | 328.1 | 4.08 |
| 3 | Cl | H | H | Br | 5-Acetyl-9-bromo-2-chloro-5,6-dihydro-dibenz[b,f]azocine | 363.98 | 4.38 |
| 4 | H | H | H | H | 5-Acetyl-5,6-dihydro-dibenz[b,f]azocine | 250 | 2.90(c) |
| 5 | H | Cl | Br | H | 5-Acetyl-8-bromo-3-chloro-5,6-dihydro-dibenz[b,f]azocine | 362 | 3.44(c) |
| 6 | H | H | F | Br | 5-Acetyl-9-bromo-8-fluoro-5,6-dihydro-dibenz[b,f]azocine | 346 | 3.27(c) |
| 7 | Cl | H | F | Br | 5-Acetyl-9-bromo-2-chloro-8-fluoro-5,6-dihydro-dibenz[b,f]azocine | 380 | 3.55(c) |
| 8 | H | Cl | F | Br | 5-Acetyl-9-bromo-3-chloro-8-fluoro-5,6-dihydro-dibenz[b,f]azocine | 380 | 3.47(c) |
| 9 | H | H | Br | F | 5-Acetyl-8-bromo-9-fluoro-5,6-dihydro-dibenz[b,f]azocine | 346 | 3.24(c) |
| 10 | Cl | H | Br | F | 5-Acetyl-8-bromo-2-chloro-9-fluoro-5,6-dihydro-dibenz[b,f]azocine | 380 | 3.52(c) |
| 11 | H | Cl | Br | F | 5-Acetyl-8-bromo-3-chloro-9-fluoro-5,6-dihydro-dibenz[b,f]azocine | 380 | 3.45 |
| 12 | MeO | H | Br | H | 5-Acetyl-8-bromo-5,6-dihydro-2-methoxy-dibenz[b,f]azocine | 359 | 3.46(c) |
| 13 | H | NO2 | Br | H | 5-Acetyl-8-bromo-5,6-dihydro-3-nitro-dibenz[b,f]azocine | 373 | 3.35 |
| 14 | H | NO2 | Br | F | 5-Acetyl-8-bromo-9-fluoro-5,6-dihydro-3-nitro-dibenz[b,f]azocine | 391 | 3.37 |
| 15 | H | H | Br | H | 5-Acetyl-8-bromo-5,6-dihydro-dibenz[b,f]azocine | 328 | 3.75 |
| 16 | H | H | H | MeO | 5-Acetyl-5,6-dihydro-9-methoxy-dibenz[b,f]azocine | 280 | 3.40 |
| 17 | Cl | H | H | H | 5-Acetyl-2-chloro-5,6-dihydro-dibenz[b,f]azocine | 284 | 1.74(a) |
| 18 | Cl | H | Br | MeO | 5-Acetyl-8-bromo-2-chloro-5,6-dihydro-9-methoxy-dibenz[b,f]azocine |  | 2.14(b) |
| 19 | Cl | H | H | MeO | 5-Acetyl-2-chloro-5,6-dihydro-9-methoxy-dibenz[b,f]azocine | 314 | 2.24(b) |
| 20 | H | Cl | Br | MeO | 5-Acetyl-3-chloro-8-bromo-5,6-dihydro-9-methoxy-dibenz[b,f]azocine | 392 | 2.32(b) |

Example 21

N-[2-(5-Acetyl-2-chloro-5,6,11,12-tetrahydro-dibenzo[b,f]azocin-8-yl)-phenyl]-acetamide

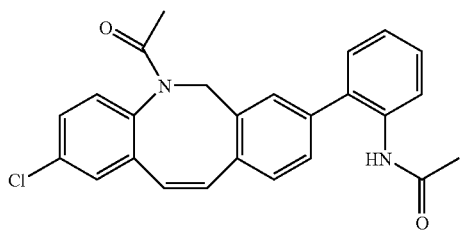

21A. Preparation of 1-[2-Chloro-8-(4,4,5,5-tetramethyl-[1,3,2]dioxaborolan-2-yl)-6H-dibenzo[b,f]azocin-5-yl]-ethanone

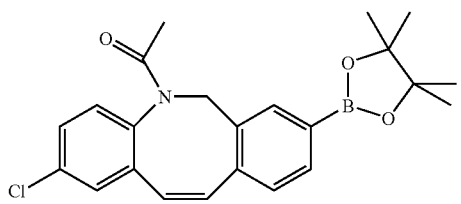

To a 10 mL round bottom flask was added Example 1 (0.1 g, 0.277 mmole) in dioxane (5 mL) under an argon atmosphere. To this solution was added (diphenylphosphino)ferrocine (15.4 mg, 0.027 mmole), bis(pinacolato)diboron (77.4 mg, 0.304 mmole), potassium acetate (81.5 mg, 0.83 mmole) and palladium dichloride(diphenylphosphino)ferrocine (20 mg, 0.027 mmole). The reaction mixture was heated to 90° C. for 6 hours. The reaction was concentrated, dissolved in 1:1 ethyl acetate/hexanes and passed through a pad of silica. The pure fractions were collected and concentrated to give 1-[2-Chloro-8-(4,4,5,5-tetramethyl-[1,3,2]dioxaborolan-2-yl)-6H-dibenzo[b,f]azocin-5-yl]-ethanone (90 mg, 80%). $^1$HNMR (CDCl$_3$) δ 7.63 (s, 1H), 7.60 (d, 1H, J=7.92 Hz), 7.20 (m, 2H), 7.10 (m, 2H), 6.87 (d, 1H, J=1276 Hz), 6.56 (d, 1H, J=12.28 Hz), 5.57 (d, 1H, J=15.4 Hz), 4.28 (d, 1H, J=14.96 Hz), 1.26 (s, 12H). HPLC R$_t$=4.34 min. m/z=410 (M+H$^+$).

21B. Preparation of N-[2-(5-Acetyl-2-chloro-5,6-dihydro-dibenzo[b,f]azocin-8-yl)-phenyl]-acetamide

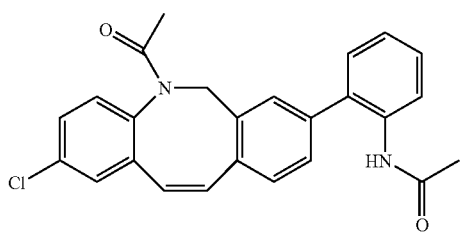

To a solution of Example 21A (20 mg, 0.05 mmol) and N-(2-Bromo-phenyl)-acetamide (17 mg, 0.08 mmol) in EtOH (0.75 mL) and toluene (0.75 mL) under an argon atmosphere were added 2M Na$_2$CO$_3$ (0.073 mL, 0.15 mmol) followed by Pd(PPh$_3$)$_4$ (5 mg). The resulting suspension was stirred under argon at 85° C. for 2 hours. The reaction was cooled to ambient temperature, concentrated and purified by reversed-phase HPLC, then radial chromatography (2mm plate, 1:1 EtOAc:Hexanes) to afford N-[2-(5-Acetyl-2-chloro-5,6-dihydro-dibenzo[b,f]azocin-8-yl)-phenyl]-acetamide (6 mg, 29%).

21C. Preparation of N-[2-(5-Acetyl-2-chloro-5,6,11,12-tetrahydro-dibenzo[b,f]azocin-8-yl)-phenyl]-acetamide

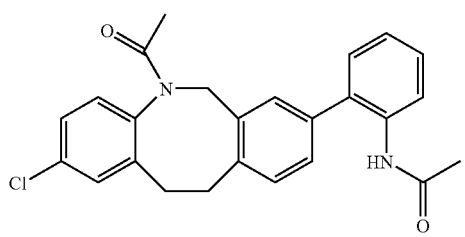

A suspension of Example 21B (6 mg, 0.014 mmol) and 5% Rh/C (4 mg) in MeOH (2 mL) was stirred under a hydrogen atmosphere for 3 hours. After consumption of the starting material, the reaction was filtered and concentrated. Reversed-phase HPLC afforded N-[2-(5-Acetyl-2-chloro-5,6,11,12-tetrahydro-dibenzo[b,f]azocin-8-yl)-phenyl]-acetamide (5 mg, 86%). HPLC R$_t$=3.56 min. m/z=419 (M+H$^+$).

Example 22

2-(5-Acetyl-2-chloro-5,6,11,12-tetrahydro-dibenzo[b,f]azocin-9-yl)-benzamide

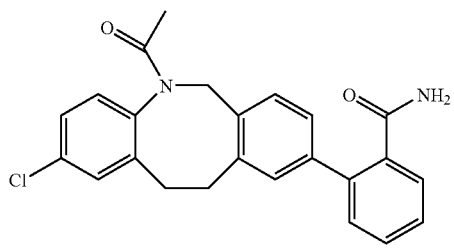

22A. Preparation of 1-(9-Bromo-2-chloro-11,12-dihydro-6H-dibenzo[b,f]azocin-5-yl)-ethanone

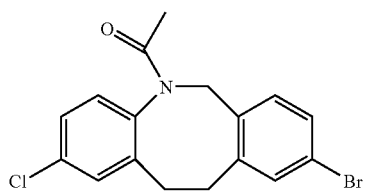

A solution of Example 3 (700 mg, 1.94 mmol) in MeOH (60 ML) and THF(10 mL) was treated with 5% Rh/C (200 mg). The resulting suspension was stirred under a hydrogen atmosphere for two hours. The resulting mixture was filtered through a pad of celite and concentrated. The crude material was purified by silica gel chromatography (30% to 40% EtOAc/Hexanes) to afford 1-(9-Bromo-2-chloro-11,12-dihydro-6H-dibenzo[b,f]azocin-5-yl)-ethanone 22A (654 mg, 93%).

22B. Preparation of 1-[2-Chloro-9-(4,4,5,5-tetramethyl-[1,3,2]dioxaborolan-2-yl)-11,12-dihydro-6H-dibenzo[b,f]azocin-5-yl]-ethanone

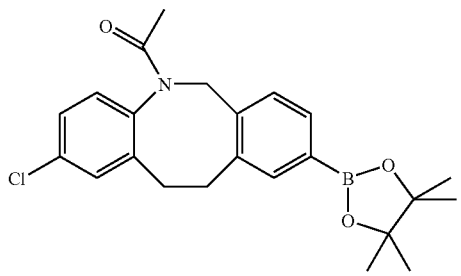

A solution of Example 22A (650 mg, 1.8 mmol) in dioxane (30 mL) was purged with argon and treated with dppf (100 mg, 0.18 mmol), KOAc (530 mg, 5.4 mmol) and bis(pinacolato)diboron (503 mg, 1.98 mmol). PdCl$_2$(dppf) (132 mg, 0.18 mmol) was added and the orange suspension was heated to 90° C. for two hours. The mixture was cooled to room temperature, diluted with EtOAc (100 mL), and washed with saturated aqueous NaCl (3×100 mL). The organic layer was dried (Na$_2$SO$_4$), filtered and concentrated. The crude product was filtered through a pad of silica eluting with 1:1 EtOAc:Hexanes to afford 1-[2-Chloro-9-(4,4,5,5-tetramethyl-[1,3,2]dioxaborolan-2-yl)-11,12-dihydro-6H-dibenzo[b,f]azocin-5-yl]-ethanone (675 mg, 91%).

Example 22

Preparation of 2-(5-Acetyl-2-chloro-5,6,11,12-tetrahydro-dibenzo[b,f]azocin-9-yl)-benzamide

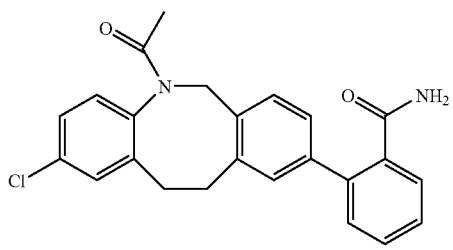

A 2 mL conical vial was charged with Example 22B (10 mg, 0.024 mmol), 2-bromo-benzamide (7 mg, 0.036 mmol) and Pd(PPh$_3$)$_4$ (3 mg). The vial was evacuated and purged with argon. EtOH (0.5 mL) and toluene (0.5 mL) were added, followed by 2M aqueous Na$_2$CO$_3$ (0.036 mL, 0.072 mmol). The reaction was heated to 80° C. until disappearance of the starting material was noted. The reaction was cooled to room temperature and concentrated. The product was purified by reversed-phase HPLC to afford 2-(5-Acetyl-2-chloro-5,6,11,12-tetrahydro-dibenzo[b,f]azocin-9-yl)-benzamide (5.6 mg, 58%). HPLC R$_t$=1.62(b) min. m/z=405 (M+H$^+$).

Example 23

5-Acetyl-2-chloro-5,6,11,12-tetrahydro-9-phenyl-dibenz[b,f]azocine

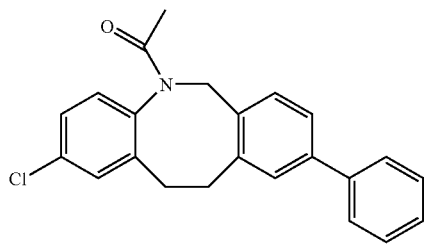

23A. Preparation of 1-(2-Chloro-9-phenyl-6H-dibenzo[b,f]azocin-5-yl)-ethanone

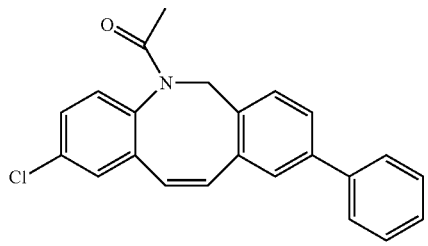

A solution of Example 3 (250 mg, 0.69 mmol) in toluene (25 mL) was treated with Pd(PPh$_3$)$_4$ (80 mg, 0.069 mmol) under an argon atmosphere. A solution of phenylboronic acid (126 mg, 1.04 mmol) in EtOH (10 mL) was added followed by aqueous 2M Na$_2$CO$_3$ (1.04 mL, 2.07 mmol) The resulting solution was heated to reflux for three hours. After cooling to room temperature, the mixture was treated with saturated aqueous NaCl solution (10 mL) and the layers were separated. The aqueous layer was extracted with EtOAc (3×20 mL). The combined organic layers were dried (Na$_2$SO$_4$), filtered and concentrated. The product was purified by radial chromatography (2 mm plate, 30% EtOAc/Hexanes) to afford 1-(2-Chloro-9-phenyl-6H-dibenzo[b,f]azocin-5-yl)-ethanone (205 mg, 83%).

Example 23

Preparation of 1-(2-Chloro-9-phenyl-11,12-dihydro-6H-dibenzo[b,f]azocin-5-yl)-ethanone

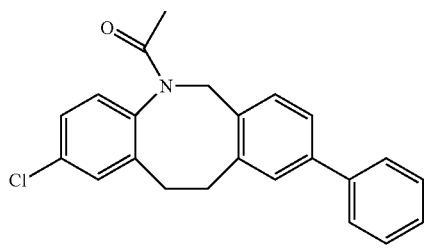

A solution of Example 23A (105 mg, 0.29 mmol) in MeOH (10 mL) and THF (2 mL) was treated with 5% Rh/C (30 mg). The suspension was stirred for seven hours under a hydrogen atmosphere. The resulting mixture was filtered through a nylon filter and concentrated to a white solid. The product was purified by radial chromatography (2 mm plate, 40% EtOAc/Hexanes) to afford 1-(2-Chloro-9-phenyl-11,12-dihydro-6H-dibenzo[b,f]azocin-5-yl)-ethanone (88 mg, 83%). HPLC $R_t$=2.25(b) min. m/z=362 (M+H$^+$).

Example 24

5-Acetyl-5,6,11,12-tetrahydro-8-(2-methoxyphenyl)-dibenz[b,f]azocine

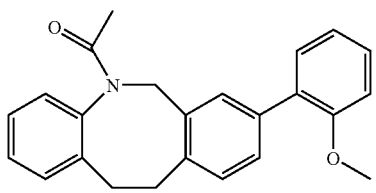

24A. Preparation of 1-(8-Bromo-11,12-dihydro-6H-dibenzo[b,f]azocin-5-yl)-ethanone

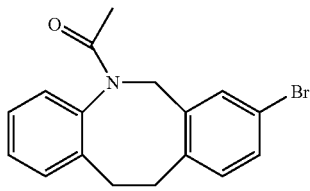

A solution of Example 2 (156 mg, 0.48 mmol) in MeOH (8 mL)) was treated with 5% Rh/C (50 mg). The resulting suspension was stirred under a hydrogen atmosphere for four hours. The resulting mixture was filtered through a pad of celite and concentrated. The crude material was purified by silica gel chromatography (30% to 40% EtOAc/Hexanes) to afford 1-(8-Bromo-11,12-dihydro-6H-dibenzo[b,f]azocin-5-yl)-ethanone (100 mg, 63%).

Example 24

Preparation of 1-[8-(2-Methoxy-phenyl)-11,12-dihydro-6H-dibenzo[b,f]azocin-5-yl]-ethanone

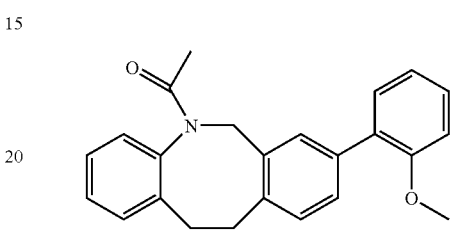

To a solution of Example 24A (30 mg, 0.09 mmol) and 2-methoxy-phenylboronic acid (21 mg, 0.14 mmol) in EtOH (0.8 mL) and toluene (0.8 mL) under an argon atmosphere were added 2M Na$_2$CO$_3$ (0.060 mL, 0.12 mmol) followed by Pd(PPh$_3$)$_4$ (5 mg). The resulting suspension was stirred under an argon atmosphere at 85° C. for 2 hours. The reaction was cooled to ambient temperature, concentrated and purified by reversed-phase HPLC, then radial chromatography (2 mm plate, 1:1 EtOAc:Hexanes) to afford 1-[8-(2-Methoxy-phenyl)-11,12-dihydro-6H-dibenzo[b,f]azocin-5-yl]-ethanone (20 mg, 62%) HPLC $R_t$=3.97 min. m/z=358 (M+H$^+$).

Examples 25 to 86

The following compounds in Table 2 have been synthesized utilizing the procedures described in Examples 2-5, starting from Example 1.

TABLE 2

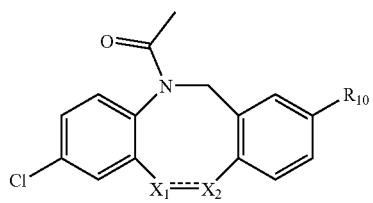

| Example No. | $X_1$===$X_2$ | $R_{10}$ | Compound name | [M + H] | HPLC Ret Time (min) |
|---|---|---|---|---|---|
| 25 | ![cis alkene] | ![3-acetylphenyl] | 5-Acetyl-8-(3-acetylphenyl)-2-chloro-5,6-dihydrodibenz[b,f]azocine | 402. (2M + 1 = 803.03) | 2.430(b) |

TABLE 2-continued

| Example No. | X₁═X₂ | R₁₀ | Compound name | [M + H] | HPLC Ret Time (min) |
|---|---|---|---|---|---|
| 26 | | 4-acetylphenyl | 5-Acetyl-8-(4-acetylphenyl)-2-chloro-5,6-dihydrodibenz[b,f]azocine | 402.36 | 2.430(b) |
| 27 | | 4-acetylpyridin-3-yl | 3-(5-Acetyl-2-chloro-5,6-dihydrodibenz[b,f]azocin-8-yl)-4-pyridinecarboxylic acid, methyl ester | 419.14 | 2.200(b) |
| 28 | | 4-methoxy-2-(2-oxazolyl)phenyl | 5-Acetyl-2-chloro-5,6-dihydro-8-[4-methoxy-2-(2-oxazolyl)phenyl]dibenz[b,f]azocine | 457.26 | 2.400(b) |
| 29 | | 5-fluoro-2-(methoxycarbonyl)phenyl | 2-(5-Acetyl-2-chloro-5,6-dihydrodibenz[b,f]azocin-8-yl)-5-fluorobenzoic acid, methyl ester | 436.04 | 2.430(b) |
| 30 | | 2-[(methylamino)sulfonyl]phenyl | 5-Acetyl-2-chloro-5,6-dihydro-8-[2-[(methylamino)sulfonyl]phenyl]dibenz[b,f]azocine | 453.22 | 3.807 |
| 31 | | 2-(aminosulfonyl)phenyl | 5-Acetyl-8-[2-(aminosulfonyl)phenyl]-2-chloro-5,6-dihydrodibenz[b,f]azocine | 439 | 3.650 |

TABLE 2-continued

| Example No. | X₁═══X₂ | R₁₀ | Compound name | [M + H] | HPLC Ret Time (min) |
|---|---|---|---|---|---|
| 32 | (cis alkene) | 2-CO₂Me, 5-CHO phenyl | 2-(5-Acetyl-2-chloro-5,6-dihydrodibenz[b,f]azocin-8-yl)-5-formylbenzoic acid, methyl ester | 446.16 | 2.297(b) |
| 33 | (cis alkene) | 2-S(O)Me phenyl | 5-Acetyl-2-chloro-5,6-dihydro-8-[2-(methyl-sulfinyl)phenyl]dibenz[b,f]azocine | 422.13 | 3.703 |
| 34 | (cis alkene) | 2-CO₂Me phenyl | 2-(5-Acetyl-2-chloro-5,6-dihydrodibenz[b,f]azocin-8-yl)benzoic acid, methyl ester | 418.11 | 4.067 |
| 35 | (cis alkene) | 2-NHC(O)Me phenyl | N-[2-(5-Acetyl-2-chloro-5,6-dihydrodibenz[b,f]azocin-8-yl)phenyl]acetamide | 417 | 3.73 |
| 36 | (cis alkene) | 2-Me phenyl | 5-Acetyl-2-chloro-5,6-dihydro-8-(2-methyl-phenyl)dibenz[b,f]azocine | 374.23 | 4.457 |
| 37 | (cis alkene) | 2-C(O)NHMe phenyl | 2-(5-Acetyl-2-chloro-5,6-dihydrodibenz[b,f]azocin-8-yl)-N-methylbenzamide | 417.17 | 3.587 |
| 38 | (cis alkene) | 2-CO₂Me, 6-OMe phenyl | 2-(5-Acetyl-2-chloro-5,6-dihydrodibenz[b,f]azocin-8-yl)-6-methoxybenzoic acid, methyl ester | 448.20 | 3.927 |

TABLE 2-continued

| Example No. | X₁⁼⁼⁼X₂ | R₁₀ | Compound name | [M + H] | HPLC Ret Time (min) |
|---|---|---|---|---|---|
| 39 | (cis CH=CH) | 4-pyridyl with 3-CO₂Me | 4-(5-Acetyl-2-chloro-5,6-dihydrodibenz[b,f]azocin-8-yl)-3-pyridinecarboxylic acid, methyl ester | 419.22 | 2.183(b) |
| 40 | (cis CH=CH) | 3-(N-methylcarbamoyl)phenyl | 3-(5-Acetyl-2-chloro-5,6-dihydrodibenz[b,f]azocin-8-yl)-N-methylbenzamide | 2M + 1 = 833.26 | 3.850 |
| 41 | (cis CH=CH) | 4-(N-methylcarbamoyl)phenyl | 4-(5-Acetyl-2-chloro-5,6-dihydrodibenz[b,f]azocin-8-yl)-N-methylbenzamide | 417.15 | 3.790 |
| 42 | (cis CH=CH) | 2-(CO₂Me)-4-OMe-phenyl | 2-(5-Acetyl-2-chloro-5,6-dihydrodibenz[b,f]azocin-8-yl)-5-methoxybenzoic acid, methyl ester | 448.10 | 2.417(b) |
| 43 | (cis CH=CH) | 2-(methylsulfonyl)phenyl | 5-Acetyl-2-chloro-5,6-dihydro-8-[2-(methylsulfonyl)phenyl]dibenz[b,f]azocine | 438.12 | 3.647 |
| 44 | (cis CH=CH) | 2-(CO₂Me)-4-(N-methylcarbamoyl)phenyl | 2-(5-Acetyl-2-chloro-5,6-dihydrodibenz[b,f]azocin-8-yl)-5-[(methylamino)carbonyl]benzoic acid, methyl ester | 475.31 | 3.670 |

TABLE 2-continued

| Example No. | X₁═X₂ | R₁₀ | Compound name | [M + H] | HPLC Ret Time (min) |
|---|---|---|---|---|---|
| 44B | | | 5-Acetyl-2-chloro-5,6-dihydro-8-[6-(5-oxazolyl)-1,3-benzodioxol-5-yl]dibenz[b,f]azocine, trifluoroacetic acid salt (1:1) | 471.15 | 4.117 |
| 45 | | | 6-(5-Acetyl-2-chloro-5,6-dihydrodibenz[b,f]azocin-8-yl)-1,3-benzodioxole-5-carboxylic acid, methyl ester | 462.22 | 4.097 |
| 46 | | | 5-Acetyl-2-chloro-5,6-dihydro-8-[6-(2-oxazolyl)-1,3-benzodioxol-5-yl]dibenz[b,f]azocine | 471.27 | 3.993 |
| 47 | | | 5-Acetyl-2-chloro-5,6-dihydro-8-[2-(1,3,4-oxadiazol-2-yl)phenyl]dibenz[b,f]azocine | 428.12 | 3.770 |
| 48 | | | 5-Acetyl-2-chloro-5,6-dihydro-8-[2-(5-methyl-1,3,4-oxadiazol-2-yl)phenyl]dibenz[b,f]azocine | 442.19 | 3.837 |

TABLE 2-continued

| Example No. | $X_1 = X_2$ | $R_{10}$ | Compound name | [M + H] | HPLC Ret Time (min) |
|---|---|---|---|---|---|
| 49 | (cis-CH=CH) | 2-(MeO-C(=O))-3-(MeNH-C(=O))-phenyl | 2-(5-Acetyl-2-chloro-5,6-dihydrodibenz[b,f]azocin-8-yl)-3-[(methylamino)carbonyl]benzoic acid, methyl ester | 475.22 | 3.297 |
| 50 | (cis-CH=CH) | 2,1,3-benzoxadiazol-4-yl | 5-Acetyl-8-(2,1,3-benzoxadiazol-4-yl)-2-chloro-5,6-dihydrodibenz[b,f]azocine | 402 | 4.27 |
| 51 | (cis-CH=CH) | 7-amino-2,1,3-benzoxadiazol-4-yl | 5-Acetyl-8-(7-amino-2,1,3-benzoxadiazol-4-yl)-2-chloro-5,6-dihydrodibenz[b,f]azocine | 417 | 2.44 |
| 52 | (cis-CH=CH) | phenyl | 5-Acetyl-2-chloro-5,6-dihydro-8-phenyldibenz[b,f]azocine | 360.22 | 4.370 |
| 53 | (cis-CH=CH) | 4-methoxyphenyl | 5-Acetyl-2-chloro-5,6-dihydro-8-(4-methoxy-phenyl)dibenz[b,f]azocine | 390.14 | 4.347 |
| 54 | (cis-CH=CH) | 3-methoxyphenyl | 5-Acetyl-2-chloro-5,6-dihydro-8-(3-methoxy-phenyl)dibenz[b,f]azocine | 390.19 | 4.340 |
| 55 | (cis-CH=CH) | 2-methoxyphenyl | 5-Acetyl-2-chloro-5,6-dihydro-8-(2-methoxy-phenyl)dibenz[b,f]azocine | 390.15 | 4.280 |

TABLE 2-continued

| Example No. | X$_1$====X$_2$ | R$_{10}$ | Compound name | [M + H] | HPLC Ret Time (min) |
| --- | --- | --- | --- | --- | --- |
| 56 | (cis-CH=CH) | 2-acetylphenyl | 5-Acetyl-8-(2-acetylphenyl)-2-chloro-5,6-dihydrodibenz[b,f]azocine | 402.06 | 3.943 |
| 57 | (cis-CH=CH) | 2-[(dimethylamino)sulfonyl]phenyl | 5-Acetyl-2-chloro-8-[2-[(dimethylamino)sulfonyl]phenyl]-5,6-dihydrodibenz[b,f]azocine | 467.29 | 3.790 |
| 58 | (CH$_2$CH$_2$) | phenyl | 5-Acetyl-2-chloro-5,6,11,12-tetrahydro-8-phenyldibenz[b,f]azocine | 362.23 | 4.263 |
| 59 | (CH$_2$CH$_2$) | 4-methoxyphenyl | 5-Acetyl-2-chloro-5,6,11,12-tetrahydro-8-(4-methoxyphenyl)dibenz[b,f]azocine | 392.15 | 4.210 |
| 60 | (CH$_2$CH$_2$) | 2-methoxyphenyl | 5-Acetyl-2-chloro-5,6,11,12-tetrahydro-8-(2-methoxyphenyl)dibenz[b,f]azocine | 392.19 | 4.157 |
| 61 | (CH$_2$CH$_2$) | 3-methoxyphenyl | 5-Acetyl-2-chloro-5,6,11,12-tetrahydro-8-(3-methoxyphenyl)dibenz[b,f]azocine | 392.08 | 4.217 |
| 62 | (CH$_2$CH$_2$) | 3-pyridinyl | 5-Acetyl-2-chloro-5,6,11,12-tetrahydro-8-(3-pyridinyl)dibenz[b,f]azocine, trifluoroacetic acid salt (1:1) | 363.18 | 2.687 |
| 63 | (CH$_2$CH$_2$) | 4-pyridinyl | 5-Acetyl-2-chloro-5,6,11,12-tetrahydro-8-(4-pyridinyl)dibenz[b,f]azocine, trifluoroacetic acid salt (1:1) | 363.16 | 2.560 |

TABLE 2-continued

| Example No. | X₁═══X₂ | R₁₀ | Compound name | [M + H] | HPLC Ret Time (min) |
|---|---|---|---|---|---|
| 64 | (cyclopentene) | 4-[2-(1-pyrrolidinyl)ethoxy]phenyl | 5-Acetyl-2-chloro-5,6,11,12-tetrahydro-8-[4-[2-(1-pyrrolidinyl)ethoxy]phenyl]dibenz[b,f]azocine, trifluoroacetic acid salt (1:1) | 475.24 | 3.107 |
| 65 | (cyclopentene) | 2-pyridinyl | 5-Acetyl-2-chloro-5,6,11,12-tetrahydro-8-(2-pyridinyl)dibenz[b,f]azocine, trifluoroacetic acid salt (1:1) | 363.17 | 2.760 |
| 66 | (cyclopentene) | 5-methyl-2-pyridinyl | 5-Acetyl-2-chloro-5,6,11,12-tetrahydro-8-(5-methyl-2-pyridinyl)dibenz[b,f]azocine, trifluoroacetic acid salt (1:1) | 377.24 | 2.783 |
| 67 | (cyclopentene) | 6-methyl-2-pyridinyl | 5-Acetyl-2-chloro-5,6,11,12-tetrahydro-8-(6-methyl-2-pyridinyl)dibenz[b,f]azocine, trifluoroacetic acid salt (1:1) | 377.20 | 2.637 |
| 68 | (cyclopentene) | 4-(methylsulfonyl)phenyl | 5-Acetyl-2-chloro-5,6,11,12-tetrahydro-8-[4-(methylsulfonyl)phenyl]dibenz[b,f]azocine | 440.13 | 3.563 |
| 69 | (cyclopentene) | 2-cyanophenyl | 5-Acetyl-2-chloro-8-(2-cyanophenyl)-5,6,11,12-tetrahydrodibenz[b,f]azocine | 387.22 | 3.797 |
| 70 | (cyclopentene) | 3-cyanophenyl | 5-Acetyl-2-chloro-8-(3-cyanophenyl)-5,6,11,12-tetrahydrodibenz[b,f]azocine | 387.21 | 3.930 |
| 71 | (cyclopentene) | 4-cyanophenyl | 5-Acetyl-2-chloro-8-(4-cyanophenyl)-5,6,11,12-tetrahydrodibenz[b,f]azocine | 387.15 | 3.913 |

TABLE 2-continued

| Example No. | X₁═══X₂ | R₁₀ | Compound name | [M + H] | HPLC Ret Time (min) |
|---|---|---|---|---|---|
| 72 | (cyclopentene) | 5-(trifluoromethyl)-2-pyridinyl (CF₃) | 5-Acetyl-2-chloro-5,6,11,12-tetrahydro-8-[5-(trifluoromethyl)-2-pyridinyl]dibenz[b,f]azocine, trifluoroacetic acid salt (1:1) | 431.08 | 4.123 |
| 73 | (cyclopentene) | 4-(SO₂NH₂)phenyl | 5-Acetyl-8-[4-(aminosulfonyl)phenyl]-2-chloro-5,6,11,12-tetrahydrodibenz[b,f]azocine | 441 | 3.407 |
| 74 | (cyclopentene) | 3-(SO₂NH₂)phenyl | 5-Acetyl-8-[3-(aminosulfonyl)phenyl]-2-chloro-5,6,11,12-tetrahydrodibenz[b,f]azocine | 441.09 | 3.407 |
| 75 | (cyclopentene) | 6-methoxy-3-pyridinyl (OMe) | 5-Acetyl-2-chloro-5,6,11,12-tetrahydro-8-(6-methoxy-3-pyridinyl)dibenz[b,f]azocine, trifluoroacetic acid salt (1:1) | 393.22 | 3.943 |
| 76 | (cyclopentene) | 2-(MeO₂C)phenyl | 2-(5-Acetyl-2-chloro-5,6,11,12-tetrahydrodibenz[b,f]azocin-8-yl)benzoic acid, methyl ester | 420.15 | 3.973 |
| 77 | (cyclopentene) | 3-(MeO₂C)phenyl | 3-(5-Acetyl-2-chloro-5,6,11,12-tetrahydrodibenz[b,f]azocin-8-yl)benzoic acid, methyl ester | 420 | 4.180 |
| 78 | (cyclopentene) | 2-(MeSO₂NH)phenyl | 5-Acetyl-2-chloro-5,6,11,12-tetrahydro-8-[2-[(methylsulfonyl)amino]phenyl]dibenz[b,f]azocine | 455.16 | 3.533 |

TABLE 2-continued

| Example No. | X₁===X₂ | R₁₀ | Compound name | [M + H] | HPLC Ret Time (min) |
|---|---|---|---|---|---|
| 79 | 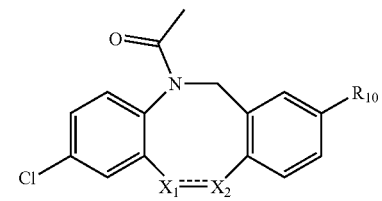 | 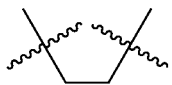 | 5-Acetyl-2-chloro-5,6,11,12-tetrahydro-8-[3-[(methylsulfonyl)amino]phenyl]dibenz[b,f]azocine | 455.14 | 3.687 |
| 80 | 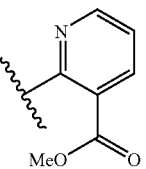 |  | 2-(5-Acetyl-2-chloro-5,6,11,12-tetrahydrodibenz[b,f]azocin-8-yl)-3-pyridinecarboxylic acid, methyl ester | 421.18 | 3.467 |
| 81 | 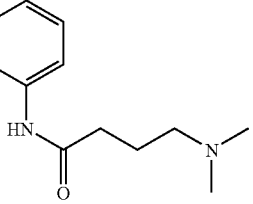 |  | N-[2-(5-Acetyl-2-chloro-5,6,11,12-tetrahydrodibenz[b,f]azocin-8-yl)phenyl]-4-(dimethylamino)butanamide | 490.25 | 2.993 |
| 82 | 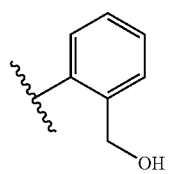 |  | 5-Acetyl-2-chloro-5,6,11,12-tetrahydro-8-[2-(hydroxymethyl)phenyl]dibenz[b,f]azocine | 392 | 3.823 |
| 83 | 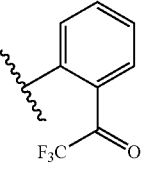 | 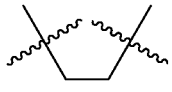 | 5-Acetyl-2-chloro-5,6,11,12-tetrahydro-8-[2-(trifluoroacetyl)phenyl]dibenz[b,f]azocine | 458.19 | 4.173 |
| 84 | 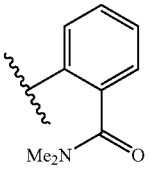 |  | 2-(5-Acetyl-2-chloro-5,6,11,12-tetrahydrodibenz[b,f]azocin-8-yl)-N,N-dimethylbenzamide | 433.30 | 3.597 |

TABLE 2-continued

[Structure: dibenzazocine core with N-acetyl group, Cl substituent, and R_10 group, with X_1=X_2 bond]

| Example No. | $X_1{=}{=}{=}X_2$ | $R_{10}$ | Compound name | [M + H] | HPLC Ret Time (min) |
|---|---|---|---|---|---|
| 85 | (single bond) | 2-formylphenyl (CHO) | 5-Acetyl-2-chloro-8-(2-formylphenyl)-5,6,11,12-tetrahydrodibenz[b,f]azocine | 389.80 | 3.947 |
| 86 | (single bond) | 2-acetylphenyl | 5-Acetyl-8-(2-acetylphenyl)-2-chloro-5,6,11,12-tetrahydrodibenz[b,f]azocine | 404.18 | 3.877 |

Examples 87 to 105

The following compounds in Table 3 have been synthesized utilizing the procedures described in Examples 2-5, starting from Example 15.

TABLE 3

[Structure: dibenzazocine core with N-acetyl group and R_10 group, with X_1=X_2 bond]

| Example No. | $X_1{=}{=}{=}X_2$ | $R_{10}$ | Compound name | [M + H] | HPLC Ret Time (min) |
|---|---|---|---|---|---|
| 87 | (double bond) | 2-(methoxycarbonyl)phenyl | 2-(5-Acetyl-5,6-dihydrodibenz[b,f]azocin-8-yl)benzoic acid, methyl ester | M—OMe = 352.07 | 3.800 |
| 88 | (double bond) | 2-acetamidophenyl | N-[2-(5-Acetyl-5,6-dihydrodibenz[b,f]azocin-8-yl)phenyl]acetamide | 383.13 | 3.463 |

TABLE 3-continued

| Example No. | X₁═X₂ | R₁₀ | Compound name | [M + H] | HPLC Ret Time (min) |
|---|---|---|---|---|---|
| 89 | (cis CH=CH) | 2-(methylsulfonylamino)phenyl | 5-Acetyl-5,6-dihydro-8-[2-[(methylsulfonyl)amino]-phenyl]dibenz[b,f]azocine | 419.07 | 3.493 |
| 90 | (cis CH=CH) | phenyl | 5-Acetyl-5,6-dihydro-8-phenyldibenz[b,f]azocine | 326.21 | 4.117 |
| 91 | (cis CH=CH) | 2-acetylphenyl | 5-Acetyl-8-(2-acetylphenyl)-5,6-dihydrodibenz[b,f]azocine | 368.18 | 3.750 |
| 92 | (cis CH=CH) | 2-methoxyphenyl | 5-Acetyl-5,6-dihydro-8-(2-methoxyphenyl)dibenz[b,f]azocine | 356.18 | 4.060 |
| 93 | (CH₂CH₂) | phenyl | 5-Acetyl-5,6,11,12-tetrahydro-8-phenyldibenz[b,f]azocine | 328.21 | 4.053 |
| 94 | (CH₂CH₂) | 4-pyridinyl | 5-Acetyl-5,6,11,12-tetrahydro-8-(4-pyridinyl)dibenz[b,f]azocine, trifluoroacetic acid salt (1:1) | 329.16 | 2.297 |
| 95 | (CH₂CH₂) | 4-(methylsulfonyl)phenyl | 5-Acetyl-5,6,11,12-tetrahydro-8-[4-(methylsulfonyl)phenyl]-dibenz[b,f]azocine | 406.11 | 3.363 |
| 96 | (CH₂CH₂) | 4-[2-(1-pyrrolidinyl)ethoxy]phenyl | 5-Acetyl-5,6,11,12-tetrahydro-8-[4-[2-(1-pyrrolidinyl)ethoxy]phenyl]-dibenz[b,f]azocine, trifluoroacetic acid salt (1:1) | 441.23 | 2.910 |

TABLE 3-continued

| Example No. | X₁====X₂ | R₁₀ | Compound name | [M + H] | HPLC Ret Time (min) |
|---|---|---|---|---|---|
| 97 | (cyclopentane) | 2-acetamidophenyl | N-[2-(5-Acetyl-5,6,11,12-tetrahydrodibenz[b,f]azocin-8-yl)phenyl]acetamide | 385.18 | 3.330 |
| 98 | (cyclopentane) | 2-(methoxycarbonyl)phenyl | 2-(5-Acetyl-5,6,11,12-tetrahydrodibenz[b,f]azocin-8-yl)benzoic acid, methyl ester | 386.16 | 3.757 |
| 99 | (cyclopentane) | 2-[(methylsulfonyl)amino]phenyl | 5-Acetyl-5,6,11,12-tetrahydro-8-[2-[(methylsulfonyl)amino]phenyl]dibenz[b,f]azocine | 421.21 | 3.363 |
| 100 | (cyclopentane) | 5-formyl-1-methyl-1H-imidazol-4-yl | 5-Acetyl-8-(5-formyl-1-methyl-1H-imidazol-4-yl)-5,6,11,12-tetrahydrodibenz[b,f]azocine | 360.16 | 2.857 |
| 101 | (cyclopentane) | 1-methyl-1H-imidazol-4-yl | 5-Acetyl-5,6,11,12-tetrahydro-8-(1-methyl-1H-imidazol-4-yl)dibenz[b,f]azocine | 332.13 | 2.270 |
| 102 | (cyclopentane) | 1-methyl-1H-imidazol-5-yl | 5-Acetyl-5,6,11,12-tetrahydro-8-(1-methyl-1H-imidazol-5-yl)dibenz[b,f]azocine | 332.13 | 2.930 |
| 103 | (cyclopentane) | phenyl | 5-Acetyl-5,6,11,12-tetrahydro-8-phenyldibenz[b,f]azocine | 328 | 4.05 |

TABLE 3-continued

| Example No. | X₁====X₂ | R₁₀ | Compound name | [M + H] | HPLC Ret Time (min) |
|---|---|---|---|---|---|
| 104 | (cyclopentene) | 2-acetylphenyl | 5-Acetyl-8-(2-acetylphenyl)-5,6,11,12-tetrahydrodibenz[b,f]azocine | 370.25 | 3.53 |
| 105 | (cyclopentene) | 2-methoxyphenyl | 5-Acetyl-5,6,11,12-tetrahydro-8-(2-methoxyphenyl)dibenz[b,f]-azocine | 358.16 | 3.970 |

Examples 106 to 126

The following compounds in Table 4 have been synthesized utilizing the procedures described in Examples 2-5, starting from Example 2.

TABLE 4

| Example No. | X₁====X₂ | R₁₁ | Compound name | [M + H] | HPLC Ret Time (min) |
|---|---|---|---|---|---|
| 106 | (cis-alkene) | 6-methoxy-3-pyridinyl | 5-Acetyl-5,6-dihydro-9-(6-methoxy-3-pyridinyl)dibenz[b,f]azocine | 357 | 1.78(b) |
| 107 | (cis-alkene) | 6-[2-(1-pyrrolidinyl)ethoxy]-2-pyridinyl | 5-Acetyl-5,6-dihydro-9-[6-[2-(1-pyrrolidinyl)ethoxy]-2-pyridinyl]dibenz[b,f]azocine | 440 | 2.73 |
| 108 | (cis-alkene) | 6-(methoxycarbonyl)-2-pyridinyl | 6-(5-Acetyl-5,6-dihydrodibenz[b,f]azocin-9-yl)-2-pyridinecarboxylic acid, methyl ester | 385 | 3.47 |

TABLE 4-continued

| Example No. | $X_1=X_2$ | $R_{11}$ | Compound name | [M + H] | HPLC Ret Time (min) |
|---|---|---|---|---|---|
| 109 | (double bond) | 6-[3-(dimethylamino)propoxy]-2-pyridinyl | 5-Acetyl-9-[6-[3-(dimethylamino)propoxy]-2-pyridinyl]-5,6-dihydrodibenz[b,f]azocine | 428 | 2.88 |
| 110 | (double bond) | 6-[4-(dimethylamino)butoxy]-2-pyridinyl | 5-Acetyl-9-[6-[4-(dimethylamino)butoxy]-2-pyridinyl]-5,6-dihydrodibenz[b,f]azocine | 442 | 2.99 |
| 111 | (double bond) | 6-(N-methylcarboxamide)-2-pyridinyl | 6-(5-Acetyl-5,6-dihydrodibenz[b,f]azocin-9-yl)-N-methyl-2-pyridinecarboxamide | 384 | 3.44 |
| 112 | (single bond) | 6-methoxy-3-pyridinyl | 5-Acetyl-5,6,11,12-tetrahydro-9-(6-methoxy-3-pyridinyl)dibenz[b,f]azocine | 359 | 1.68(b) |
| 113 | (single bond) | 6-[2-(1-pyrrolidinyl)ethoxy]-2-pyridinyl | 5-Acetyl-5,6,11,12-tetrahydro-9-[6-[2-(1-pyrrolidinyl)ethoxy]-2-pyridinyl]dibenz[b,f]azocine | 442 | 2.73(b) |
| 114 | (single bond) | 6-amino-2-pyridinyl | 5-Acetyl-9-(6-amino-2-pyridinyl)-5,6,11,12-tetrahydrodibenz[b,f]azocine | 344 | 1.56(b) |
| 115 | (single bond) | 6-(methoxycarbonyl)-2-pyridinyl | 6-(5-Acetyl-5,6,11,12-tetrahydrodibenz[b,f]azocin-9-yl)-2-pyridinecarboxylic acid, methyl ester | 387 | 3.46 |
| 116 | (single bond) | 6-[3-(dimethylamino)propoxy]-2-pyridinyl | 5-Acetyl-9-[6-[3-(dimethylamino)propoxy]-2-pyridinyl]-5,6,11,12-tetrahydrodibenz[b,f]azocine | 430 | 2.76 |

TABLE 4-continued

| Example No. | X₁═══X₂ | R₁₁ | Compound name | [M + H] | HPLC Ret Time (min) |
|---|---|---|---|---|---|
| 117 | | 6-[4-(dimethylamino)butoxy]-2-pyridinyl | 5-Acetyl-9-[6-[4-(dimethylamino)butoxy]-2-pyridinyl]-5,6,11,12-tetrahydrodibenz[b,f]azocine | 444 | 2.9 |
| 118 | | N-methyl-2-pyridinecarboxamide | 6-(5-Acetyl-5,6,11,12-tetrahydrodibenz[b,f]azocin-9-yl)-N-methyl-2-pyridinecarboxamide | 386 | 3.44 |
| 119 | | 6-methoxy-2-pyridinyl | 5-Acetyl-5,6,11,12-tetrahydro-9-(6-methoxy-2-pyridinyl)dibenz[b,f]azocine | 359 | 1.94(b) |
| 120 | | 2-pyridinyl | 5-Acetyl-5,6,11,12-tetrahydro-9-(2-pyridinyl)dibenz[b,f]azocine | 329 | 2.48(b) |
| 121 | | 2-[(methylsulfonyl)amino]phenyl | 5-Acetyl-5,6,11,12-tetrahydro-9-[2-[(methylsulfonyl)amino]phenyl]dibenz[b,f]azocine | 421 | 3.33 |
| 122 | | 4-[2-(1-pyrrolidinyl)ethoxy]phenyl | 5-Acetyl-5,6,11,12-tetrahydro-9-[4-[2-(1-pyrrolidinyl)ethoxy]phenyl]dibenz[b,f]azocine, trifluoroacetic acid salt (1:1) | 441 | 2.78 |
| 123 | | 4-carbamoylphenyl | 4-(5-Acetyl-5,6,11,12-tetrahydrodibenz[b,f]azocin-9-yl)benzamide | 371 | 3.19 |

TABLE 4-continued

| Example No. | X₁====X₂ | R₁₁ | Compound name | [M + H] | HPLC Ret Time (min) |
|---|---|---|---|---|---|
| 124 | (single bond) | 7-amino-2,1,3-benzoxadiazol-4-yl | 5-Acetyl-9-(7-amino-2,1,3-benzoxadiazol-4-yl)-5,6,11,12-tetrahydrodibenz[b,f]azocine | 385 | 3.65 |
| 125 | (single bond) | 4-pyridinyl | 5-Acetyl-5,6,11,12-tetrahydro-9-(4-pyridinyl)dibenz[b,f]azocine, trifluoroacetic acid salt (1:1) | 329 | 2.19 |
| 126 | (double bond) | 6-methoxy-2-pyridinyl | 5-Acetyl-5,6-dihydro-9-(6-methoxy-2-pyridinyl)dibenz[b,f]azocine | 357 | 3.48(d) |

Examples 127 to 179

The following compounds in Table 5 have been synthesized utilizing the procedures described in Examples 2-5, starting from Example 3.

TABLE 5

| Example No. | X₁====X₂ | R₁₁ | Compound name | [M + H] | HPLC Ret Time (min) |
|---|---|---|---|---|---|
| 127 | (double bond) | 4-(dimethylamino)phenyl | 5-Acetyl-2-chloro-9-[4-(dimethylamino)phenyl]-5,6-dihydrodibenz[b,f]azocine | 403 | 1.64(b) |

TABLE 5-continued

| Example No. | X₁═X₂ | R₁₁ | Compound name | [M + H] | HPLC Ret Time (min) |
|---|---|---|---|---|---|
| 128 | (cis-CH=CH) | 4-MeO-C₆H₄ | 5-Acetyl-2-chloro-5,6-dihydro-9-(4-methoxyphenyl)dibenz[b,f]azocine | 391 | 2.23(b) |
| 129 | (cis-CH=CH) | 2-MeO-C₆H₄ | 5-Acetyl-2-chloro-5,6-dihydro-9-(2-methoxyphenyl)dibenz[b,f]azocine | 391 | 2.27(b) |
| 130 | (cis-CH=CH) | 3-MeO-C₆H₄ | 5-Acetyl-2-chloro-5,6-dihydro-9-(3-methoxyphenyl)dibenz[b,f]azocine | 391 | 2.33(b) |
| 131 | (cis-CH=CH) | phenyl | 5-Acetyl-2-chloro-5,6-dihydro-9-phenyldibenz[b,f]azocine | 361 | 2.37(b) |
| 132 | (cis-CH=CH) | 3,5-dimethyl-4-isoxazolyl | 5-Acetyl-2-chloro-9-(3,5-dimethyl-4-isoxazolyl)-5,6-dihydrodibenz[b,f]azocine | 379 | 1.77(b) |
| 133 | (CH₂CH₂) | phenyl | 5-Acetyl-2-chloro-5,6,11,12-tetrahydro-9-phenyldibenz[b,f]azocine | 362 | 2.25(b) |
| 134 | (CH₂CH₂) | 4-(NMe₂)-C₆H₄ | 5-Acetyl-2-chloro-9-[4-(dimethylamino)phenyl]-5,6,11,12-tetrahydrodibenz[b,f]azocine, trifluoroacetic acid salt (1:1) | 405 | 1.34(b) |
| 135 | (CH₂CH₂) | 4-MeO-C₆H₄ | 5-Acetyl-2-chloro-5,6,11,12-tetrahydro-9-(4-methoxyphenyl)dibenz[b,f]azocine | 393 | 2.05(b) |

TABLE 5-continued

| Example No. | X₁=X₂ | R₁₁ | Compound name | [M + H] | HPLC Ret Time (min) |
|---|---|---|---|---|---|
| 136 | (single bond) | 2-OMe phenyl | 5-Acetyl-2-chloro-5,6,11,12-tetrahydro-9-(2-methoxyphenyl)dibenz[b,f]azocine | 393 | 2.17(b) |
| 137 | (single bond) | 3-OMe phenyl | 5-Acetyl-2-chloro-5,6,11,12-tetrahydro-9-(3-methoxyphenyl)dibenz[b,f]azocine | 393 | 2.22(b) |
| 138 | (double bond) | 4-CN phenyl | 5-Acetyl-2-chloro-9-(4-cyanophenyl)-5,6-dihydrodibenz[b,f]azocine | 385 | 1.98(b) |
| 139 | (double bond) | 4-pyridinyl | 5-Acetyl-2-chloro-5,6-dihydro-9-(4-pyridinyl)dibenz[b,f]azocine, trifluoroacetic acid salt (1:1) | 361 | 1.71(b) |
| 140 | (double bond) | 6-methyl-2-pyridinyl | 5-Acetyl-2-chloro-5,6-dihydro-9-(6-methyl-2-pyridinyl)dibenz[b,f]azocine, trifluoroacetic acid salt (1:1) | 375 | 0.79(b) |
| 141 | (double bond) | 4-(methylsulfonyl)phenyl | 5-Acetyl-2-chloro-5,6-dihydro-9-[4-(methylsulfonyl)phenyl]dibenz[b,f]-azocine | 438 | 1.607(b) |
| 142 | (double bond) | 6-methoxy-3-pyridinyl | 5-Acetyl-2-chloro-5,6-dihydro-9-(6-methoxy-3-pyridinyl)dibenz[b,f]azocine, trifluoroacetic acid salt (1:1) | 391 | 2.07(b) |
| 143 | (single bond) | 5-(2-methyl-4-thiazolyl)-2-thienyl | 5-Acetyl-2-chloro-5,6,11,12-tetrahydro-9-[5-(2-methyl-4-thiazolyl)-2-thienyl]dibenz[b,f]azocine | 465 | 4.27 |

TABLE 5-continued

| Example No. | X$_1$====X$_2$ | R$_{11}$ | Compound name | [M + H] | HPLC Ret Time (min) |
|---|---|---|---|---|---|
| 144 | | 3-thienyl | 5-Acetyl-2-chloro-5,6,11,12-tetrahydro-9-(3-thienyl)dibenz[b,f]azocine | 368 | 4.103 |
| 145 | | 3-(NHC(O)Me)phenyl | N-[3-(5-Acetyl-2-chloro-5,6,11,12-tetrahydrodibenz[b,f]azocin-9-yl)phenyl]acetamide | 419 | 3.69 |
| 146 | | 4-(NHC(O)Me)phenyl | N-[4-(5-Acetyl-2-chloro-5,6,11,12-tetrahydrodibenz[b,f]azocin-9-yl)phenyl]acetamide | 419 | 3.63 |
| 147 | | 4-(CO$_2$Me)phenyl | 4-(5-Acetyl-2-chloro-5,6,11,12-tetrahydrodibenz[b,f]azocin-9-yl)benzoic acid, methyl ester | 420 | 4.15 |
| 148 | | 3-(CO$_2$Me)phenyl | 3-(5-Acetyl-2-chloro-5,6,11,12-tetrahydrodibenz[b,f]azocin-9-yl)benzoic acid, methyl ester | 420 | 4.16 |
| 149 | | 2-(CO$_2$Me)phenyl | 2-(5-Acetyl-2-chloro-5,6,11,12-tetrahydrodibenz[b,f]azocin-9-yl)benzoic acid, methyl ester | 420 | 3.96 |

TABLE 5-continued

| Example No. | X₁═X₂ | R₁₁ | Compound name | [M + H] | HPLC Ret Time (min) |
|---|---|---|---|---|---|
| 150 | 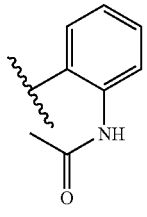 | 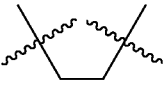 | N-[2-(5-Acetyl-2-chloro-5,6,11,12-tetrahydrodibenz[b,f]azocin-9-yl)phenyl]acetamide | 419 | 3.487 |
| 151 | 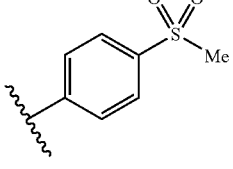 | 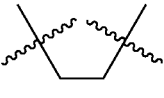 | 5-Acetyl-2-chloro-5,6,11,12-tetrahydro-9-[4-(methylsulfonyl)phenyl]dibenz[b,f]-azocine | 440 | 3.47 |
| 152 | 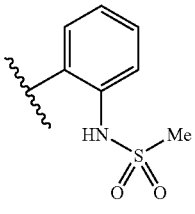 |  | 5-Acetyl-2-chloro-5,6,11,12-tetrahydro-9-[2-[(methylsulfonyl)amino]phenyl]-dibenz[b,f]azocine | 455 | 3.507 |
| 153 | 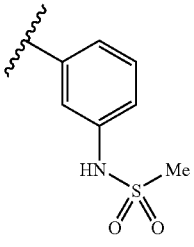 | 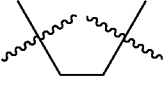 | 5-Acetyl-2-chloro-5,6,11,12-tetrahydro-9-[3-[(methylsulfonyl)amino]phenyl]-dibenz[b,f]azocine | 455 | 3.61 |
| 154 | 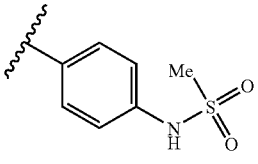 | 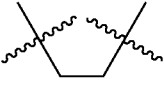 | 5-Acetyl-2-chloro-5,6,11,12-tetrahydro-9-[4-[(methylsulfonyl)amino]phenyl]-dibenz[b,f]azocine | 455 | 3.55 |
| 155 | | 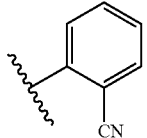 | 5-Acetyl-2-chloro-9-(2-cyanophenyl)-5,6,11,12-tetrahydrodibenz[b,f]azocine | 387 | 3.81 |

TABLE 5-continued

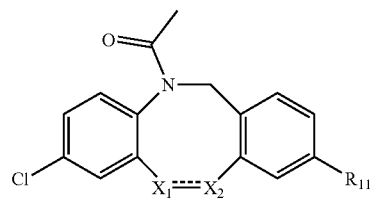

| Example No. | $X_1$═$X_2$ | $R_{11}$ | Compound name | [M + H] | HPLC Ret Time (min) |
|---|---|---|---|---|---|
| 156 | | | 5-Acetyl-2-chloro-9-(2-cyanophenyl)-5,6,11,12-tetrahydrodibenz[b,f]azocine | 387 | 3.90 |
| 157 | | | 5-Acetyl-2-chloro-9-(4-cyanophenyl)-5,6,11,12-tetrahydrodibenz[b,f]azocine | 387 | 3.87 |
| 158 | | | 5-Acetyl-2-chloro-5,6,11,12-tetrahydro-9-(4-pyridinyl)dibenz[b,f]azocine, trifluoroacetic acid salt (1:1) | 363 | 1.64(b) |
| 159 | | | 5-Acetyl-2-chloro-5,6,11,12-tetrahydro-9-(3-pyridinyl)dibenz[b,f]azocine, trifluoroacetic acid salt (1:1) | 363 | 1.71(b) |
| 160 | | | 5-Acetyl-2-chloro-5,6,11,12-tetrahydro-9-(2-pyridinyl)dibenz[b,f]azocine | 363 | 1.79(b) |
| 161 | | | 5-Acetyl-2-chloro-5,6,11,12-tetrahydro-9-[4-[2-(1-pyrrolidinyl)ethoxy]phenyl]dibenz[b,f]azocine, trifluoroacetic acid salt (1:1) | 476 | 2.97 |
| 162 | | | 5-Acetyl-9-[3-(aminosulfonyl)phenyl]-2-chloro-5,6,11,12-tetrahydrodibenz[b,f]azocine | 441 | 1.32(b) |
| 163 | | | 5-Acetyl-9-[4-(aminosulfonyl)phenyl]-2-chloro-5,6,11,12-tetrahydrodibenz[b,f]azocine | 441 | 1.26(b) |

TABLE 5-continued

| Example No. | X₁═══X₂ | R₁₁ | Compound name | [M + H] | HPLC Ret Time (min) |
|---|---|---|---|---|---|
| 164 | (single bond) | 2-carbamoylphenyl | 2-(5-Acetyl-2-chloro-5,6,11,12-tetrahydrodibenz[b,f]azocin-9-yl)benzamide | 405 | 1.35(b) |
| 165 | (single bond) | 4-carbamoylphenyl | 4-(5-Acetyl-2-chloro-5,6,11,12-tetrahydrodibenz[b,f]azocin-9-yl)benzamide | 405 | 1.39(b) |
| 166 | (single bond) | 6-methyl-2-pyridinyl | 5-Acetyl-2-chloro-5,6,11,12-tetrahydro-9-(6-methyl-2-pyridinyl)dibenz[b,f]azocine, trifluoroacetic acid salt (1:1) | 377 | 0.59(b) |
| 167 | (single bond) | 5-carbamoyl-3-pyridinyl | 5-(5-Acetyl-2-chloro-5,6,11,12-tetrahydrodibenz[b,f]azocin-9-yl)-3-pyridinecarboxamide, trifluoroacetic acid salt (1:1) | 406 | 0.74(b) |
| 168 | (single bond) | 4-methyl-2-pyridinyl | 5-Acetyl-2-chloro-5,6,11,12-tetrahydro-9-(4-methyl-2-pyridinyl)dibenz[b,f]azocine, trifluoroacetic acid salt (1:1) | 377 | 1.06(b) |
| 169 | (single bond) | 2-[2-(1-pyrrolidinyl)ethoxy]phenyl | 5-Acetyl-2-chloro-5,6,11,12-tetrahydro-9-[2-[2-(1-pyrrolidinyl)ethoxy]phenyl]dibenz[b,f]-azocine, trifluoroacetic acid salt (1:1) | 476 | 1.13(b) |
| 170 | (single bond) | 3-furanyl | 5-Acetyl-2-chloro-9-(3-furanyl)-5,6,11,12-tetrahydrodibenz[b,f]azocine | 352 | 1.90(b) |
| 171 | (single bond) | 3-[2-(1-pyrrolidinyl)ethoxy]phenyl | 5-Acetyl-2-chloro-5,6,11,12-tetrahydro-9-[3-[2-(1-pyrrolidinyl)ethoxy]phenyl]dibenz-[b,f]azocine | 476 | 1.053(b) |

TABLE 5-continued

| Example No. | X₁===X₂ | R₁₁ | Compound name | [M + H] | HPLC Ret Time (min) |
|---|---|---|---|---|---|
| 172 | | 5-pyridinyl, 2-OMe | 5-Acetyl-2-chloro-5,6,11,12-tetrahydro-9-(6-methoxy-3-pyridinyl)dibenz[b,f]azocine, trifluoroacetic acid salt (1:1) | 393 | 2.813(b) |
| 173 | | 2-pyridinyl, 5-CF₃ | 5-Acetyl-2-chloro-5,6,11,12-tetrahydro-9-[5-(trifluoromethyl)-2-pyridinyl]dibenz[b,f]azocine, trifluoroacetic acid salt (1:1) | 431 | 2.12(b) |
| 174 | | 4-fluorophenyl | 5-Acetyl-2-chloro-9-(4-fluorophenyl)-5,6,11,12-tetrahydrodibenz[b,f]azocine | 380 | 2.217(b) |
| 175 | | 5-pyrimidinyl | 5-Acetyl-2-chloro-5,6,11,12-tetrahydro-9-(5-pyrimidinyl)dibenz[b,f]azocine | 364 | 1.31(b) |
| 176 | | 1,3,5-trimethyl-1H-pyrazol-4-yl | 5-Acetyl-2-chloro-5,6,11,12-tetrahydro-9-(1,3,5-trimethyl-1H-pyrazol-4-yl)dibenz[b,f]azocine | 394 | 1.52(b) |
| 177 | | 2-thienyl | 5-Acetyl-2-chloro-5,6,11,12-tetrahydro-9-(2-thienyl)dibenz[b,f]azocine | 368 | 2.18(b) |
| 178 | CH=CH | 2-acetylphenyl | 5-Acetyl-9-(2-acetylphenyl)-2-chloro-5,6-dihydro-dibenz[b,f]azocine | 402 | 3.61 |

TABLE 5-continued

| Example No. | $X_1$====$X_2$ | $R_{11}$ | Compound name | [M + H] | HPLC Ret Time (min) |
|---|---|---|---|---|---|
| 179 | (double bond) | 3-acetylphenyl | 5-Acetyl-9-(3-acetylphenyl)-2-chloro-5,6-dihydro-dibenz[b,f]azocine | 402 | 3.76 |

Examples 180 to 184

The following compounds in Table 6 have been synthesized utilizing the procedures described in Examples 2-5, starting from Example 18.

TABLE 6

| Example No. | $X_1$====$X_2$ | $R_{10}$ | Compound name | [M + H] | HPLC Ret Time (min) |
|---|---|---|---|---|---|
| 180 | (double bond) | phenyl | 5-Acetyl-2-chloro-5,6-dihydro-9-methoxy-8-phenyldibenz[b,f]azocine | 390.22 | 2.360(a) |
| 181 | (double bond) | 4-pyridinyl | 5-Acetyl-2-chloro-5,6-dihydro-9-methoxy-8-(4-pyridinyl)dibenz[b,f]azocine, trifluoroacetic acid salt (1:1) | 391.23 | 2.757 |
| 182 | (double bond) | 2-acetylphenyl | 5-Acetyl-8-(2-acetylphenyl)-2-chloro-5,6-dihydro-9-methoxydibenz[b,f]azocine | 432.44 | 2.267(b) |

TABLE 6-continued

| Example No. | X₁====X₂ | R₁₀ | Compound name | [M + H] | HPLC Ret Time (min) |
|---|---|---|---|---|---|
| 183 | (cyclohexene-like bridge) | 4-pyridinyl | 5-Acetyl-2-chloro-5,6,11,12-tetrahydro-9-methoxy-8-(4-pyridinyl)dibenz[b,f]azocine, trifluoroacetic acid salt (1:1) | 393.19 | 2.540 |
| 184 | (cyclohexene-like bridge) | phenyl | 5-Acetyl-2-chloro-5,6,11,12-tetrahydro-9-methoxy-8-phenyldibenz[b,f]azocine | 392 | 2.07(b) |

Examples 185 to 186

The following compounds in Table 7 have been synthesized utilizing the procedures described in Examples 2-5, starting from Example 20.

TABLE 7

| Example No. | R₁₀ | Compound name | [M + H] | HPLC Ret Time (min) |
|---|---|---|---|---|
| 185 | phenyl | 5-Acetyl-3-chloro-5,6-dihydro-9-methoxy-8-phenyl-dibenz[b,f]azocine | 390 | 2.46(b) |
| 186 | 2-acetylphenyl | 5-Acetyl-8-(2-acetylphenyl)-3-chloro-5,6-dihydro-9-methoxy-dibenz[b,f]azocine | 432 | 2.25(b) |

Examples 187 to 189

The following compounds in Table 8 have been synthesized utilizing the procedures described in Examples 2-5, starting from Example 11.

TABLE 8

[Structure: 5-acetyl-3-chloro-9-fluoro-5,6-dihydro-dibenz[b,f]azocine core with R$_{10}$ substituent]

| Example No. | R$_{10}$ | Compound name | [M + H] | HPLC Ret Time (min) |
|---|---|---|---|---|
| 187 | phenyl | 5-Acetyl-3-chloro-9-fluoro-5,6-dihydro-8-phenyl-dibenz[b,f]azocine | 378 | 3.72(c) |
| 188 | 2-acetylphenyl | 5-Acetyl-8-(2-acetylphenyl)-3-chloro-9-fluoro-5,6-dihydro-dibenz[b,f]azocine | 420 | 3.33(c) |
| 189 | 2-(N-methylcarbamoyl)phenyl | 2-(5-Acetyl-3-chloro-9-fluoro-5,6-dihydrodibenz[b,f]azocin-8-yl)-N-methyl-benzamide | 435 | 2.99(c) |

Examples 190 to 192

The following compounds in Table 9 have been synthesized utilizing the procedures described in Examples 2-5, starting from Example 14.

TABLE 9

[Structure: 5-acetyl-9-fluoro-3-nitro-5,6-dihydro-dibenz[b,f]azocine core with X$_1$=X$_2$ and R$_{10}$ substituents]

| Example No. | X$_1$═X$_2$ | R$_{10}$ | Compound name | [M + H] | HPLC Ret Time (min) |
|---|---|---|---|---|---|
| 190 | CH=CH | phenyl | 5-Acetyl-9-fluoro-5,6-dihydro-3-nitro-8-phenyl-dibenz[b,f]azocine | 389 | 3.70 |

TABLE 9-continued

| Example No. | X₁===X₂ | R₁₀ | Compound name | [M + H] | HPLC Ret Time (min) |
|---|---|---|---|---|---|
| 191 | (cis-CH=CH) | 2-acetylphenyl | 5-Acetyl-8-(2-Acetylphenyl)-9-fluoro-5,6-dihydro-3-nitro-dibenz[b,f]azocine | 431 | 3.25 |
| 192 | (cis-CH=CH) | 2-(N-methylcarbamoyl)phenyl | 2-(5-Acetyl-9-fluoro-5,6-dihydro-3-nitrodibenz[b,f]azocin-8-yl)-N-methyl-benzamide | 446 | 2.88 |

Examples 193 to 194

The following compounds in Table 10 have been synthesized utilizing the procedures described in Examples 2-5, starting from Example 13.

TABLE 10

| Example No. | X₁===X₂ | R₁₀ | Compound name | [M + H] | HPLC Ret Time (min) |
|---|---|---|---|---|---|
| 193 | (cis-CH=CH) | phenyl | 5-Acetyl-8-phenyl-5,6-dihydro-3-nitro-dibenz[b,f]azocine | 371 | 3.69 |
| 194 | (cis-CH=CH) | 2-acetylphenyl | 5-Acetyl-8-(2-acetylphenyl)-5,6-dihydro-3-nitro-dibenz[b,f]azocine | 413 | 3.31 |

Examples 195 to 196

The following compounds in Table 11 have been synthesized utilizing the procedures described in Examples 2-5, starting from Example 5.

TABLE 11

| Example No. | $X_1$---$X_2$ | $R_{10}$ | Compound name | [M + H] | HPLC Ret Time (min) |
|---|---|---|---|---|---|
| 195 | | | 5-Acetyl-8-(2-acetylphenyl)-3-chloro-5,6-dihydrodibenz[b,f]azocine | 402 | 3.63 |
| 196 | | | 2-(5-Acetyl-3-chloro-5,6-dihydrodibenz[b,f]azocin-8-yl)-N-methyl-benzamide | 439 (M + Na) | 3.23 |

Examples 197 to 199

The following compounds in Table 12 have been synthesized utilizing the procedures described in Examples 2-5, starting from Example 9.

TABLE 12

| Example No. | $X_1$---$X_2$ | $R_{10}$ | Compound name | [M + H] | HPLC Ret Time (min) |
|---|---|---|---|---|---|
| 197 | | | 5-Acetyl-9-fluoro-5,6-dihydro-8-phenyl-dibenz[b,f]azocine | 344 | 3.54(c) |
| 198 | | | 5-Acetyl-8-(2-acetylphenyl)-9-fluoro-5,6-dihydro-dibenz[b,f]azocine | 386 | 3.15(c) |

TABLE 12-continued

| Example No. | X₁═X₂ | R₁₀ | Compound name | [M + H] | HPLC Ret Time (min) |
|---|---|---|---|---|---|
| 199 | (cyclopentene-like fragment) | 2-acetylphenyl with MeHN-C(O)- | 2-(5-Acetyl-9-fluoro-5,6-dihydrodibenz[b,f]azocin-8-yl)-N-methyl-benzamide | 401 | 2.77(c) |

Examples 200 to 202

The following compounds in Table 13 have been synthesized utilizing the procedures described in Examples 2-5, starting from Example 11.

TABLE 13

| Example No. | R₁₀ | Compound name | [M + H] | HPLC Ret Time (min) |
|---|---|---|---|---|
| 200 | phenyl | 5-Acetyl-2-chloro-9-fluoro-5,6-dihydro-8-phenyl-dibenz[b,f]azocine | 344 | 3.52(c) |
| 201 | 2-acetylphenyl | 5-Acetyl-8-(2-acetylphenyl)-2-chloro-9-fluoro-5,6-dihydro-dibenz[b,f]azocine | 420 | 3.39(c) |
| 202 | 2-(N-methylcarbamoyl)phenyl | 2-(5-Acetyl-2-chloro-9-fluoro-5,6-dihydro-dibenz[b,f]azocin-8-yl)-N-methyl-benzamide | 435 | 3.05(c) |

Examples 203 to 205

The following compounds in Table 14 have been synthesized utilizing the procedures described in Examples 2-5, starting from Example 6, 7, or 8.

TABLE 14

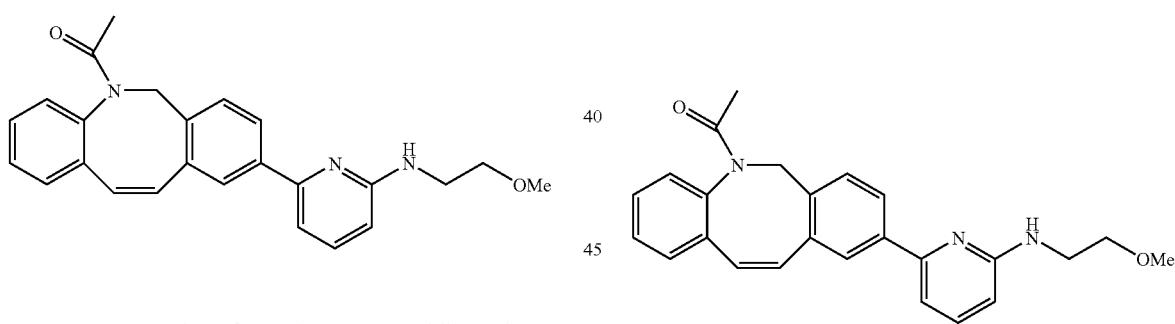

| Example No. | R₆ | Compound name | [M + H] | HPLC Ret Time (min) |
|---|---|---|---|---|
| 203 | H | 5-Acetyl-8-fluoro-5,6-dihydro-9-(6-methoxy-3-pyridinyl)-dibenz[b,f]azocine | 375 | 3.28(c) |
| 204 | 2-Cl | 5-Acetyl-2-chloro-8-fluoro-5,6-dihydro-9-(6-methoxy-3-pyridinyl)-dibenz[b,f]azocine | 409 | 3.55(c) |
| 205 | 3-Cl | 5-Acetyl-3-chloro-8-fluoro-5,6-dihydro-9-(6-methoxy-3-pyridinyl)-dibenz[b,f]azocine | 409 | 3.51(c) |

Example 206

5-Acetyl-5,6-dihydro-9-[6-[(2-methoxyethyl)amino]-2-pyridinyl]-dibenz[b,f]azocine

206A. Preparation of 1-[9-(6-Bromo-pyridin-2-yl)-6H-dibenzo[b,f]azocin-5-yl]-ethanone

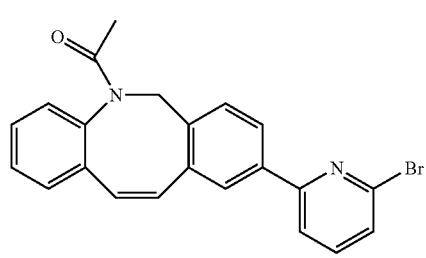

A 2 mL conical vial was charged with 1-[9-(4,4,5,5-Tetramethyl-[1,3,2]dioxaborolan-2-yl)-6H-dibenzo[b,f]azocin-5-yl]-ethanone (prepared by the method described in Example 2A starting with 2)(30 mg, 0.08 mmol), 2,6-Dibromo-pyridine (39 mg, 0.18 mmol) and Pd(PPh₃)₄ (9 mg). The vial was evacuated and purged with argon. EtOH (0.5 mL) and toluene (0.5 mL) were added, followed by 2M aqueous Na₂CO₃ (0.036 mL, 0.072 mmol). The reaction was heated to 80° C. until disappearance of the starting material was noted. The reaction was cooled to room temperature and concentrated. The product was purified by reversed-phase HPLC to afford Example 206A (18.5 mg, 60%).

Example 206

A mixture of Example 206A (20 mg, 0.05 mmol), BINAP (6 mg, 0.009 mmol), t-BuONa (12 mg, 0.12 mmol) and 2-methoxy-ethylamine (0.25 mmol) in toluene (2 mL) was purged with argon, then heated at 110° C. for 2 hours. The reaction mixture was cooled to room temperature, concentrated and purified by preparative reversed-phase HPLC to give the title compound (5.3 mg, 27%). HPLC R$_t$=2.54 min. m/z=400 (M+H⁺)

Examples 207 to 208

The following compounds in Table 15 have been synthesized from Example 206A using the procedures described in Example 206, utilizing the appropriate starting materials.

TABLE 15

| Example No. | R₁₁ | Compound name | [M + H] | HPLC Ret Time (min) |
|---|---|---|---|---|
| 207 | | 5-Acetyl-5,6-dihydro-9-[6-(4-methyl-1-piperazinyl)-2-pyridinyl]dibenz[b,f]azocine | 425 | 0.81 |
| 208 | | 5-Acetyl-5,6-dihydro-9-[6-(4-morpholinyl)-2-pyridinyl]dibenz[b,f]azocine | 412 | 1.67 |

Example 209

5-Acetyl-5,6,11,12-tetrahydro-9-[6-[[2-(1-pyrrolidinyl)ethyl]amino]-2-pyridinyl]-dibenz[b,f]azocine Example 210

6-Acetyl-3-chloro-1a,6,7,11b-tetrahydro-10-phenyl-dibenz[b,f]oxireno[d]azocine

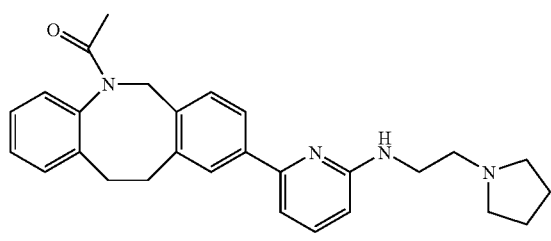

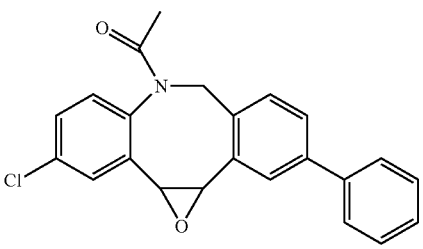

A mixture of 1-[9-(6-Bromo-pyridin-2-yl)-11,12-dihydro-6H-dibenzo[b,f]azocin-5-yl]-ethanone (prepared according to Example 14 and Example 195 starting from Example 2) (17 mg, 0.04 mmol), BINAP (5 mg, 0.008 mmol), t-BuONa (10 mg, 0.1 mmol) and N-(2-aminoethyl)pyrrolidine (6 µl, 0.05 mmol) in toluene (2 mL) was purged with argon, then heated at 95° C. for 1 h. The reaction mixture was cooled to room temperature, concentrated and purified by preparative reversed-phased HPLC to give the title compound (5.8 mg, 33%). HPLC $R_t$=1.52(b) min. m/z=441 (M+H⁺).

To a suspension of Example 131 (10 mg, 0.03 mmol) and NaHCO₃ (13 mg, 0.15 mmol) in CH₂Cl₂ (2 mL) was added mCPBA (12 mg, 0.06 mmol). The mixture was stirred overnight, then diluted with water (10 mL) and the layers were separated. The organic layer was washed with saturated NaHCO₃ (2×10 ML), H₂O (1×10 mL) and concentrated. Purification by radial chromatography (1 mm plate, 30% EtOAc/hexanes) afforded the desired product (3.0 mg, 30%). HPLC $R_t$=2.01(b) min. m/z=376 (M+H⁺).

Example 211

5-Acetyl-5,6,11,12-tetrahydro-9-(6-hydroxy-3-pyridinyl)-dibenz[b,f]azocine

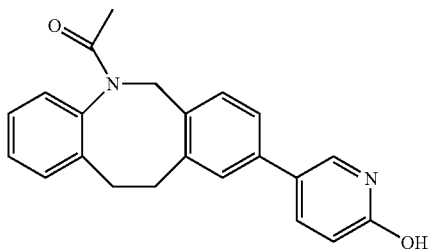

A mixture of Example 112 (15 mg, 0.042 mmol) and pyridine.HCl (100 mg, 0.84 mmol) in toluene (2 mL) was heated to 180° C. in a sealed pressure vial for 1 hour. The reaction mixture was cooled to room temperature, concentrated and purified by preparative reversed-phase HPLC to give the title compound (4.0 mg, 28%). HPLC $R_t$=0.91(b) min. m/z=345 (M+H$^+$).

Example 212

5-Acetyl-5,6,11,12-tetrahydro-9-(1-oxido-2-pyridinyl)-dibenz[b,f]azocine

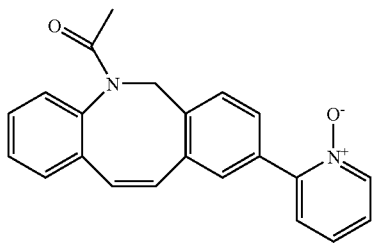

To a solution of Example 120 (15 mg, 0.046 mmol) in CH$_2$Cl$_2$ (1 mL) at 0° C. was added mCPBA (16 mg, 0.069 mmol). The mixture was stirred at room temperature for 4 hours. The resulting reaction mixture was concentrated and purified by radial chromatography (1 mm plate, 5% MeOH/CH$_2$Cl$_2$) to give the desired product (8.3 mg, 52%). HPLC $R_t$=1.78(b) min. m/z=345 (M+H$^+$).

Example 213

5-Acetyl-6,11-dihydro-9-(6-methoxy-3-pyridinyl)-dibenz[b,f]azocin-12(5H)-one

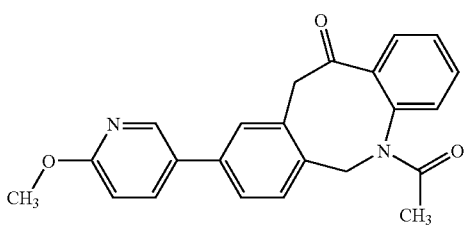

213A. Preparation of 9-Bromo-6,11-dihydro-5H-dibenzo[b,f]azocin-12-one

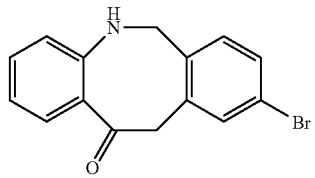

To a solution of 1-(9-Bromo-1 2-hydroxy-11,12-dihydro-6H-dibenzo[b,f]azocin-5-yl)-ethanone (prepared similar to Example 1E using the appropriate starting materials) (50 mg, 0.17 mmol) in MeOH (5 mL) was added MnO$_2$ (72 mg, 0.83 mmol). The mixture was stirred under argon for 36 hours, filtered, and the filtrate was concentrated. The resulting residue was dissolved in THF (5 mL), MnO$_2$ (144 mg, 1.66 mmol) was added, and the resulting mixture was stirred at room temperature overnight. The suspension was filtered, concentrated and purified by flash chromatography (SiO$_2$, 15% EtOAc/hexanes) to afford Example 213A (25 mg, 49%) as an off-white solid.

213B. Preparation of 5-Acetyl-9-bromo-6,11-dihydro-5H-dibenzo[b,f]azocin-12-one

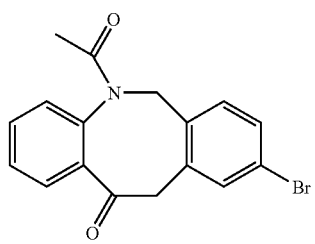

To a mixture of Example 213A (25 mg, 0.08 mmol) in toluene (1 mL) was added Ac$_2$O (13 mg, 0.12 mmol), Et$_3$N (17 μl, 0.12 mmol) and a catalytic amount of DMAP (1 mg). The mixture was heated to 90° C. for 2 hours. The resulting mixture was concentrated, and the residue was purified by flash chromatography (SiO$_2$, 20% to 40% EtOAc/hexanes) to afford Example 213B as a white solid (13 mg, 48%).

Example 213

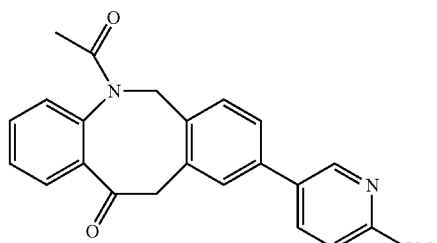

To a solution of Example 213B (10 mg, 0.03 mmol) in toluene (1 mL) was added a solution of 2-Methoxy-5-(4,4,5,5-tetramethyl-[1,3,2]dioxaborolan-2-yl)-pyridine (10 mg, 0.04 mmol) in EtOH (1 mL). The reaction mixture was purged with argon. Pd(PPh$_3$)$_4$ (3 mg, 0.003 mmol) and Na$_2$CO$_3$ (451, 2 M solution in H$_2$O, 0.09 mmol) were added. The mixture was heated to 80° C. for 5 hours, cooled to room temperature and concentrated. The residue was purified by flash chromatography (SiO$_2$, 40% to 50% EtOAc/hexanes) to afford the desired product (6.8 mg, 61%). HPLC R$_t$=2.09(b) min. m/z=373 (M+H$^+$).

Example 214

6-Acetyl-3-chloro-1a,6,7,11b-tetrahydro-10-(6-methoxy-3-pyridinyl)-dibenz[b,f]oxireno[d]azocine

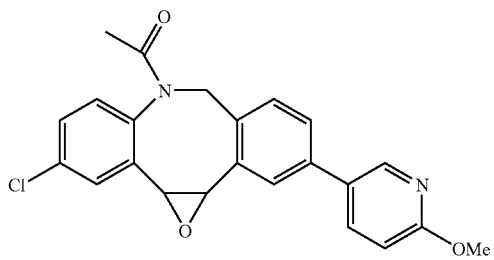

214A. Preparation of 6-Acetyl-3-chloro-1a,6,7,11b-tetrahydro-10-bromo-dibenz[b,f]oxireno[d]azocine

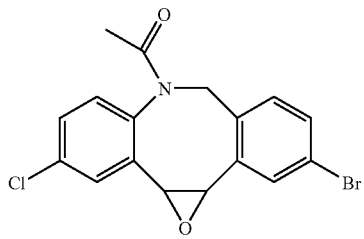

To a solution of Example 3 (500 mg, 1.39 mmol) in CH$_2$Cl$_2$ (10 mL) was added a solution of mCPBA (1.79 g, 8.4 mmol) in CH$_2$Cl$_2$ (10 mL). The mixture was heated to reflux overnight, cooled to room temperature, and poured into saturated NaHCO$_3$ (50 mL). The layers were separated, the organic layer was washed with saturated aqueous NaHCO$_3$ (2×50 mL), dried (Na$_2$SO$_4$), filtered and concentrated. The residue was purified by flash chromatography (SiO$_2$, 30% to 50% EtOAc/hexanes) to afford Example 214A as a white solid (205 mg, 39%).

Example 214

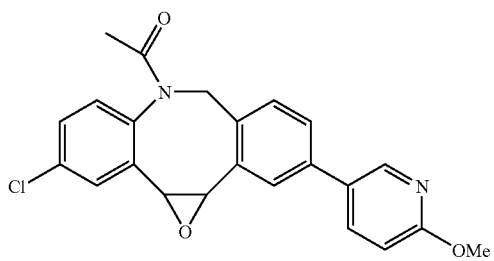

Compound Example 214 (12 mg, 56%) was prepared from Example 214A (20 mg, 0.053 mmol) and 2-Methoxy-5-(4,4, 5,5-tetramethyl-[1,3,2]dioxaborolan-2-yl)-pyridine (19 mg, 0.081 mmol) by a route similar to that used for the preparation of compound Example 213. HPLC R$_t$=2.23(b) min. m/z=407 (M+H$^+$).

Example 215

5-Acetyl-9-[2-(aminomethyl)phenyl]-2-chloro-5,6,11,12-tetrahydrodibenz[b,f]azocine

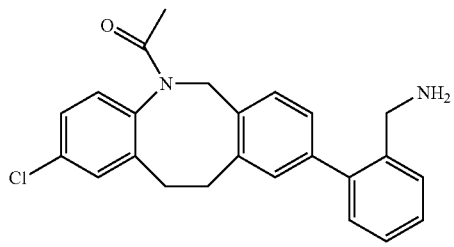

215A. Preparation of (2-Bromo-benzyl)-carbamic acid tert-butyl ester

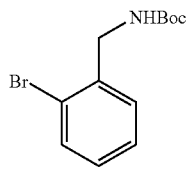

To a solution of 2-bromo-benzylamine hydrochloride (220 mg, 1.0 mmol) in CH$_2$Cl$_2$ (5 mL) was added DIEA (0.17 mL, 1 mmol) and DMAP (12 mg, 0.1 mmol), followed by a solution of Boc$_2$O (260 mg, 1.2 mmol) in CH$_2$Cl$_2$ (1.2 mL). The reaction mixture was stirred at room temperature for 2 hours, then diluted with CH$_2$Cl$_2$ (25 mL) and washed with H$_2$O (1×25 mL), 0.1 N HCl (2×25 mL) and saturated aqueous NaHCO$_3$ (2×25 mL), The organic layer was dried (Na$_2$SO$_4$), filtered and concentrated to give Example 215A (234 mg, 82%).

215B

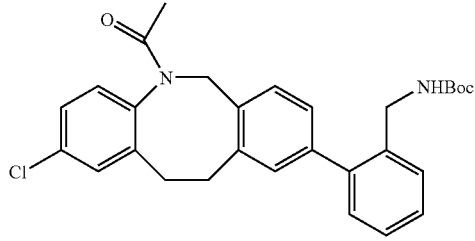

Compound Example 215B was prepared from Example 215A and Example 22B by a route analogous to that used for the preparation of Example 22.

Example 215

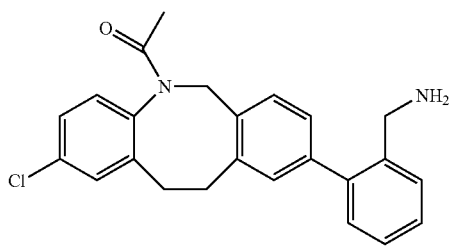

A solution of Example 215B in 4M HCl/dioxane (2 mL) was stirred at room temperature for 2 hours. After concentrating, the residue was purified by preparative reversed-phase HPLC to give the desired product as a TFA salt (4.4 mg, 47%) for two steps from 225A. HPLC $R_f$=0.96(b) min. m/z=391 (M+H$^+$)

Examples 216 to 221

The following compounds in Table 16 and Table 17 have been synthesized utilizing the procedures described in Example 215, utilizing the appropriate starting materials.

TABLE 16

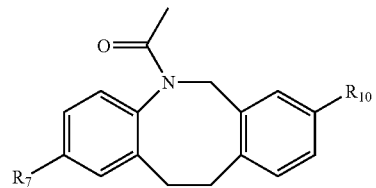

| Example No. | R$_7$ | R$_{10}$ | Compound name | [M + H] | HPLC Ret Time (min) |
|---|---|---|---|---|---|
| 216 | Cl | ![2-(aminomethyl)phenyl] | 5-Acetyl-8-[2-(aminomethyl)phenyl]-2-chloro-5,6,11,12-tetrahydrodibenz[b,f]azocine, trifluoroacetic acid salt (1:1) | 391.15 | 3.070 |
| 217 | Cl | ![3-(aminomethyl)phenyl] | 5-Acetyl-8-[3-(aminomethyl)phenyl]-2-chloro-5,6,11,12-tetrahydrodibenz[b,f]azocine, trifluoroacetic acid salt (1:1) | 391 | 3.017 |
| 218 | Cl | ![4-(aminomethyl)phenyl] | 5-Acetyl-8-[4-(aminomethyl)phenyl]-2-chloro-5,6,11,12-tetrahydrodibenz[b,f]azocine, trifluoroacetic acid salt (1:1) | 391.13 | 2.950 |
| 219 | H | ![2-(aminomethyl)phenyl] | 5-Acetyl-8-[2-(aminomethyl)phenyl]-5,6,11,12-tetrahydro-dibenz[b,f]azocine | 357.24 | 2.877 |

TABLE 17

[Structure: acetyl-N dibenz[b,f]azocine with Cl and R₁₁ substituents]

| Example No. | R₁₁ | Compound name | [M + H] | HPLC Ret Time (min) |
|---|---|---|---|---|
| 220 | [3-(aminomethyl)phenyl group] | 5-Acetyl-9-[3-(aminomethyl)phenyl]-2-chloro-5,6,11,12-tetrahydrodibenz[b,f]azocine, trifluoroacetic acid salt (1:1) | 391 | 0.887(b) |
| 221 | [4-(aminomethyl)phenyl group] | 5-Acetyl-9-[4-(aminomethyl)phenyl]-2-chloro-5,6,11,12-tetrahydrodibenz[b,f]azocine, trifluoroacetic acid salt (1:1) | 391 | 0.787(b) |

Example 222

2-(5-Acetyl-2-chloro-5,6-dihydro-dibenzo[b,f]azocin-8-yl)-benzoic acid

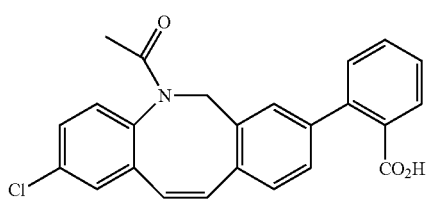

To a solution of Example 34 (235 mg, 0.56 mmol) in a mixed solvent of THF (10 mL) and MeOH (4 mL) was added a solution of LiOH·H₂O (95 mg, 2.25 mmol) in H₂O (2 mL). The reaction mixture was stirred at 40° C. overnight. After cooling to room temperature, the mixture was concentrated to about 4 mL and diluted with H₂O (20 mL). The solution was cooled to 0° C. and acidified with concentrated HCl, the resulting solid was filtered, washed with H₂O, and dried to give the title compound (160 mg, 72%). HPLC $R_t$=3.87 min. m/z=404 (M+H⁺).

Example 223

2-(5-Acetyl-2-chloro-5,6-dihydrodibenz[b,f]azocin-8-yl)-N-methylbenzamide

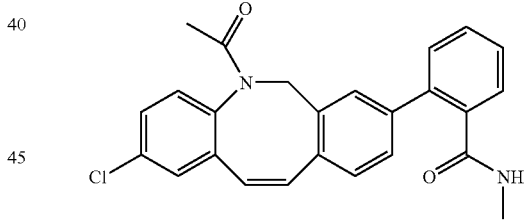

To a mixture Example 222 (10 mg, 0.025 mmol), BOP (16 mg, 0.0375 mmol), and HOBt (5 mg, 0.0375 mmol) in DMF (0.5 mL) was added DIEA (8 μl, 0.05 mmol) followed by methylamine (3.1 mg, 0.1 mmol). The reaction mixture was stirred overnight, concentrated and purified by preparative reversed-phase HPLC to give the title compound in (8.9 mg, 86%). HPLC $R_t$=3.58 min. m/z=417 (M+H⁺).

Examples 224 to 227

The following compounds in Table 18 have been synthesized utilizing the procedures described in Example 223, utilizing the appropriate starting materials.

TABLE 18

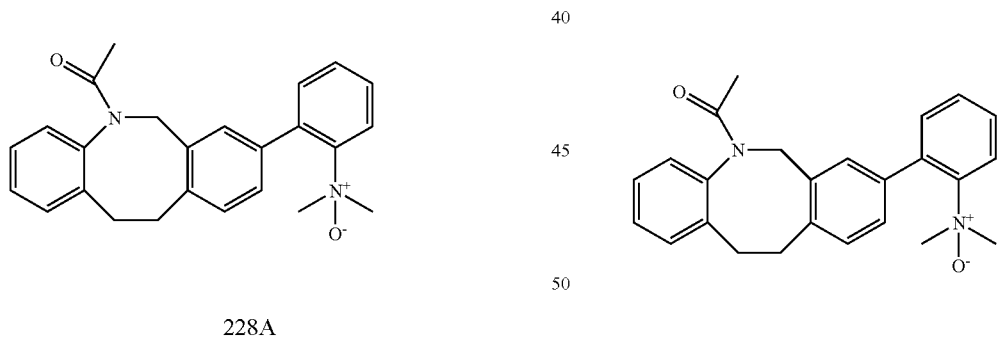

| Example No. | R | Compound name | [M + H] | HPLC Ret Time (min) |
|---|---|---|---|---|
| 224 | -NH-CH₂- (ethyl) | 2-(5-Acetyl-2-chloro-5,6-dihydrodibenz[b,f]azocin-8-yl)-N-ethylbenzamide | 431.30 | 3.623 |
| 225 | -NH-CH(CH₃)₂ | 2-(5-Acetyl-2-chloro-5,6-dihydrodibenz[b,f]azocin-8-yl)-N-(1-methylethyl)benzamide | 445.47 | 3.723 |
| 226 | pyrrolidinyl | 5-Acetyl-2-chloro-5,6-dihydro-8-[2-(1-pyrrolidinylcarbonyl)phenyl]dibenz[b,f]azocine | 457.28 | 3.800 |
| 227 | $NH_2$ | 2-(5-Acetyl-2-chloro-5,6-dihydrodibenz[b,f]azocin-8-yl)benzamide | 403.17 | 3.553 |

Example 228

5-Acetyl-8-[2-(dimethylamino)phenyl]-5,6,11,12-tetrahydrodibenz[b,f]azocine, N'-oxide

228A

Compound Example 228A was prepared by a route analogous to Example 22, starting from Example 15 and (2-Bromo-phenyl)-dimethyl-amine.

Example 228

To a solution of Example 228A (13 mg, 0.035 mmol) in $CH_2Cl_2$ (1 mL) was added a solution of mCPBA (13 mg, 0.05 mmol) in $CH_2Cl_2$ (0.5 mL). The mixture was stirred at room temperature overnight. The reaction mixture was concentrated and purified by radial chromatography (2 mm plate, 2% MeOH/$CH_2Cl_2$) to give the desired product. HPLC $R_t$=2.5 (b) min. m/z=387.4 (M+H⁺).

Example 229

5-Acetyl-8-[2-[(diethylamino)methyl]phenyl]-5,6,11,12-tetrahydrodibenz[b,f]azocine, N'-oxide

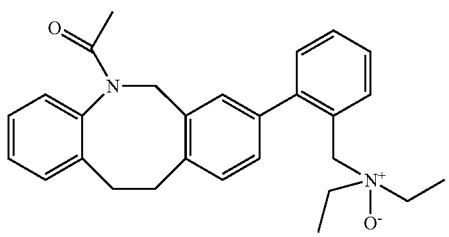

229A. Preparation of (2-Bromo-benzyl)-diethyl-amine

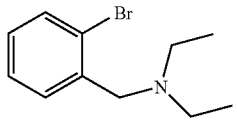

To 1-Bromo-2-bromomethyl-benzene (2.17 g, 0.008 mmol) in toluene (15 mL) was added diethylamine (3.05 mL) and the mixture was stirred at room temperature for 14 hours. The reaction mixture was filtered and concentrated to give Example 229A as an oil.

229B

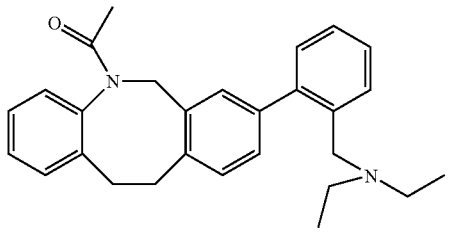

Example 229B was prepared in a manner analogous to Example 228A.

Example 229

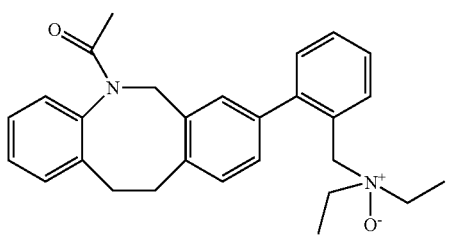

Example 229 (7 mg, 34%) was prepared from Example 29B (60 mg, 0.15 mmol) by a route analogous to that used for the preparation of Example 228. HPLC $R_f$=2.84 (b) min. m/z=429.24(M+H$^+$).

Example 230

5-Acetyl-2-chloro-5,6-dihydro-8-[2-(2-oxazolyl)phenyl]-dibenz[b,f]azocine

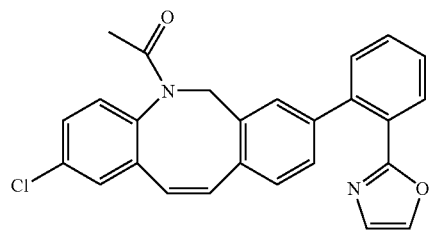

To a mixture of Example 222 (20 mg, 0.05 mmol) in CH$_2$Cl$_2$ (1 mL) was added one drop of DMF. The solution was cooled to 0° C., oxalyl chloride (3 μl, 0.055 mmol) was added and the reaction mixture was stirred for 30 minutes. The reaction mixture was concentrated to a yellow solid, taken up in sulfolane and treated with K$_2$CO$_3$ (14 mg, 0.1 mmol) and 1,2,3-triazine (3 μl, 0.05 mmol). The mixture was heated at 140° C. for 5 hours, then water was added. The resulting mixture was filtered, and the solid was purified by preparative reversed-phase HPLC to give the title compound (3.3 mg, 15%). HPLC $R_f$=2.36 (b) min. m/z=427 (M+H$^+$).

Example 231

5-Acetyl-2-chloro-5,6-dihydro-8-[2-(5-oxazolyl)phenyl]-dibenz[b,f]azocine

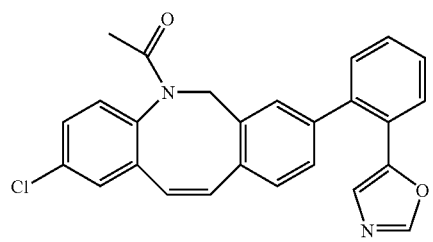

231A

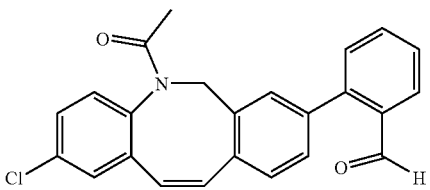

A solution of Example 1 (150 mg, 0.42 mmol) in toluene (2 mL) and EtOH (2 mL) was treated with Pd(PPh$_3$)$_4$ (116 mg, 0.04 mmol) under an argon atmosphere. A solution of 2-formyl phenylboronic acid (76 mg, 0.5 mmol) in EtOH (2 mL) was added followed by aqueous 2M Na$_2$CO$_3$ (0.62 mL, 2.07 mmol) The resulting solution was heated to reflux for three hours. After cooling to room temperature, the mixture was treated with saturated aqueous NaCl solution (10 mL) and the layers were separated. The aqueous layer was extracted with EtOAc (3×20 mL). The combined organic layers were dried (Na$_2$SO$_4$), filtered and concentrated. The product was purified by flash chromatography (SiO$_2$, 30% EtOAc/Hexanes) to afford Example 231A (145 mg, 89%).

Example 231

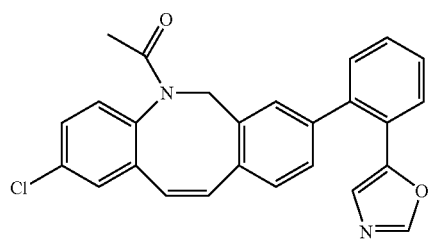

To a mixture of Example 231A (50 mg, 0.13 mmol) in MeOH (5 mL) was added tosylmethyl isocyanide (28 mg, 0.14 mmol) and K$_2$CO$_3$ (21 mg, 0.16 mmol). The reaction mixture was heated to reflux for 3 hours, then cooled to room temperature and concentrated. The residue was purified by preparative reversed-phase HPLC to give the title compound (35 mg, 64%) as white foam. HPLC R$_t$=2.433 (b) min. m/z=4 (M+H$^+$).

Example 232

5-Acetyl-2-chloro-5,6-dihydro-8-[2-(hydroxymethyl)phenyl]-dibenz[b,f]azocine

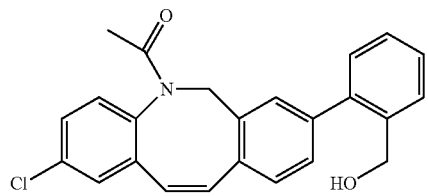

To a solution of Example 231A (30 mg, 0.078 mmol) in THF (1 mL) at 0° C. was added LiBH$_4$ (3 mg, 0.14 mmol). The reaction mixture was stirred for 1 hour, quenched with water and concentrated. The residue was purified by preparative reversed-phase HPLC to afford Example 231 (13 mg, 43%). HPLC R$_t$=2.33 (b) min. m/z=390.15 (M+H$^+$).

Example 233

5-Acetyl-2-chloro-5,6-dihydro-8-[2-(1-hydroxyethyl)phenyl]-dibenz[b,f]azocine

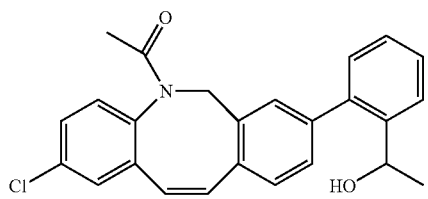

Compound Example 233 (13 mg, 48%) was prepared from Example 56 (30 mg, 0.07 mmol) by a route analogous to that used for the preparation of compound Example 232. HPLC R$_t$=4.0(b) min. m/z=386.20 (M-18).

Example 234

5-Acetyl-2-chloro-5,6-dihydro-8-[2-(methoxymethyl)phenyl]-dibenz[b,f]azocine

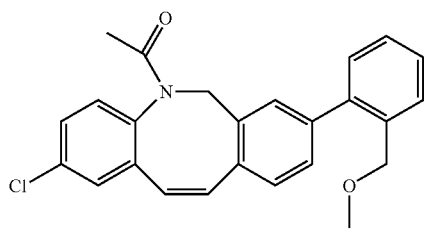

To a solution of Example 232 (14 mg, 0.036 mmol) in DMF (1 mL) at 0° C. was added 60% NaH (2 mg, 0.05 mmol) After 30 minutes, MeI (2.2 µl, 0.036 mmol) was added and the reaction was slowly warmed to room temperature. After stirring for 1 hour, the reaction was quenched with several drops of water and concentrated. The resulting waxy yellow solid was purified by preparative reversed-phase HPLC to give Example 234 (11 mg, 76%). HPLC R$_t$=2.487 (b) min. m/z=404.18 (M+H$^+$).

Example 235

5-Acetyl-2-chloro-5,6-dihydro-8-[2-[(methylamino)methyl]phenyl]-dibenz[b,f]azocine

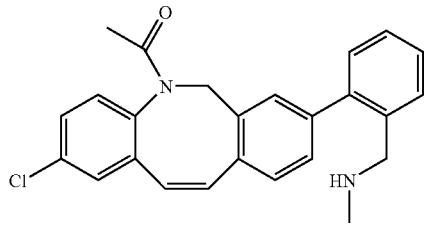

To a solution of Example 231A (20 mg, 0.05 mmol) in dichloroethane (1 mL) was added methylamine hydrochloride (3 mg, 0.07 mmol) followed by Na(OAc)$_3$BH (15 mg, 0.07 mmol). The reaction mixture was stirred at room temperature overnight. The resulting suspension was quenched with saturated aqueous NaHCO$_3$ (5 mL) and extracted with EtOAc (3×5 mL). The combined extracts were dried (Na$_2$SO$_4$), filtered and concentrated. The residue was purified by preparative reversed-phase HPLC to give Example 235 (7 mg, 27%). HPLC R$_t$=1.95 (b) min. m/z=403.23 (M+H$^+$).

Example 236

2-(5-Acetyl-2-chloro-5,6-dihydro-dibenzo[b,f]azocin-8-yl)-5-dimethylaminomethyl-benzoic acid methyl ester

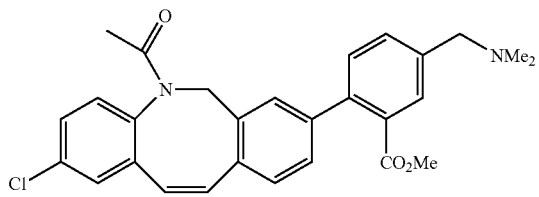

236A. Preparation of 5-Formyl-2-trifluoromethanesulfonyloxy-benzoic acid methyl ester

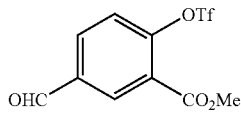

To a solution of 5-formyl-2-hydroxy-benzoic acid methyl ester (1.0 g, 5.6 mmol) in CH$_2$Cl$_2$ (10 mL) at −78° C. was added Et$_3$N (0.85 mL, 6.1 mmol) and DMAP (68 mg, 0.56 mmol) followed by dropwise addition of Tf$_2$O (1.03 mL, 6.1 mmol) over 20 min. The reaction mixture was then warmed to room temperature and poured into saturated aqueous NH$_4$Cl and extracted with CH$_2$Cl$_2$ (3×25 mL). The combined extracts were dried (Na$_2$SO$_4$), filtered and concentrated. The residue was purified by flash chromatography (SiO$_2$, 15% EtOAc/hexanes) to afford Example 236A (1.3 g, 76%) as a colorless oil.

236B. Preparation of 2-(5-Acetyl-2-chloro-5,6-dihydro-dibenzo[b,f]azocin-8-yl)-5-formyl-benzoic acid methyl ester

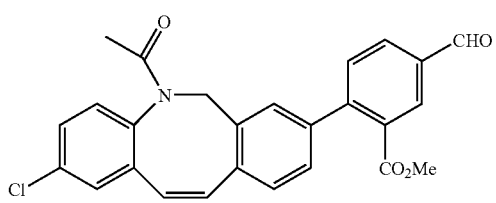

A 15 mL three necked oven dried round bottom flask was cooled under argon and charged with Example 21A (50 mg, 0.12 mmol), Example 236A (47 mg, 0.15 mmol) and toluene (2 mL)/EtOH (1 mL). The mixture was purged with argon for 30 minutes. Pd(PPh$_3$)$_4$ (14 mg, 0.012 mmol) and 2 M Na$_2$CO$_3$ (187 µl, 0.36 mmol) were added and the reaction was heated at 75° C. for 2 hours. The resulting mixture was poured into water (10 mL) and extracted with EtOAc (3×10 mL). The combined extracts were dried over Na$_2$SO$_4$, filtered and concentrated. The residue was purified by radial chromatography (2 mm plate, 30% to 50% EtOAc/Hexanes) to give the desired product Example 236B (29 mg, 55%).

Example 236

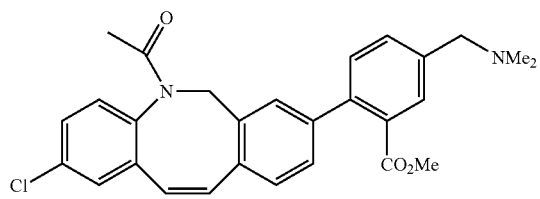

To a solution of Example 236B (20 mg, 0.045 mmol) in THF (2 mL) was added Me$_2$NH (54 µl, 0.108 mmol) followed by Na(OAc)$_3$BH (36 mg, 0.170 mmol). The reaction mixture was stirred overnight. The resulting suspension was quenched with saturated aqueous NaHCO$_3$ and extracted with EtOAc. The combined extracts were dried over Na$_2$SO$_4$, filtered and concentrated. The residue was purified by preparative reversed-phase HPLC to give Example 236 (18 mg, 84%). HPLC R$_t$=1.863 (b) min. m/z=475.34 (M+H$^+$).

Example 237

2-(5-Acetyl-2-chloro-9-methoxy-5,6-dihydro-dibenzo[b,f]azocin-8-yl)-N-methyl-benzamnide

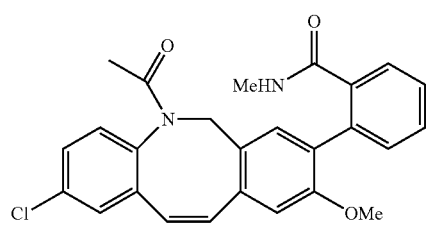

237A

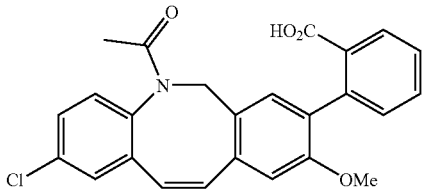

A mixture of Example 18 (40 mg, 0.10 mmol), 2-carboxyphenylboronic acid (25 mg, 0.15 mmol) in toluene (1 mL) and EtOH (1 mL) was purged with argon. Pd(PPh$_3$)$_4$ (30 mg, 0.026 mmol) and 2 M $Na_2CO_3$ (152 µl, 0.30 mmol) were added and the reaction was heated to 80° C. overnight. The mixture was then cooled to room temperature, concentrated and the residue was purified by preparative reversed-phase HPLC to give Example 237A (10 mg, 23%) as a yellow powder.

Example 237

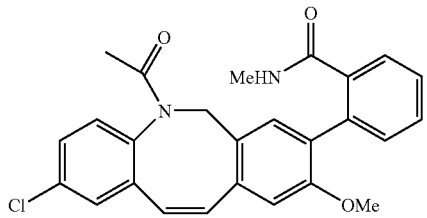

To a 10 mL round bottom flask was added Example 237A (10 mg, 0.02 mmol), $CH_2Cl_2$ (2 mL), BOP (18 mg, 0.035 mmol), DIEA (6 µl, 0.035 mmol) and $MeNH_2$ (23 µl, 2 M in THF, 0.046 mmol) sequentially. The reaction mixture was stirred at room temperature. After the starting material disappeared, the reaction was concentrated and the residue was purified by preparative reversed-phase HPLC to give Example 237 (4.7 mg, 46%). HPLC $R_t$=2.153 (b) min. m/z=447.13 (M+H$^+$).

Example 238

5-Acetyl-2-chloro-5,6-dihydro-8-phenyl-dibenz[b,f]azocin-9-ol

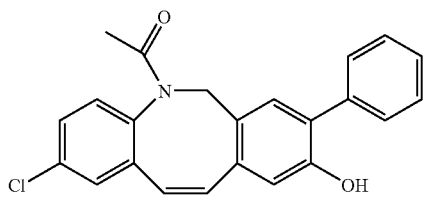

To a solution of Example 180 (22 mg, 0.057 mmol) in $CH_2Cl_2$ (2 mL) at 0° C. was added $BBr_3$ (21 µl, 0.23 mmol). The reaction mixture was stirred at 0° C. for 2 hours, quenched with MeOH and concentrated. The residue was purified by radial chromatography (2 mm plate, 0% to 1% MeOH/$CH_2Cl_2$) to afford Example 238 (17 mg, 80%). HPLC $R_t$=2.29 (b) min. m/z=376.17 (M+H$^+$).

Example 239

5-Acetyl-8-(2-acetylphenyl)-5,6-dihydro-2-methoxy-dibenz[b,f]azocine

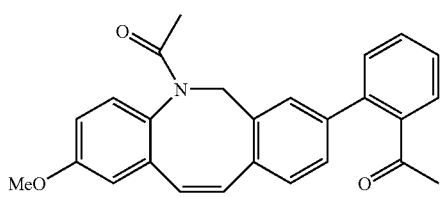

A solution of Example 12 (30 mg, 0.08 mmol) in toluene (0.8 mL) was treated with Pd(PPh$_3$)$_4$ (5 mg, 0.12 mmol) under an argon atmosphere. A solution of 2-Acetylphenylboronic acid (21 mg, 0.12 mmol) in EtOH (0.8 mL) was added followed by aqueous 2M $Na_2CO_3$ (63 µL, 0.12 mmol) The resulting solution was heated to reflux for three hours. After cooling to room temperature, the mixture was treated with saturated aqueous NaCl solution (1 mL) and the layers were separated. The aqueous layer was extracted with EtOAc (3×2 mL). The combined organic layers were dried (Na$_2$SO$_4$), filtered and concentrated. The product was purified by preparative HPLC to afford the title compound (23 mg, 25%). HPLC $R_t$=3.74 min. m/z=398 (M+H$^+$).

Example 240

5-Acetyl-8-(2-acetylphenyl)-5,6-dihydro-dibenz[b,f]azocin-2-ol

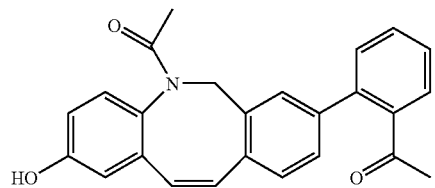

To a solution of compound Example 239 (23 mg, 0.05 mmol) in $CH_2Cl_2$ (2 mL) at 0° C. was added $BBr_3$ (11 µl, 0.10 mmol). The reaction mixture was stirred at 0° C. for 2 h, quenched with MeOH and poured into water. The aqueous layer was extracted with $CH_2Cl_2$ (3×2 mL). The combined organic layers were dried (Na$_2$SO$_4$), filtered and concentrated. The product was purified by preparative HPLC to afford the title compound (22 mg, 21%). HPLC $R_t$=3.37 min. m/z=384.2 (M+H$^+$).

Example 241

5-Acetyl-8-(2-acetylphenyl)-5,6-dihydro-2-[2-(1-pyrrolidinyl)ethoxy]-dibenz[b,f]azocine

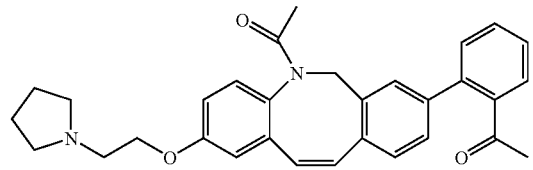

To a solution of compound Example 240 ( 20 mg, 0.05 mmol) in THF (4 mL) under argon was added 2-pyrrolidin-1-yl-ethanol (18 mg, 20.5 µl) and triphenylphosphine (34.2 mg, 0.13 mmol). To the mixture at 0° C. was added DEAD (22.7 mg, 0.13 mmol). The reaction mixture was stirred for 12 hours and then concentrated. The product was purified by preparative reversed-phase HPLC to afford the title compound (17 mg, 71%). HPLC $R_t$=2.67 min. m/z=481.3 (M+H$^+$).

Example 242

2-(5-Acetyl-5,6-dihydro-2-methoxydibenz[b,f]azocin-8-yl)-N-methyl-benzamide

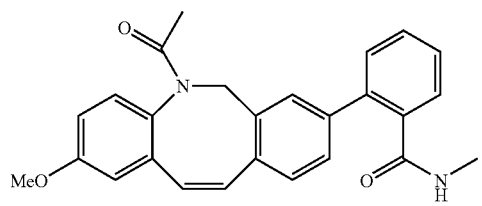

242A

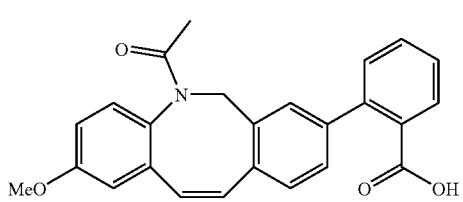

A solution of Example 12 (30 mg, 0.08 mmol) in toluene (0.8 mL) was treated with Pd(PPh$_3$)$_4$ (5 mg, 0.12 mmol) under an argon atmosphere. A solution of (2-carboxyphenyl)-boronic acid (21 mg, 0.12 mmol) in EtOH (0.8 mL) was added followed by aqueous 2M Na$_2$CO$_3$ (63 µL, 0.12 mmol) The resulting solution was heated to reflux for three hours. After cooling to room temperature, the mixture was treated with saturated aqueous NaCl solution (1 mL) and the layers were separated. The aqueous layer was extracted with EtOAc (3×2 mL). The combined organic layers were dried (Na$_2$SO$_4$), filtered and concentrated. The product was purified by preparative HPLC to afford the title compound (13 mg, 41%).

Example 242

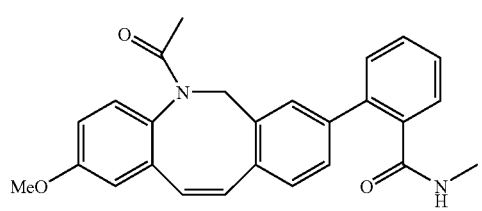

To Example 242A (13 mg, 0.032 mmol) in DMF (5 mL) was added BOP (20 mg, 0.039 mmol), Et$_3$NA (10 µl, 0.064 mmol) and MeNH$_2$ hydrochloride(5 mg, 0.064 mmol) sequentially. The reaction mixture was stirred at room temperature. After the starting material disappeared, the solution was poured into water and extracted with EtOAc. The organic layers were dried (Na$_2$SO$_4$), filtered and concentrated. The product was purified by radial chromatography (1 mm plate, 100% EtOAc) to give Example 242 (12 mg, 90%). HPLC R$_f$=3.27 min. m/z=413.2 (M+H$^+$).

Example 243

2-(5-Acetyl-5,6-dihydro-2-hydroxydibenz[b,f]azocin-8-yl)-N-methyl-benzamide

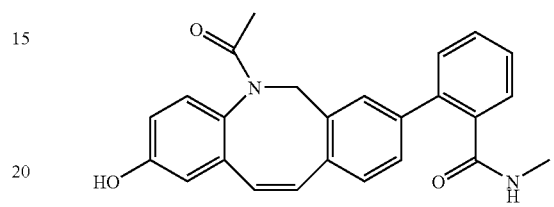

Example 243 (28 mg, 32%) was prepared from Example 242 (90 mg, 0.22 mmol) by a route analogous to that used for the preparation of Example 240. HPLC R$_f$=2.87 min. m/z=399.20

Example 244

2-[5-Acetyl-5,6-dihydro-2-[2-(1-pyrrolidinyl)ethoxy]dibenz[b,f]azocin-8-yl]-N-methyl-benzamide

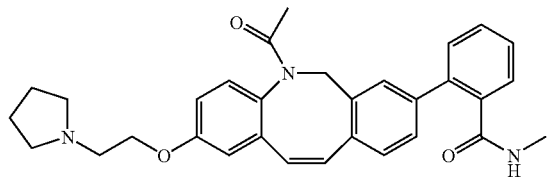

Example 244 (28 mg, 32%) was prepared from Example 243 (5 mg, 0.01 mmol) by a route analogous to that used for the preparation of Example 241. HPLC R$_f$=2.25 min. m/z=496.3.

Example 245

5-Acetyl-5,6-dihydro-8-[2-[(methylamino)carbonyl]phenyl]-dibenz[b,f]azocine-2-carboxylic acid methyl ester

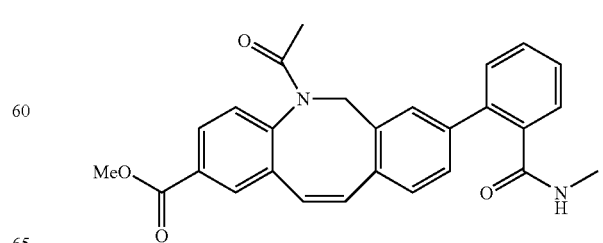

245A

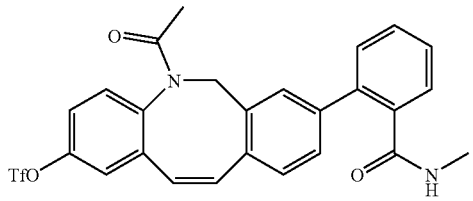

To a solution of Example 243 (28 mg, 0.07 mmol) in CH$_2$Cl$_2$ (1 mL) was added DMAP (0.8 mg) and TEA (10.5 µl). The solution was cooled to −78° C. and triflic anhydride (21.8 mg, 0.77 mmol) was added. The reaction mixture was stirred at −78° C. for 4 hours, then quenched with water (2 mL). The layers were separated and the organic layer was dried (Na$_2$SO$_4$), filtered and concentrated to provide Example 245A.

Example 245

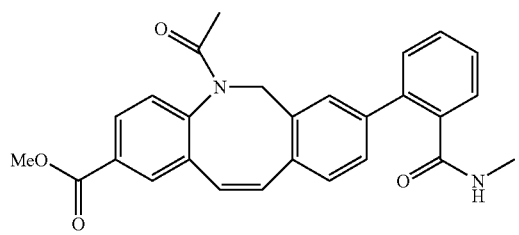

To a solution of Example 245A (20 mg, 0.037 mmol) in DMF (0.6 mL) under argon was added palladium acetate (0.4 mg, 0.002 mmol), Dppf (2 mg), MeOH (0.3 mL), and TEA (10.5 µl, 0.07 mmol). The reaction was purged with CO(g) for 5 minutes the stirred at 60° C. for 8 hours under a CO atmosphere. The reaction mixture was filtered and concentrated. The residue was purified by preparative reversed-phase HPLC to give the title compound. HPLC R$_t$=3.28 min. m/z=441 (M+H$^+$).

Example 246

5-Acetyl-3-chloro-9-fluoro-5,6-dihydro-8-[2-(1,3,4-oxadiazol-2-yl)phenyl]-dibenz[b,f]azocine

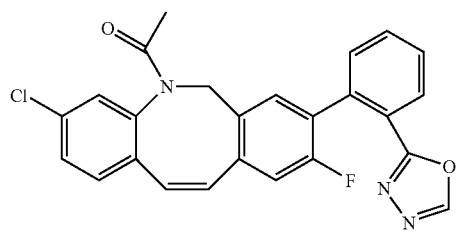

246A

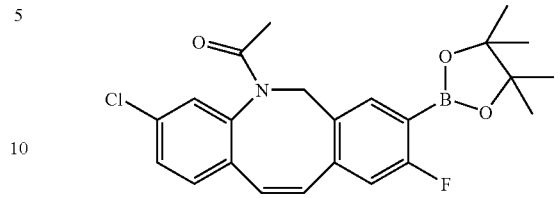

To a 10 mL round bottom flask was added Example 11 (250 mg, 0.66 mmole) in dioxane (5 mL) under an argon atmosphere. To this solution was added (diphenylphosphino)ferrocine (37 mg, 0.066 mmole), bis(pinacolato)diboron (332 mg, 1.31 mmole), potassium acetate (194 mg, 1.98 mmole) and palladium dichloride(diphenylphosphino)ferrocine (48 mg, 0.066 mmole). The reaction mixture was heated to 90° C. for 6 hours. The reaction was concentrated, dissolved in 1:1 ethyl acetate/hexanes and passed through a pad of silica to give Example 246A.

246B. Preparation of 2-Bromo-benzoic acid hydrazide

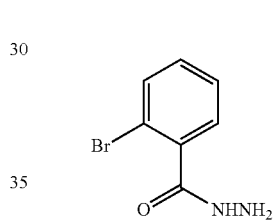

A solution of methyl 2-bromobenzoate (1.0 g, 4.7 mmol) in EtOH (15 mL) was treated with hydrazine (0.18 mL, 5.6 mmol) and heated to reflux for 15 hours. The resulting solution was concentrated to a white powder (998 mg).

246C. Preparation of 2-(2-Bromo-phenyl)-[1,3,4]oxadiazole

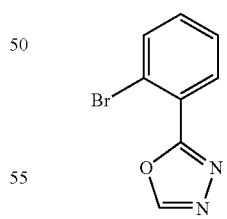

A solution of Example 246B (200 mg, 0.93 mmol), toluene (5 mL), ethyl orthoformate (1 mL) and pTsOH (20 mg) was heated to reflux for two hours. The resulting solution was cooled to room temperature and concentrated. The residue was dissolved in Et$_2$O and washed with H$_2$O (20 mL), 0.1 M HCl (20 mL) and brine (20 mL), dried (Na$_2$SO$_4$), filtered and concentrated. The crude product was purified by radial chromatography (2 mm plate, 20% EtOAc/hexanes) to afford Example 246C (140 mg, 67%).

Example 246

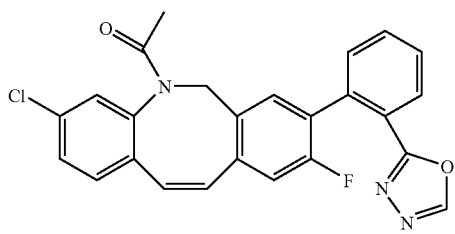

To a solution of Example 246A (48 mg, 0.11 mmol) and Example 246B (25 mg, 0.11 mmol) in EtOH (1 mL) and toluene (1 mL) under an argon atmosphere were added 2M $Na_2CO_3$ (0.165 mL, 0.33 mmol) followed by $Pd(PPh_3)_4$ (13 mg, 0.011 mmol)). The resulting suspension was stirred under argon at 85° C. for 2 hours. The reaction was cooled to ambient temperature, concentrated and purified by preparative HPLC to give the title compound (8.8 mg). HPLC $R_t$=2.203 min. m/z=446.08.

Example 247

5-Acetyl-3-chloro-9-fluoro-5,6-dihydro-8-[2-(5-methyl-1,3,4-oxadiazol-2-yl)phenyl]-dibenz[b,f]azocine

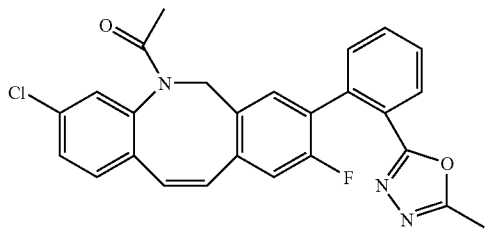

To a solution of Example 246A (143 mg, 0.34 mmol) and 2-(2-Bromo-phenyl)-5-methyl-[1,3,4]oxadiazole (prepared in a manner similar to Example 246C) (40 mg, 0.17 mmol) in EtOH (2 mL) and toluene (2 mL) under an argon atmosphere were added 2M $Na_2CO_3$ (0.255 mL, 0.51 mmol) followed by $Pd(PPh_3)_4$ (20 mg). The resulting suspension was stirred under argon at 85° C. for 2 hours. The reaction was cooled to ambient temperature, concentrated and purified by preparative HPLC to give the title compound (24.3 mg). HPLC $R_t$=2.23 min. m/z=460.15.

Examples 248 and 249

2-(5-Acetyl-2-chloro-5,6-dihydrodibenz[b,f]azocin-8-yl)-(1S,2S-rel)-cyclopropanecarboxylic acid ethyl ester and 2-(5-Acetyl-2-chloro-5,6-dihydrodibenz[b,f]azocin-8-yl)-(1S,2R-rel)-cyclopropanecarboxylic acid ethyl ester

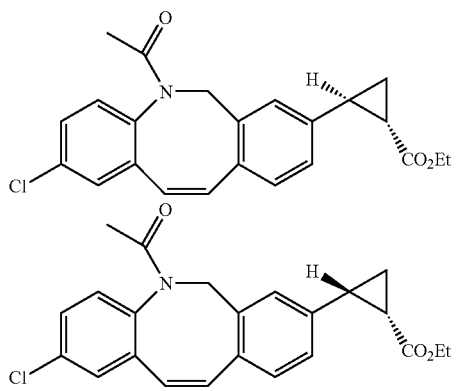

248A

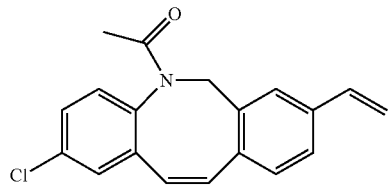

A solution of Example 1 (200 mg, 0.55 mmol) in dioxane (8 mL) was purged with argon for 30 minutes. Vinyl tri-N-butyltin (194 µl, 0.66 mmol) and $PdCl_2(PPh_3)_2$ (78 mg, 0.11 mmol) were added. The reaction mixture was heated at reflux for 1 h, then cooled to room temperature and concentrated. The residue was purified by flash chromatography ($SiO_2$, (20% EtOAc—hexanes) followed by radial chromatography (2 mm plate, 20% to 40% EtOAc/hexanes) to afford Example 248A (120 mg, 71%) as a light yellow powder.

Examples 248 and 249

Preparation of cis- and trans-2-(5-Acetyl-2-chloro-5,6-dihydro-dibenzo[b,f]azocin-8-yl)-cyclopropanecarboxylic acid ethyl ester

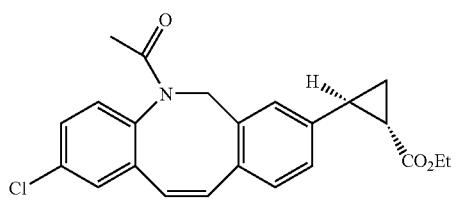

-continued

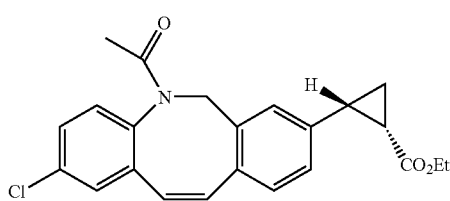

To a solution of Example 248A (100 mg, 0.32 mmol) in THF (2 mL) was added Pd(OAc)$_2$ (7.2 mg, 0.032 mmol). Then a solution of EtO$_2$CCHN$_2$ (92 mg, 0.81 mmol) in Et$_2$O (0.5 mL) was added dropwise. After half of the addition, additional Pd(OAc)$_2$ (3.5 mg, 0.016 mmol) was added. After the addition was complete, the reaction was stirred until the starting material was consumed. The mixture was concentrated and the residue was purified by radial chromatography (2 mm plate, 30% EtOAc/hexanes) to afford the desired product as Example 248 (trans) (66 mg, 52%) HPLC R$_t$=4.1 min. m/z=396 (M+H$^+$) and Example 249 (cis) product (35 mg, 28%). HPLC R$_t$=3.87 min. m/z=396 (M+H$^+$)

Example 250 trans-2-(5-Acetyl-2-chloro-5,6-dihydro-dibenzo[b,f]azocin-8-yl)-cyclopropanecarboxylic acid methylamide

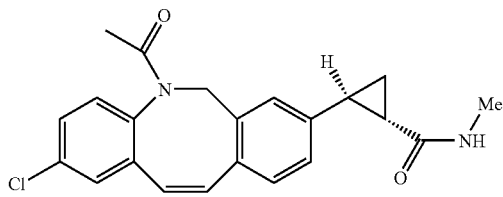

250A

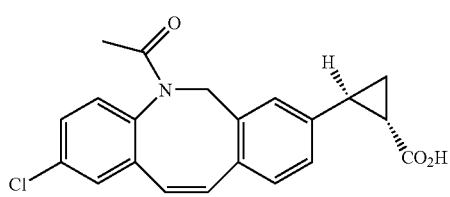

To a solution of Example 248 (10 mg, 0.025 mmol) in MeOH (0.5 mL) was added 1N NaOH (38 µl, 0.038 mmol). The mixture was stirred at 40° C. for 4 hours, additional 1N NaOH (50 µl, 0.050 mmol) was added, and the reaction mixture was stirred at 110° C. overnight. The resulting solution was concentrated to about 100 µl, diluted with water (1 mL), treated with 1N HCl and extracted with EtOAc (3×1 mL). The combined extracts were dried over Na$_2$SO$_4$, filtered and concentrated to give Example 250A (9 mg, 97%).

Example 250

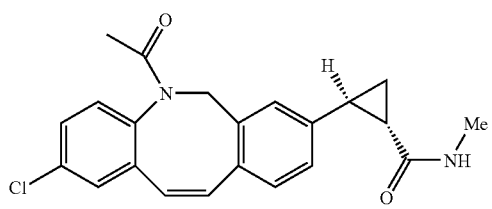

Example 250 was prepared from Example 250A by a route analogous to that used for the preparation of Example 237B. HPLC R$_t$=2.08(b) min. m/z=381 (M+H$^+$).

Example 251 cis-2-(5-Acetyl-2-chloro-5,6-dihydro-dibenzo[b,f]azocin-8-yl)-cyclopropanecarboxylic acid methylamide

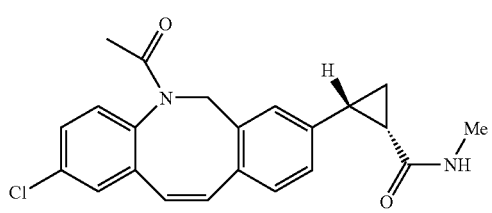

251A. Preparation of cis-2-(5-Acetyl-2-chloro-5,6-dihydrodibenzo[b,f]azocin-8-yl)-cyclopropanecarboxylic acid

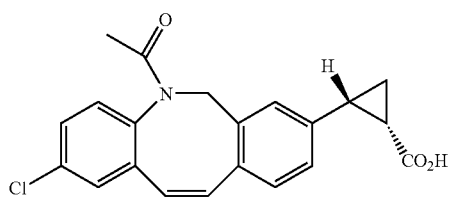

Example 251A (9 mg, 97%) was prepared from Example 249 (10 mg, 0.025 mmol) by a route analogous to that used for the preparation of Example 250A. The only difference was the reaction was carried out at 50° C.

Example 251

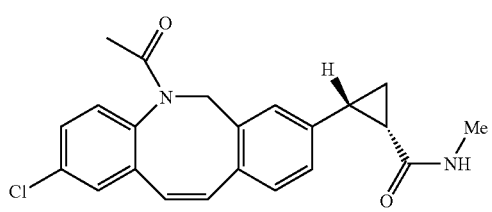

Example 251 (6 mg, 80%) was prepared from Example 251A (9 mg, 0.02 mmol) by a route analogous to that used for the preparation of Example 250B. HPLC $R_t$=2.17 min. m/z=381 (M+H$^+$).

Example 252

5-Acetyl-2-chloro-5,6-dihydro-8-[(1S,2R-rel)-2-(methoxymethyl)cyclopropyl]-dibenz[b,f]azocine

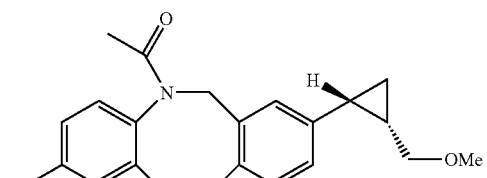

252A

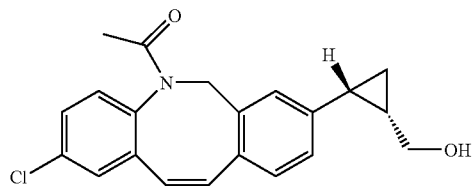

To a solution of Example 249 (25 mg, 0.063 mmol) in THF (1 mL) at 0° C. was added LiBH$_4$. The reaction mixture was stirred at room temperature overnight. The resulting mixture was quenched with water and extracted with EtOAc. The organic layer was dried over Na$_2$SO$_4$, filtered and concentrated. The residue was purified by radial chromatography (1 mm plate, 0% to 5% MeOH/CH$_2$Cl$_2$) to give Example 252A (7.6 mg, 34%).

Example 252

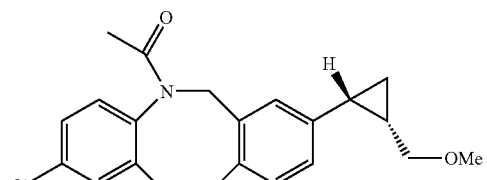

Example 252 (4.3 mg, 69%) was prepared from Example 252A (6.0 mg, 0.017 mmol) by a route analogous to that used for the preparation of Example 232. HPLC $R_t$=2.35(b) min. m/z=368 (M+H$^+$).

Example 253

5-Acetyl-2-chloro-5,6-dihydro-8-[(1R,2R-rel)-2-(methoxymethyl)cyclopropyl]-dibenz[b,f]azocine

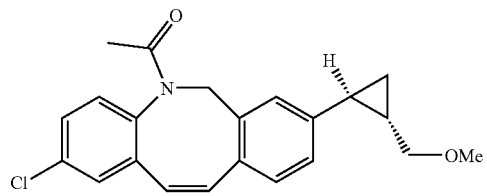

253A

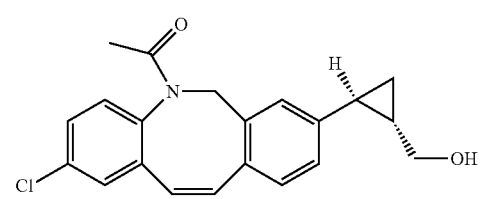

Example 253A was prepared from trans-ester from Example 248 by a route analogous to that used for the preparation of Example 252A.

Example 253

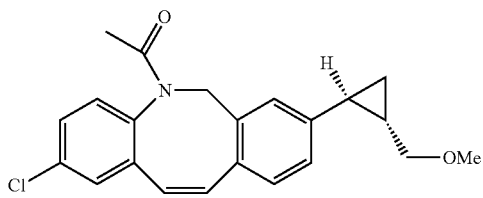

Example 253 was prepared from Example 253A (6.0 mg, 0.017 mmol) by a route analogous to that used for the preparation of Example 252. HPLC $R_t$=2.36(b)min. m/z=398 (M+H$^+$).

Example 254

5-Acetyl-2-chloro-5,6-dihydro-8-(2-oxazolyl)-dibenz[b,f]azocine

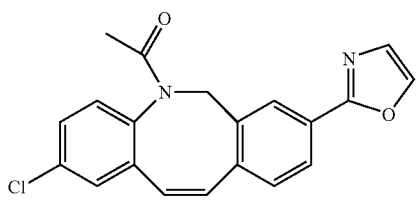

254A

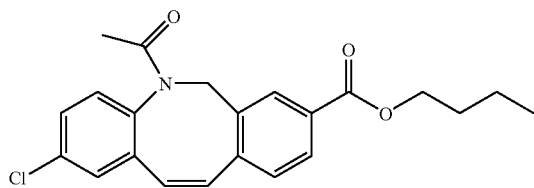

A solution of Example 1 (500 mg, 1.4 mmol), n-BuOH (20 mL) and Et$_3$N (15 mL) was purged with CO(g) for 30 minutes. PdCl$_2$(PPh$_3$)$_2$ (97 mg, 0.138 mmol) was added and the mixture was heated to 100° C under a constant stream of CO(g). After 2 hours, the reaction mixture was concentrated to about 10 mL, taken up in EtOAc (100 mL), washed with 0.1 N HCl (2×100 mL), NaHCO$_3$ (2×100 mL), brine (1×100 mL), dried over Na$_2$SO$_4$, filtered and concentrated. The residue was purified by flash chromatography (SiO$_2$, 30% EtOAc/hexanes) to give Example 254A (349 mg, 66%) as an off-white solid.

254B. Preparation of 5-Acetyl-2-chloro-5,6-dihydro-dibenzo[b,f]azocine-8-carboxylic acid

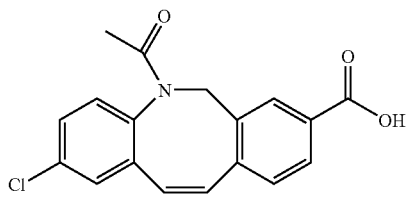

To a solution of Example 254A (150 mg, 0.39 mmol) in THF (5 mL) and MeOH (2.5 mL) at 0° C. was added a solution of LiOH.H$_2$O (25 mg, 0.60 mmol) in H$_2$O (2 mL). The mixture was stirred at 45° C. overnight. The solution was cooled to 0° C., treated with 0.1N HCl, and the resulting white solid was filtered and dried in vacuo to give Example 254B (118 mg, 93%).

Example 254

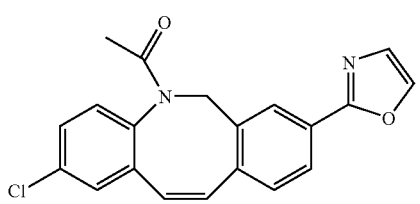

Example 254 (5 mg, 24%) was prepared from Example 254B (20 mg, 0.06 mmol) by a route analogous to that used for the preparation of Example 230. HPLC R$_t$=2.36(b)min. m/z=368(M+H$^+$).

Example 255

5-Acetyl-2-chloro-5,6-dihydro-dibenzo[b,f]azocine-8-carboxylic acid oxazol-2-ylamide

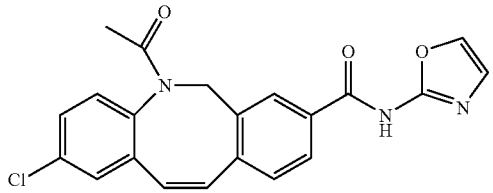

To an oven dried 10 mL round bottom flask was added Example 254B (20 mg, 0.06 mmol), DMF (1 mL), DMAP (11 mg, 0.09 mmol) and oxazol-2-ylamine (13 mg, 0.15 mmol), followed by DCC (20 mg, 0.09 mmol). The mixture was stirred at room temperature for 7 hours then concentrated. The residue was purified by preparative reversed-phase HPLC to give Example 255 (3 mg, 13 %). HPLC R$_t$=2.03(b) min. m/z=394 (M+H$^+$).

Examples 256 to 257

The following compounds in Table 19 have been synthesized utilizing the procedures described in Example 255, utilizing the appropriate starting materials.

TABLE 19

| Example No. | R$_{10}$ | Compound name | [M + H] | HPLC Ret Time (min) |
|---|---|---|---|---|
| 256 | ⸺C(O)NHMe | 5-Acetyl-2-chloro-5,6-dihydro-N-methyldibenz[b,f]azocine-8-carboxamide | 341 | 3.17 |

TABLE 19-continued

| Example No. | $R_{10}$ | Compound name | [M + H] | HPLC Ret Time (min) |
|---|---|---|---|---|
| 257 | 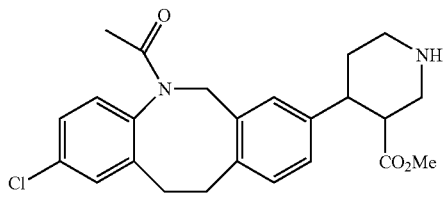 | 5-Acetyl-2-chloro-5,6-dihydro-N-methyl-N-2-oxazolyldibenz[b,f]azocine-8-carboxamide | 408 | 2.09(b) |

Example 258

4-(5-Acetyl-2-chloro-5,6,11,12-tetrahydrodibenz[b,f]azocin-8-yl)-3-piperidinecarboxylic acid methyl ester

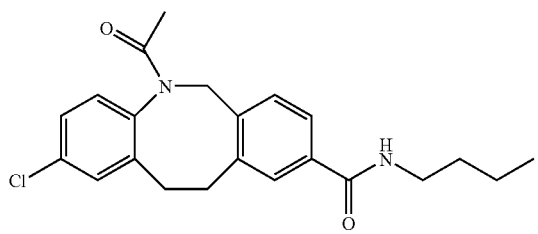

To a solution of Example 39 (25 mg, 0.06 mmol) in AcOH (2 mL) was added TFA (5 μl, 0.06 mmol), followed by $Pt_2O$ (2 mg, 0.012 mmol). The reaction mixture was stirred under a $H_2$ atmosphere for 72 hours. The reaction mixture was concentrated and the residue was purified by preparative reversed-phase HPLC to afford the TFA salt as a white foam. The salt was converted to the free base (15 mg, 59%) by treated with saturated aqueous $NaHCO_3$. HPLC $R_t$=1.78(b) min. m/z=427 (M+H$^+$).

Example 259

5-Acetyl-N-butyl-2-chloro-5,6,11,12-tetrahydro-dibenz[b,f]azocine-9-carboxamide

259A

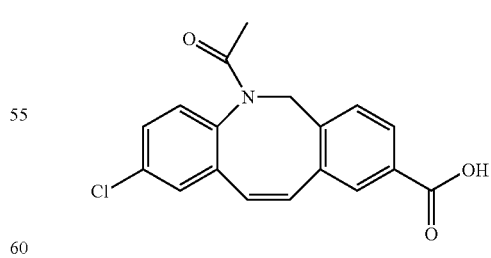

A solution of Example 3 (1.08 g, 3 mmol) in nBuOH (27 mL) and $Et_3N$ (17 mL) was saturated with a stream of CO (g). $PdCl_2(PPh_3)_2$ (120 mg) was added and CO(g) was bubbled through the mixture for 1 hour. The resulting suspension was stirred at 110° C. for 1 hour then concentrated. The residue was partitioned between EtOAc (50 mL) and saturated aqueous $NaHCO_3$ (30 mL) and the aqueous layer was extracted with EtOAc (30 mL). The combined organic layers were dried ($Na_2SO_4$), filtered and concentrated. Flash chromatography ($SiO_2$, 30% to 50% EtOAc./Hexanes) afforded Example 259A as a viscous yellow oil (815 mg, 71%).

259B

A clear solution of Example 259A (814 mg, 2.12 mmol) in EtOH (35 mL) and $H_2O$ (5 mL) was treated with KOH (1.2 g) and stirred at room temperature for 2.5 hours. The resulting reaction mixture was concentrated to remove the EtOH and the residue was dissolved in $H_2O$ and extracted with $Et_2O$. The aqueous layer was acidified with saturated $KHSO_4$, extracted with EtOAc and the organic layers were dried (Na$_2$SO$_4$), filtered and concentrated to afford Example 259B (578 mg, 83%).

259C. 5-Acetyl-N-butyl-2-chloro-5,6-dihydro-dibenz[b,f]azocine-9-carboxamide

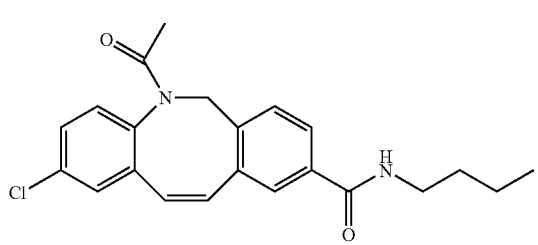

To a stirred solution of Example 259B (40 mg, 0.12 mmol), HOBt (28 mg, 0.18 mmol) and nButylamine (26 mg, 0.36 mmol) in DMF (2 mL) was added EDAC (34 mg, 0.18 mmol). After two hours at room temperature the reaction was warmed to 55° C. for one hour. Additional n-butylamine (26 mg) and EDAC (34 mg) were added and heating was continued for one hour. The resulting mixture was partitioned between EtOAc (20 mL) and 1 M HCl (20 mL). The organic layer was separated and washed with 1M HCl (20 mL), 0.2 M NaOH (2×20 mL), dried (Na$_2$SO$_4$), filtered and concentrated. The residue was purified by flash chromatography (SiO$_2$, 3:1 EtOAc/Heptane) to afford Example 259C (35 mg, 76%). HPLC R$_f$=1.72(d) min. m/z=383 (M+H$^+$).

Example 259

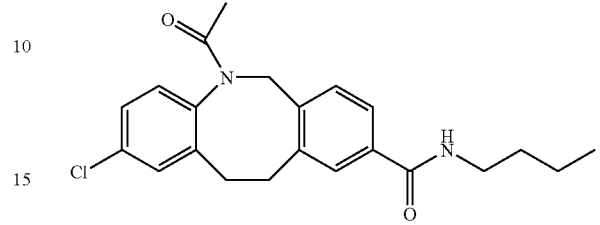

A suspension of Example 259C (23 mg, 0.06 mmol) and 5% Rh/C (3.9 mg) in MeOH (2 mL) was stirred under a H$_2$ atmosphere for eight hours. The reaction mixture was filtered to remove catalyst and concentrated to afford Example 259 as a white solid (23 mg, 100%). HPLC R$_f$=1.68(d) min. m/z=385 (M+H$^+$).

Examples 260 to 269

The compounds found in Table 20 and Table 21 were prepared as described for Example 259.

TABLE 20

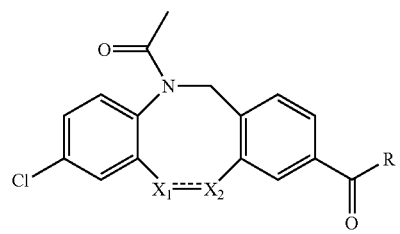

| Example No. | X$_1$═══X$_2$ | R | Compound name | [M + H] | HPLC Ret Time (min) |
|---|---|---|---|---|---|
| 260 | (cis double bond) | HN-CH$_2$CH$_2$-OH | 5-Acetyl-2-chloro-5,6-dihydro-N-(2-hydroxyethyl)-dibenz[b,f]azocine-9-carboxamide | 371 | 1.43(d) |
| 261 | (single bond) | HN-CH$_2$CH$_2$-OH | 5-Acetyl-2-chloro-5,6,11,12-tetrahydro-N-(2-hydroxyethyl)-dibenz[b,f]azocine-9-carboxamide | 373 | 1.36(d) |
| 262 | (cis double bond) | HN-CH$_2$CH$_2$-O-CH$_3$ | 5-Acetyl-2-chloro-5,6-dihydro-N-(2-methoxyethyl)-dibenz[b,f]azocine-9-carboxamide | 385 | 1.53(d) |
| 263 | (single bond) | HN-CH$_2$CH$_2$-O-CH$_3$ | 5-Acetyl-2-chloro-5,6,11,12-tetrahydro-N-(2-methoxyethyl)-dibenz[b,f]azocine-9-carboxamide | 387 | 1.48(d) |

TABLE 20-continued

[Structure: 5-acetyl-2-chloro-5,6-dihydro-dibenz[b,f]azocine-9-carbonyl-R core, with X₁=X₂ variable]

| Example No. | X₁═══X₂ | R | Compound name | [M + H] | HPLC Ret Time (min) |
|---|---|---|---|---|---|
| 264 | (cis-alkene) | ~NH-CH₂CH₃ (diethylamino) | 5-Acetyl-2-chloro-N,N-diethyl-5,6-dihydro-dibenz[b,f]azocine-9-carboxamide | 415 (M + Na⁺) | 1.66(d) |
| 265 | (saturated) | ~NH-CH₂CH₃ (diethylamino) | 5-Acetyl-2-chloro-N,N-diethyl-5,6,11,12-tetrahydro-dibenz[b,f]azocine-9-carboxamide | 385 | 1.61(d) |

TABLE 21

[Structure: 5-acetyl-5,6-dihydro-dibenz[b,f]azocine-9-carbonyl-R core, with X₁=X₂ variable]

| Example No. | X₁═══X₂ | R | Compound name | [M + H] | HPLC Ret Time (min) |
|---|---|---|---|---|---|
| 266 | (cis-alkene) | O-butyl | 5-Acetyl-5,6-dihydro-dibenz[b,f]azocine-9-carboxylic acid butyl ester | 350 | 4.36 |
| 267 | (cis-alkene) | OH | 5-Acetyl-5,6-dihydro-dibenz[b,f]azocine-9-carboxylic acid | 294 | 3.38 |
| 268 | (cis-alkene) | HN-CH₂CH₂-OCH₃ | 5-Acetyl-5,6-dihydro-N-(2-methoxyethyl)-dibenz[b,f]azocine-9-carboxamide | 351 | 1.39(d) |
| 269 | (saturated) | HN-CH₂CH₂-OCH₃ | 5-Acetyl-5,6,11,12-tetrahydro-N-(2-methoxyethyl)-dibenz[b,f]azocine-9-carboxamide | 353 | 1.34(d) |

Example 270

5-Acetyl-5,6,11,12-tetrahydro-dibenz[b,f]azocine-9-carboxylic acid butyl ester

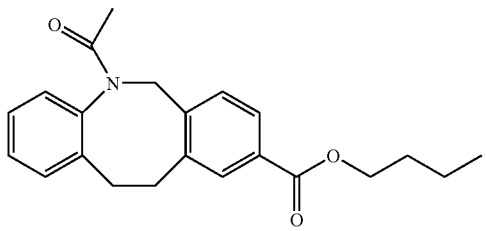

270A. 5-Acetyl-5,6,11,12-tetrahydro-dibenz[b,f]azocine-9-carboxylic acid

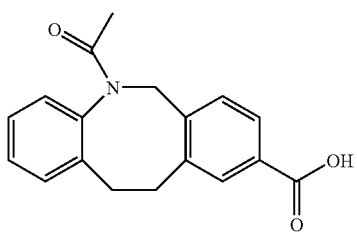

A mixture of Example 267 (335 mg, 1.14 mmol) in MeOH (20 mL) and THF (8 mL) was treated with 20% Pd(OH)$_2$/C (55 mg). The suspension was stirred at room temperature under a H$_2$ atmosphere for 2.5 hours. The catalyst was removed by filtration and the filtrate was concentrated to afford Example 270B as a yellow solid (329 mg, 97%). HPLC R$_t$=3.26 min. m/z=296.

Example 270

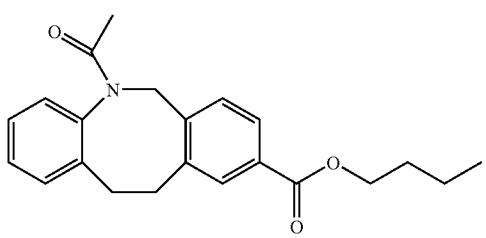

A solution of Example 270B (10 mg, 0.034 mmol) in DMF (0.5 mL) was treated with carbonyldiimidazole (7 mg, 0.043 mmol) and heated at 40° C. for 1 hour. To this mixture was added nBuOH (0.02 mL, 0.22 mmol) and DBU (0.01 mL, 0.067 mmol) and heating at 40° C. was continued overnight. The reaction mixture was cooled and partitioned between EtOAc and H$_2$O. The aqueous layer was extracted with EtOAc, the combined organic layers were dried (Na$_2$SO$_4$), and filtered through a pad of silica to afford Example 270 (10 mg, 82%). HPLC R$_t$=4.27 min. m/z=352.

Examples 271 to 272

The compounds found in Table 22 were prepared in a manner similar to Example 270.

TABLE 22

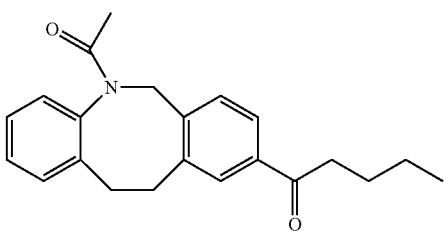

| Example No. | R | Compound name | [M + H] | HPLC Ret Time (min) |
|---|---|---|---|---|
| 271 | Me | 5-Acetyl-5,6,11,12-tetrahydro-dibenz[b,f]azocine-9-carboxylic acid methyl ester | 310 | 3.61 |
| 272 | iPr | 5-Acetyl-5,6,11,12-tetrahydro-dibenz[b,f]azocine-9-carboxylic acid isopropyl ester | 338 | 3.99 |

Example 273

5-Acetyl-5,6,11,12-tetrahydro-9-(1-oxopentyl)-dibenz[b,f]azocine

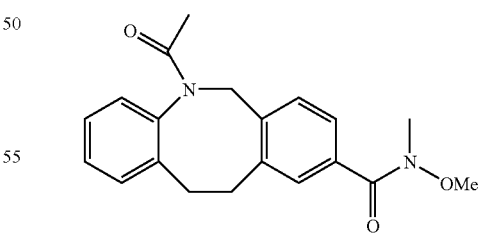

273A. 5-Acetyl-5,6,11,12-tetrahydro-N-methoxy-N-methyl-dibenz[b,f]azocine-9-carboxamide A solution of Example 270A (73 mg, 0.25 mmol), N,O-dimethylhydroxylamine hydrochloride (49 mg, 0.5 mmol), DMAP (16 mg, 0.13 mmol) and Et$_3$N (0.28 mL, 2 mmol) in CH$_2$Cl$_2$ (10 mL) was treated with EDAC hydrochloride at room temperature and stirred over night. The resulting solution was filtered through a pad of silica eluting with EtOAc to afford the Example 273A (47 mg, 56%). HPLC R$_t$=3.21 min. m/z=338.

Example 273

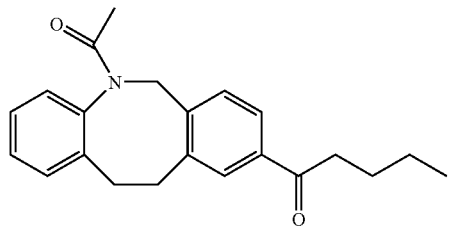

To a clear solution of Example 273A (18 mg, 0.053 mmol) in THF (4 mL) at −78° C. was added a 2.5 M solution of nBuLi (0.2 mL, 0.5 mmol) in THF dropwise. The reaction mixture was stirred at −78° C. for 25 minutes then slowly warmed to 0° C. over 10 minutes. The reaction was quenched with addition of NH$_4$Cl (0.2 mL), concentrated and purified by reversed-phase HPLC to afford the desired Example 273 (13 mg, 73%). HPLC R$_t$=4.10 min. m/z=336 (M+H$^+$).

Examples 274 to 276

The compounds found in Table 23 were prepared according to the procedures described in Example 273.

Example 277

5-Acetyl-5,6-dihydro-9-(phenylmethoxy)-dibenz[b,f]azocine

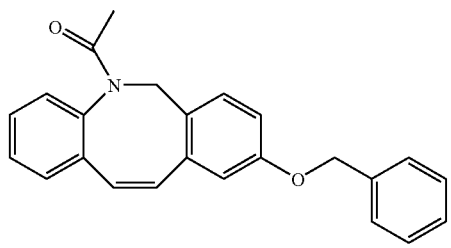

277A. 5-Acetyl-5,6-dihydro-dibenz[b,f]azocin-9-ol

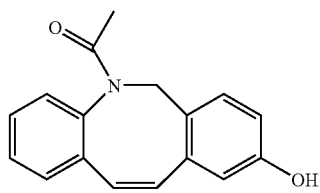

TABLE 23

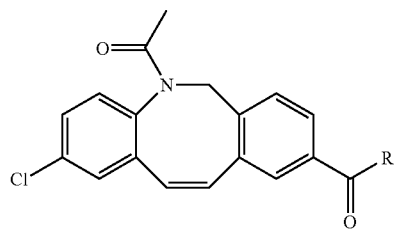

| Example No. | R | Compound name | [M + H] | HPLC Ret Time (min) |
|---|---|---|---|---|
| 274 | Me | 5,9-Diacetyl-2-chloro-5,6-dihydro-dibenz[b,f]azocine | 326 | 3.78 |
| 275 | 2-furanyl | 5-Acetyl-2-chloro-9-(2-furanylcarbonyl)-5,6-dihydro-dibenz[b,f]azocine | 378 | 3.91 |
| 276 | cyclopropyl | 5-Acetyl-2-chloro-9-(cyclopropylcarbonyl)-5,6-dihydro-dibenz[b,f]azocine | 352 | 4.03 |

To a clear solution of Example 16 (61 mg, 0.22 mmol) in CH$_2$Cl$_2$ (2 mL) at 0° C. was added 1M BBr$_3$ (0.44 mL, 0.44 mmol) in CH$_2$Cl$_2$ dropwise under argon. The mixture was stirred for 2.5 hours at 0° C. and then quenched with saturated aqueous NaHCO$_3$ (5 mL). The mixture was extracted with EtOAc and the combined extracts were dried (Na$_2$SO$_4$), filtered and concentrated. Flash chromatography (SiO$_2$, 1:1 to 0:1 Heptane/EtOAc) afforded Example 277A (53 mg, 91%). HPLC R$_t$=3.20 min. m/z=266 [M+H$^+$].

Example 277

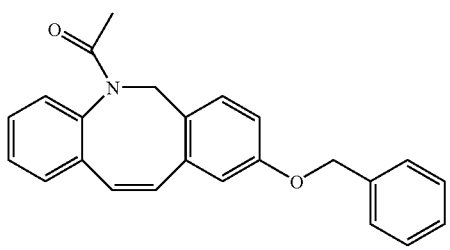

A mixture of Example 277A (10 mg, 0.038 mmol), K$_2$CO$_3$ (16 mg, 0.12 mmol) and benzylchloride (0.013 mL, 0.11 mmol) in DMF (0.25 mL) was stirred at room temperature under argon. Upon completion, the crude mixture was purified by reversed-phase HPLC to afford Example 277 (8.4 mg, 63%). HPLC R$_t$=4.35 min. m/z=356 [M+H$^+$].

Examples 278 to 281

The compounds found in Table 24 were prepared according to the procedures described in Example 277.

Example 282

5-Acetyl-5,6-dihydro-9-[(methylsulfonyl)methoxy]-dibenz[b,f]azocine

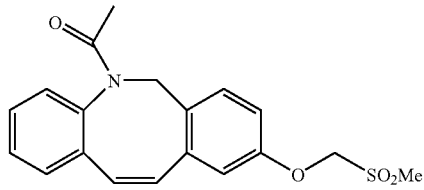

A solution of Example 280 (3.3 mg, 0.010 mmol) in CH$_2$Cl$_2$ (2 mL) at 0° C. was treated with mCPBA (10 mg) and stirred for two hours at 0° C. A small amount of 3M NaOH was added and stirring was continued at 0° C. The reaction mixture was dried (Na$_2$SO$_4$), filtered and concentrated. The crude product was purified by flash chromatography (SiO$_2$, 1:1 to 0:1 Heptane/EtOAc) to afford Example 282 as a white solid (3.4 mg, 96%). HPLC R$_t$=3.16 min. m/z=358 [M+H$^+$].

TABLE 24

| Example No. | R | Compound name | [M + H] | HPLC Ret Time (min) |
|---|---|---|---|---|
| 278 | ⟨CH(CH$_3$)C(O)OMe⟩ | [(5-Acetyl-5,6-dihydrodibenz[b,f]azocin-9-yl)oxy]-acetic acid methyl ester | 360[M+ Na$^+$] | 3.48 |
| 279 | ⟨(CH$_2$)$_3$OH⟩ | 3-[(5-Acetyl-5,6-dihydrodibenz[b,f]azocin-9-yl)oxy]-1-propanol | 324 | 3.46 |
| 280 | ⟨CH$_2$SMe⟩ | 5-Acetyl-5,6-dihydro-9-[(methylthio)methoxy]-dibenz[b,f]azocine | 326 | 3.88 |
| 281 | ⟨CH$_2$-4-pyridyl⟩ | 5-Acetyl-5,6-dihydro-9-(4-pyridinylmethoxy)-dibenz[b,f]azocine | 3.57 | 2.86 |

Example 283

5-Acetyl-2-chloro-9-(4,5-dihydro-5-oxo-1,3,4-oxa-diazol-2-yl)-5,6-dihydrodibenz[b,f]azocine

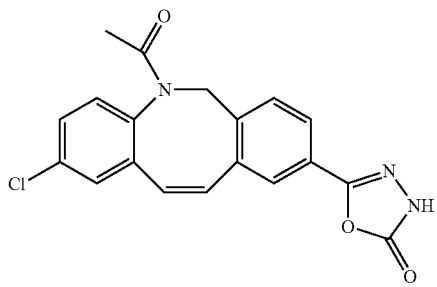

283A

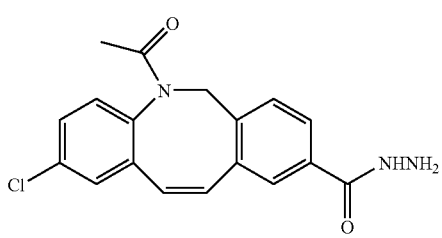

To a mixture of Example 259A (200 mg, 0.61 mmol), hydrazine (29 µl, 0.92 mmol) and Et$_3$N (123 mg, 1.22 mmol) in a mixed solvent of CH$_2$Cl$_2$ (5 mL) and THF (1 mL) was added EDCI (175 mg, 0.92 mmol). The mixture was stirred at room temperature for 3 hours. The solution was concentrated and the residue was purified by flash chromatography (SiO$_2$, 5% to 10% MeOH/CH$_2$Cl$_2$) to give Example 283A (140 mg, 67%) as a white solid.

Example 283

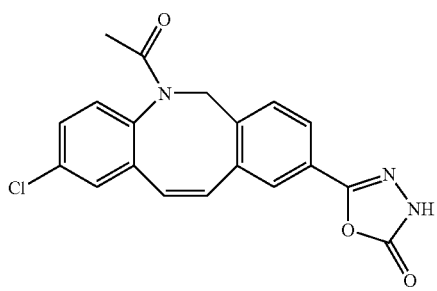

To a solution of Example 283A (30 mg, 0.088 mmol) in THF (2 mL) was added Et$_3$N (16 µl, 0.11 mmol) followed by CDI (36 mg, 0.22 mmol). The reaction mixture was stirred at room temperature for 2 hours, concentrated and the residue was purified by preparative reversed-phase HPLC to give Example 283 (6.5 mg, 20%) as a white solid. HPLC R$_f$=2.11 (b) min. m/z=368 (M+H$^+$).

Example 284

5-Acetyl-2-chloro-5,6-dihydro-9-(1,3,4-oxadiazol-2-yl)dibenz[b,f]azocine

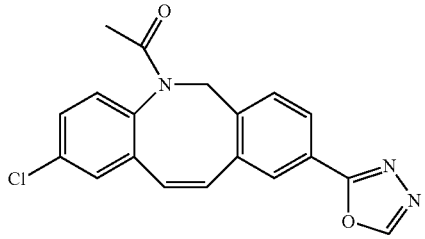

To a solution of Example 283A (30 mg, 0.088 mmol) in EtOH (1 mL) was added (EtO)$_3$CC$_2$H$_5$ (1.0 mL) followed by p-TsOH (2 mg, 0.01 mmol). The reaction mixture was heated at 100° C. for 1 h. The resulting solution was concentrated under high vacuum and the residue was purified by preparative reversed-phase HPLC to give Example 284 (10 mg, 32%). HPLC R$_f$=2.04(b) min. m/z=352 (M+H$^+$).

Example 285

5-Acetyl-2-chloro-9-(5-ethyl-1,3,4-oxadiazol-2-yl)-5,6-dihydro-dibenz[b,f]azocine

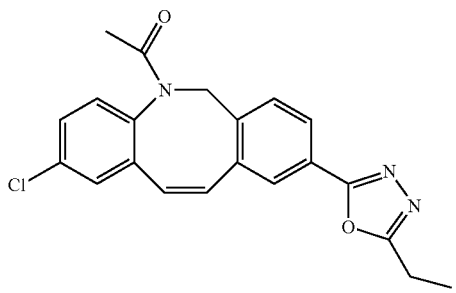

To a solution of Example 283A (30 mg, 0.088 mmol) in EtOH (1 mL) was added (EtO)$_3$CC$_2$H$_5$ (1.2 mL) followed by p-TsOH (2 mg, 0.01 mmol). The reaction mixture was heated at 100° C. for 1 hour. The resulting solution was concentrated under high vacuum and the residue was purified by preparative reversed-phase HPLC to give Example 285 (23 mg, 70%). HPLC R$_f$=2.207(b) min. m/z=380 (M+H$^+$).

Example 286

5-Acetyl-2-chloro-9-(5-ethyl-1,3,4-oxadiazol-2-yl)-5,6,11,12-tetrahydro-dibenz[b,f]azocine

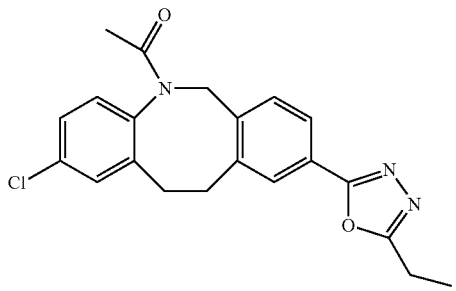

A mixture of Example 285 (10 mg, 0.026 mmol) and 5% Rh/C (5 mg) in MeOH (2 mL) was purged with $H_2$, then stirred at room temperature under a $H_2$ atmosphere overnight. The mixture was filtered and the filtrate was concentrated. The residue was taken up in MeOH (2 mL), and treated with 10% Pd/C (1 mg). The suspension was stirred under a $H_2$ atmosphere for 6 hours and filtered. The filtrate was concentrated and purified by preparative reversed-phase HPLC to give Example 286 (0.95 mg, 9.5%) HPLC $R_t$=2.14(b) min. m/z=382 (M+H$^+$).

Example 287

5-Acetyl-9-(butylsulfinyl)-5,6,11,12-tetrahydro-dibenz[b,f]azocine

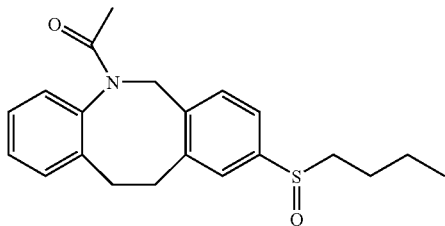

287A. 5-Acetyl-9-(butylthio)-5,6-dihydro-dibenz[b,f]azocine

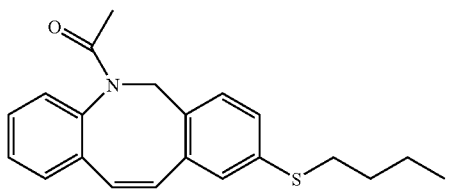

To a solution of Example 2 (150 mg, 0.46 mmol) in anhydrous DMSO (15 mL) was added Pd(PPh$_3$)$_4$ (27 mg, 0.023 mmol) and Butane-1-thiol (0.074 mL, 0.69 mmol) under an argon atmosphere. Potassium t-butoxide (0.7 mL, 0.69 mmol, 1M in THF) was added dropwise and the mixture was heated to 100° C. for 6 hours. The reaction mixture was cooled and partitioned between EtOAc and water. The aqueous layer was extracted with EtOAc (4×20 mL). The combined organic layers were washed with brine (2×20 mL), dried over Na$_2$SO$_4$, filtered and concentrated. The residue was purified by flash chromatography (SiO$_2$, 2:1 hexane/EtOAc) to give the title compound (95 mg, 61%). HPLC $R_t$=4.56 min. m/z=338 (M+H$^+$).

287B. 5-Acetyl-9-(butylsulfinyl)-5,6-dihydro-dibenz[b,f]azocine

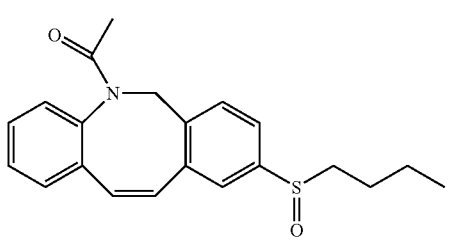

To a solution of compound Example 287A (32 mg, 0.095 mmol) in CH$_2$Cl$_2$ (5 mL) at 0° C. was added mCPBA (13 mg, 0.05 mmol). The solution was stirred for 1 hour at 0° C. and for 1 hour at room temperature. The reaction was quenched by adding NaHCO$_3$ solution. The aqueous layer was extracted with EtOAc (3×2 mL). The combined EtOAc extracts were washed with brine and dried over Na$_2$SO$_4$, filtered and concentrated. The residue was purified by flash chromatography (SiO$_2$, 2:1 hexane/EtOAc) to give the title compound (24 mg, 77 %). HPLC $R_t$=3.7 min. m/z=354(M+H$^+$).

Example 287

5-Acetyl-9-(butylsulfinyl)-5,6,11,12-tetrahydro-dibenz[b,f]azocine

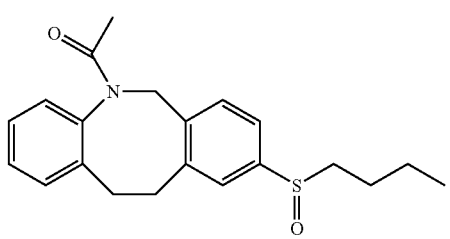

To a solution of compound Example 287B (8 mg, 0.023 mmol) in MeOH (5 mL) was added Pd(OH)$_2$/C (26 mg). The mixture was stirred at room temperature under a hydrogen atmosphere for 2 hours. The solution was filtered through a nylon membrane filter, concentrated and purified by preparative HPLC to give the title compound (3 mg, 37%). HPLC $R_t$=3.517 min. m/z=356(M+H$^+$).

Example 288

5-Acetyl-5,6,11,12-tetrahydro-N-2-pyridinyl-dibenz[b,f]azocin-9-amine

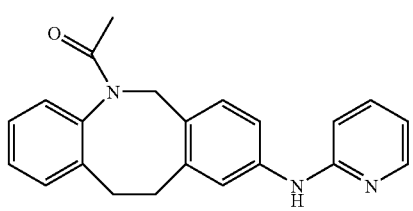

288A

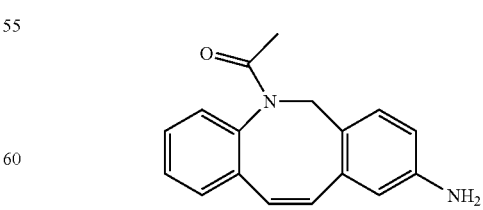

To a solution of Pd$_2$(dba)$_3$ (70 mg, 0.076 mmol) in toluene(5 mL) under argon was added BINAP (143 mg, 0.22 mmol) followed by Example 2 (100 mg, 0.31 mmol), benzophenone imine (61 µl, 0.37 mmol) and sodium ethoxide (41 mg, 0.43 mmol). The resulting red solution was stirred at 100° C. for 2 hours. The mixture was cooled to room temperature and concentrated. The residue was dissolved in THF (5 mL) and treated with 1N HCl at room temperature for 24 hours. The resulting mixture was concentrated, dissolved in MeOH (5 mL), filtered and concentrated. The residue was partitioned between EtOAc and 0.1N HCl (1:1, 20 mL). The aqueous layer was extracted with EtOAc (2×20 mL). The combined EtOAc extracts were washed with brine and dried over $Na_2SO_4$, filtered and concentrated to give Example 288A (53 mg, 65%) as a yellow oil.

288B. Preparation of 5-Acetyl-5,6-dihydro-N-2-pyridinyl-dibenz[b,f]azocin-9-amine

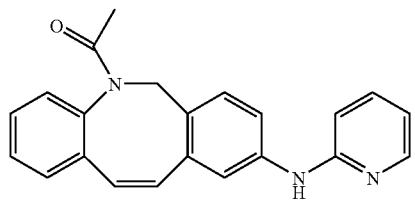

To a solution compound Example 288A (25 mg, 0.09 mmol) in toluene (2 mL) under argon was added sodium ethoxide (12 mg, 0.13 mmol), dppp (15 mg, 0.036 mmol), 2-bromopyridine (9 μl, 0.09 mmol) followed by $Pd_2(dba)_3$. The solution was heated to 70° C. for 1 hour. The reaction mixture was cooled, diluted with EtOAc (20 mL) and washed with brine (20 mL). The organic layer was dried over $Na_2SO_4$, filtered and concentrated. The residue was purified by flash chromatography ($SiO_2$, 1:1 hexane/EtOAc) to give the title compound (15 mg, 47%).

Example 288

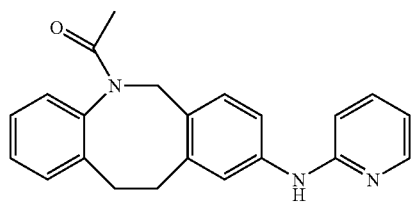

A solution of compound Example 288B (14 mg, 0.041 mmol) and 10% Pd-C (10 mg) in THF (2 mL) was stirred under a hydrogen atmosphere for 24 hours. The reaction was filtered and concentrated. The residue was purified by flash chromatography ($SiO_2$, 100% $CH_2Cl_2$) to give the title compound (3.2 mg, 23%). HPLC $R_t$=1.54 (b) min. m/z=344 $(M+H^+)$.

Example 289

5-Acetyl-2-chloro-5,6-dihydro-9-(1H-pyrrol-1-yl)-dibenz[b,f]azocine

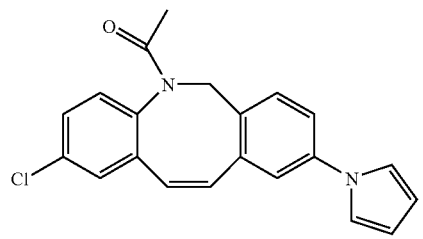

To a solution of Example 3 (30 mg, 0.08 mmol), in dioxane (0.5 mL) was added 1H-pyrrole (5.7 μl), copper iodide (15 mg), cesium carbonate (56.8 mg), and cyclohexane-1,2-diamine (0.94 mg). The solution was heated to 110° C. for 30 minutes. The reaction mixture was cooled to room temperature and concentrated. The residue was dissolved in MeOH, filtered and purified by preparative reversed-phase HPLC to give the title compound (11 mg, 38%).

Example 290

5-Acetyl-2-chloro-5,6,11,12-tetrahydro-9-(1H-pyrrol-1-yl)-dibenz[b,f]azocine

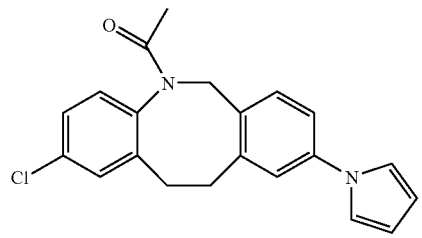

A solution of compound Example 289 (9 mg, 0.02 mmol) and 5% Rh/C (4 mg) in MeOH (3 mL) was stirred under a hydrogen atmosphere for 3 hours. The reaction was filtered and purified by preparative HPLC to give the title compound (1.2 mg, 13%). HPLC $R_t$=3.95 min. m/z=351 $(M+H^+)$.

Example 291

5-Acetyl-2-chloro-5,6,11,12-tetrahydro-9-(1-pyrrolidinyl)-dibenz[b,f]azocine

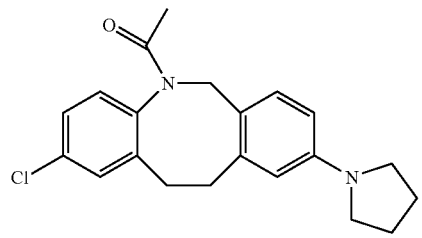

A solution of compound Example 289 (9 mg, 0.02 mmol) and 5% Rh/C (4 mg) in MeOH (3 mL) was stirred under a hydrogen atmosphere for 3 hours. The reaction was filtered and purified by preparative HPLC to give the title compound (3.4 mg, 38%). HPLC $R_t$=3.78 min. m/z=355 (M+H$^+$).

Example 292

5-Acetyl-5,6-dihydro-9-(4-methyl-2-oxazolyl)-dibenz[b,f]azocine

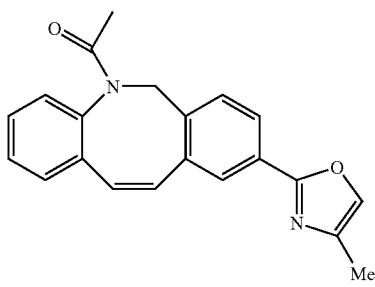

292A

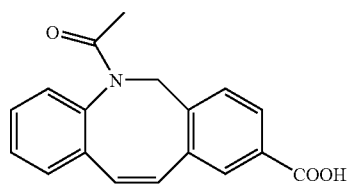

To a solution of Example 266 (0.75 g, 2.15 mmol) in EtOH (40 mL) and H$_2$O (8 mL) was added potassium hydroxide (1.6 g). The reaction was stirred at room temperature for 1.5 hours. The solution was concentrated and acidified with saturated aqueous NaHCO$_3$ followed by stirring with H$_2$O (20 mL) and EtOAc (80 mL). The solid obtained was filtered and washed with EtOAc. The aqueous layer was extracted with EtOAc. The combined organic solution was dried and concentrated. The residue was boiled in a 1:1 solution of EtOAc: hexane to give Example 292A (640 mg, 99%).

292B

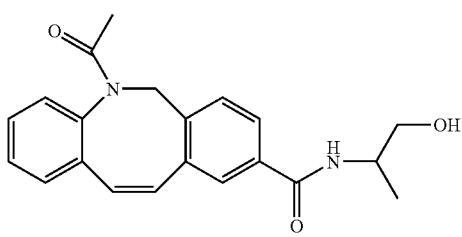

To a solution of compound Example 292A (100 mg, 0.34 mmol) in DMF (1 mL) was added 2-amino-propan-1-ol (128 mg, 1.7 mmol), HOBt (68 mg, 0.44 mmol) and EDAC (310 mg, 1.61 mmol). The solution was stirred at 60° C. for 3.5 hours. The solution was cooled to room temperature and partitioned between water and EtOAc. The aqueous layer was extracted with EtOAc (20 mL) and the combined organic layers were washed with 0.5N NaOH (20 mL), dried (Na$_2$SO$_4$) and concentrated. The residue was purified by flash chromatography (SiO$_2$, 100% EtOAc) to give Example 292B (106 mg, 89%).

292C

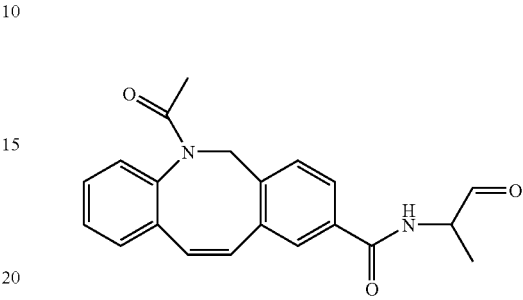

To a solution of oxalyl chloride (0.3 mL, 0.57 mmol, 2M in CH$_2$Cl$_2$) in CH$_2$Cl$_2$ (1 mL) at −78° C. was added DMSO (0.1 mL, 1.4 mmol). After 5 minutes of stirring, a solution of compound Example 292B (100 mg, 0.28 mmol) in CH$_2$Cl$_2$ (5 mL) was added dropwise. The solution was stirred for 30 minutes followed by addition of TEA (0.32 mL, 0.25 mmol). The solution was first stirred at −78° C. for 10 minutes, then warmed to 0° C. and stirred for 20 minutes. Aqueous NaHCO$_3$ (1 mL) was then added. After stirring for a few minutes, the solution was extracted with EtOAc. The combined organic layers were dried (Na$_2$SO$_4$) and filtered through a silica pad to give Example 292C (86 mg, 87%).

Example 292

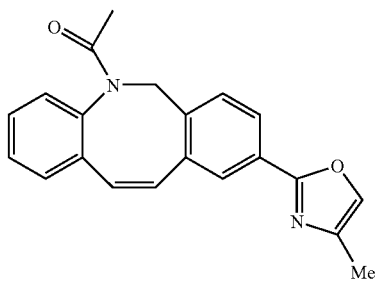

A mixture of compound Example 292C (86 mg, 0.25 mmol) and PPA (2 mL) was heated at 110° C. for 7 hours. The resulting solution was cooled to 0° C., EtOAc and ice were added with stirring followed by the addition of NH$_4$OH (1 mL). The aqueous layer was extracted with EtOAc, dried (Na$_2$SO$_4$), filtered and concentrated. The residue was purified by flash chromatography (SiO$_2$, 50% EtOAc/CH$_2$Cl$_2$) to give the title compound (20 mg, 24%). HPLC $R_t$=3.90 min. m/z=331 [M+H$^+$].

Example 293

5-Acetyl-5,6-dihydro-9-(5-methyl-2-oxazolyl)-dibenz[b,f]azocine

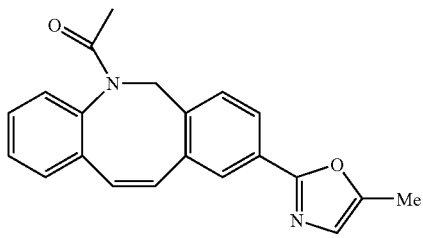

293A

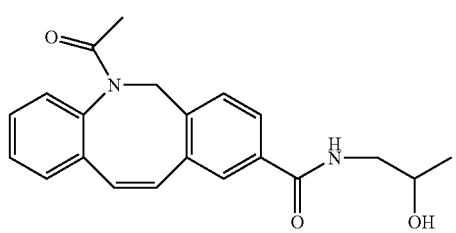

Example 293A (112 mg, 94%) was prepared from Example 292A (100 mg, 0.34 mmol) by a route similar to that used for the preparation of Example 292B.

293B

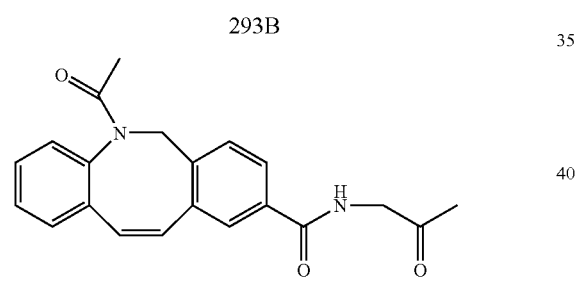

Example 293B (111 mg, 99%) was prepared from Example 293A (112 mg, 0.31 mmol) by a route similar to that used for the preparation of Example 292B.

Example 293

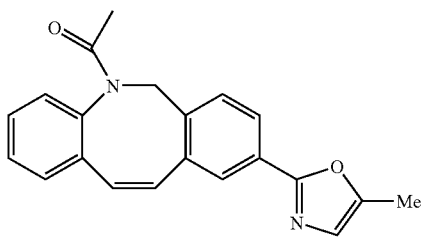

Example 293 (86 mg, 81%) was prepared from Example 293B (110 mg, 0.32 mmol) by a route similar to that used for the preparation of Example 292. HPLC $R_t$=3.92 min. m/z=331(M+H$^+$).

Example 294

5-Acetyl-5,6,11,12-tetrahydro-9-(5-methyl-2-oxazolyl)-dibenz[b,f]azocine

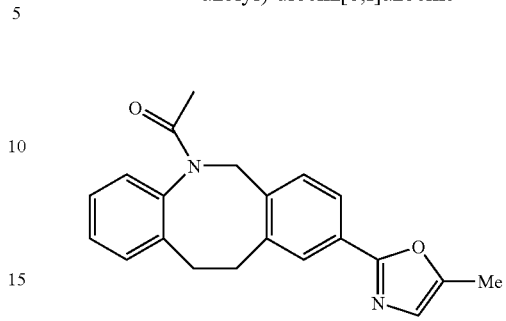

To a solution of Example 293 (50 mg, 0.15 mmol) in MeOH (10 mL) was added palladium hydroxide (16 mg). The solution was stirred under a hydrogen atmosphere for 3 hours. The mixture was filtered through a nylon membrane filter and concentrated to give the title compound as a white solid (43 mg, 87%). HPLC $R_t$=3.81 min. m/z=333(M+H$^+$).

Example 295

5-Acetyl-5,6-dihydro-9-(5-oxazolyl)-dibenz[b,f]azocine

A mixture of Example 2 (100 mg, 0.3 mmol), sodium formate (41 mg, 0.6 mmol) and PdCl$_2$(PPh$_3$)$_2$ (21 mg, 0.03 mmol) in DMF (2 mL), was purged with CO(g) for one hour and then heated to 110° C. under a constant stream of CO(g) through for 3 hours. The reaction mixture was diluted with water and extracted with EtOAc. The organic layer was washed with brine (1×100 mL), dried over Na$_2$SO$_4$, filtered and concentrated. The residue was dissolved in MeOH (5 mL). Tosylmethyl isocyanide (64 mg, 0.33 mmol) and potassium carbonate (46 mg, 0.33 mmol) were added and the mixture was heated to 80° C. for 3 hours. The reaction mixture was diluted with water and extracted with EtOAc (2×2 mL). The organic extracts were washed with brine (1×100 mL), dried over Na$_2$SO$_4$, filtered and concentrated. The crude material was purified by flash chromatography (SiO$_2$, 1:1 EtOAc/hexanes) to give the title compound (65 mg, 70%). HPLC $R_t$=3.66 min. m/z=317(M+H$^+$).

Example 296

5-Acetyl-5,6,11,12-tetrahydro-9-(5-oxazolyl)-dibenz[b,f]azocine

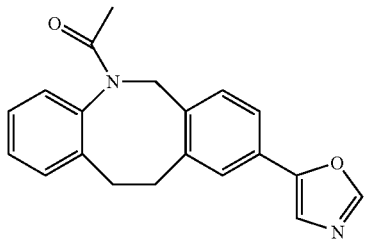

To a solution of Example 295 (50 mg, 0.16 mmol) in MeOH (10 mL) was added palladium hydroxide (25 mg). The solution was stirred under a hydrogen atmosphere for 3 hours. The mixture was filtered through a nylon membrane filter, concentrated and recrystallized from EtOAc/hexane to give the title compound as a white solid (35 mg, 69%). HPLC $R_t$=3.56 min. m/z=319(M+H$^+$).

Example 297

5-Acetyl-5,6-dihydro-9-[5-(1-methylethyl)-2-oxazolyl]-dibenz[b,f]azocine

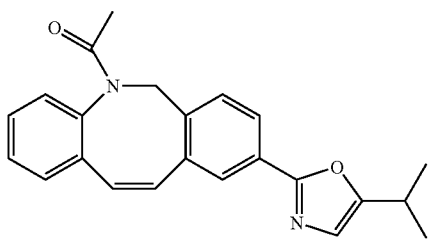

297A

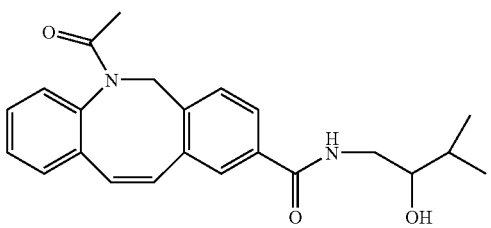

Example 297A (123 mg, 96%) was prepared from Example 292A (100 mg, 0.34 mmol) by a route similar to that used for the preparation of Example 292B.

297B

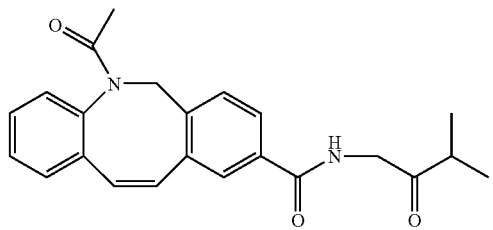

Example 297B (103 mg, 84%) was prepared from Example 297A (123 mg, 0.325 mmol) by a route similar to that used for the preparation of Example 292C Example 297

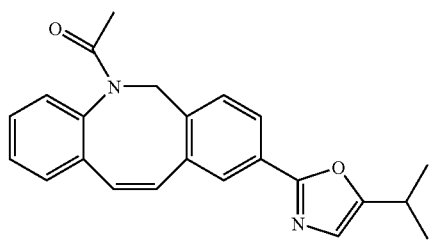

Example 297 (70 mg, 95%) was prepared from Example 297B (82 mg, 0.22 mmol) by a route similar to that used for the preparation of Example 292. HPLC $R_t$=4.29 min. m/z=361(M+H$^+$).

Example 298

5-Acetyl-5,6,11,12-tetrahydro-9-[5-(1-methylethyl)-2-oxazolyl]-dibenz[b,f]azocine

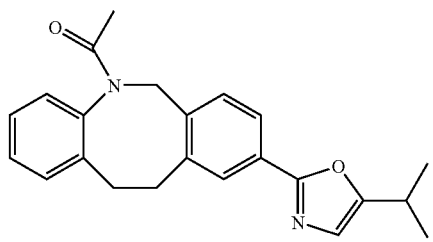

To a solution of Example 297 (43 mg, 0.11 mmol) in MeOH (10 mL) was added palladium hydroxide (16 mg). The solution was stirred under a hydrogen atmosphere for 3 hours. The mixture was filtered through a nylon membrane filter and concentrated to give the title compound as a white solid (41 mg, 95%). HPLC $R_t$=4.22 min. m/z=361 (M+H$^+$).

Example 299

2-(5-Acetyl-5,6-dihydrodibenz[b,f]azocin-9-yl)-5-oxazolepropanoic acid methyl ester

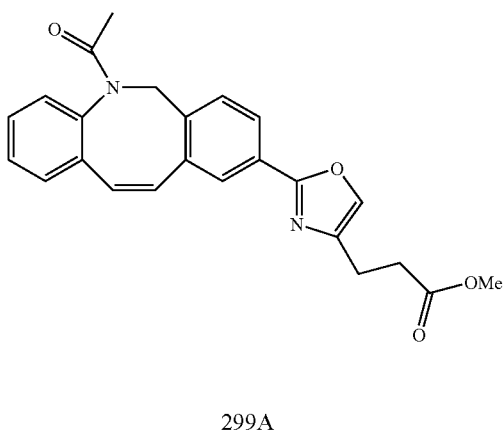

299A

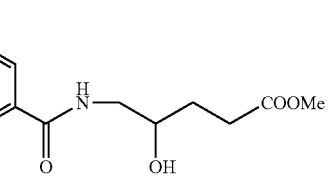

To a solution of Example 292A (110 mg, 0.23 mmol) at −15° C. in CH$_2$Cl$_2$ (5 mL) was added butyl chloroformate (0.15 mL, 1.2 mmol) followed by NMM (0.22 mL, 2.3 mmol). The mixture was stirred at −15° C. for 15 minutes and then 5-Amino-4-oxo-pentanoic acid methyl ester (210 mg, 1.2 mmol) was added. The solution was stirred at room temperature for 3 days. The reaction mixture was diluted with water and extracted with EtOAc (2×2 mL). The organic layer was washed with brine (1×100 mL), dried over Na$_2$SO$_4$, filtered and concentrated. The crude product was purified by flash chromatography (SiO$_2$, 1:1 EtOAc/hexanes) to give the Example 299A (55 mg, 57%).

Example 299

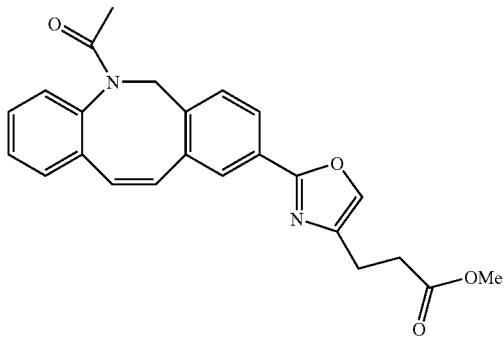

Example 299 (13 mg, 27%) was prepared from Example 299A (50 mg, 0.12 mmol) by a route similar to that used for the preparation of Example 292. HPLC R$_t$=3.65 min. m/z=403(M+H$^+$).

Example 300

5-Acetyl-5,6,11,12-tetrahydro-12-(methylsulfonyl)-dibenzo[b,f][1,4]diazocine

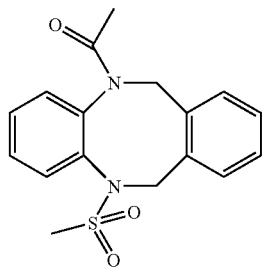

A solution of 1-(11,12-Dihydro-6H-dibenzo[b,f][1,4]diazocin-5-yl)-ethanone (10 mg, 0.04 mmol) in CH$_2$Cl$_2$ (1 mL) was treated with methanesulfonyl chloride (6.8 mg, 0.06 mmol), DMAP (0.5 mg, 0.004 mmol) and Et$_3$N (6.0 mg, 0.06 mmol). The reaction mixture was stirred at room temperature for 3 hours, concentrated and purified by preparative reversed-phase chromatography to afford Example 300 (4.2 mg, 32%). HPLC R$_t$=2.63 min. m/z=331 (M+H$^+$).

Example 301

5-Acetyl-N,N-diethyl-5,6,11,12-tetrahydro-dibenz[b,f]azocin-9-amine

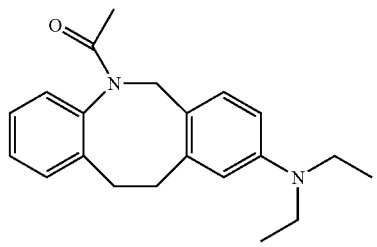

301A. 5-Acetyl-N,N-diethyl-5,6-dihydro-dibenz[b,f]azocin-9-amine

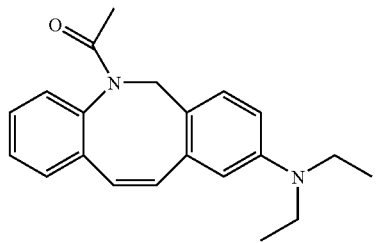

A mixture Example 2 (100 mg, 0.30 mmol) in toluene (2.5 mL) was treated with rac-BINAP (37 mg, 0.06 mmol), NaOtBu (72 mg, 0.75 mmol) and diethylamine (0.080 mL, 0.75 mmol). Pd(dba)$_2$ (17 mg, 0.03 mmol) was added and the reaction was heated to 110° C. under argon for 1.5 hours. The resulting mixture was cooled to room temperature and concentrated to a dark residue. The crude product was purified by flash chromatography (SiO$_2$, 10% EtOAc/CH$_2$Cl$_2$) to afford Example 301A as a yellow solid (30 mg, 31%). HPLC R$_t$=1.12(d) min. m/z=321 (M+H$^+$).

Example 301

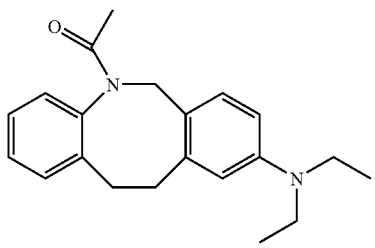

A solution of Example 301A (27 mg, 0.084 mmol) in MeOH (2 mL) was treated with 5% Rh/C (5.5 mg). The suspension was stirred under a H$_2$ atmosphere for 2 hours. Additional 5% Rh/C (5.5 mg) was added and the reaction was allowed to stir under a H$_2$ atmosphere for 16 hours. The resulting mixture was filtered to remove the catalyst and the filtrate was concentrated to provide Example 301 (27 mg, 100%). HPLC R$_t$=2.36 min. m/z=323.

Examples 302 to 314

The compounds found in Table 25 and Table 26 were prepared in a manner analogous to that described for Example 301.

TABLE 25

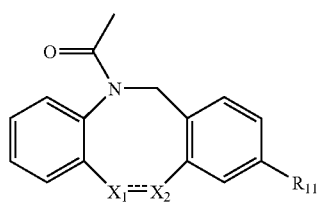

| Example No. | X$_1$==X$_2$ | R$_{11}$ | Compound name | [M + H] | HPLC Ret Time (min) |
|---|---|---|---|---|---|
| 302 | | HN-CH$_2$-piperidine-NBoc | 4-[[(5-Acetyl-5,6-dihydrodibenz[b,f]azocin-9-yl)amino]methyl]-1-piperidinecarboxylic acid, 1,1-dimethylethyl ester | 462 | 3.47 |
| 303 | | HN-CH$_2$-2-pyridyl | 5-Acetyl-5,6-dihydro-N-(2-pyridinylmethyl)-dibenz[b,f]azocin-9-amine | 356 | 2.03 |
| 304 | | HN-CH$_2$-2-furyl | 5-Acetyl-N-(2-furanylmethyl)-5,6-dihydro-dibenz[b,f]azocin-9-amine | 345 | 2.80 |
| 305 | | HN-CH$_2$-4-pyridyl | 5-Acetyl-5,6-dihydro-N-(4-pyridinylmethyl)-dibenz[b,f]azocin-9-amine | 356 | 2.02 |
| 306 | | HN-CH$_2$-3-pyridyl | 5-Acetyl-5,6-dihydro-N-(3-pyridinylmethyl)-dibenz[b,f]azocin-9-amine | 356 | 2.03 |
| 307 | | HN-CH$_2$-1,3-dioxolan-2-yl | 5-Acetyl-N-(1,3-dioxolan-2-ylmethyl)-5,6-dihydro-dibenz[b,f]azocin-9-amine | 351 | 2.67 |
| 308 | | HN-CH$_2$CH$_2$-OMe | 5-Acetyl-5,6-dihydro-N-(2-methoxyethyl)-dibenz[b,f]azocin-9-amine | 323 | 2.24 |

TABLE 25-continued

| Example No. | $X_1$---$X_2$ | $R_{11}$ | Compound name | [M + H] | HPLC Ret Time (min) |
|---|---|---|---|---|---|
| 309 | CH=CH | HN-CH2-cyclopropyl | 5-Acetyl-N-(cyclopropylmethyl)-5,6-dihydro-dibenz[b,f]azocin-9-amine | 319 | 2.20 |
| 310 | CH=CH | HN-CH2-phenyl | 5-Acetyl-5,6-dihydro-N-(phenylmethyl)-dibenz[b,f]azocin-9-amine | 355 | 3.06 |
| 311 | CH=CH | pyrrolidinyl | 5-Acetyl-5,6-dihydro-9-(1-pyrrolidinyl)-dibenz[b,f]azocine | 319 | 3.28 |
| 312 | CH2-CH2 | pyrrolidinyl | 5-Acetyl-5,6,11,12-tetrahydro-9-(1-pyrrolidinyl)-dibenz[b,f]azocine | 321 | 2.75 |

TABLE 26

| Example No. | $X_1$---$X_2$ | $R_{10}$ | Compound name | [M + H] | HPLC Ret Time (min) |
|---|---|---|---|---|---|
| 313 | CH=CH | pyrrolidinyl | 5-Acetyl-2-chloro-5,6-dihydro-8-(1-pyrrolidinyl)-dibenz[b,f]azocine | 353 | 4.12 |
| 314 | CH=CH | HN-CH2-phenyl | 5-Acetyl-2-chloro-5,6-dihydro-N-(phenylmethyl)-dibenz[b,f]azocin-8-amine | 389 | 3.86 |

Example 315

5-Acetyl-5,6-dihydro-N-(4-piperidinylmethyl)-dibenz[b,f]azocin-9-amine

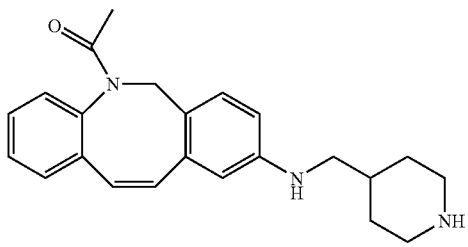

A solution of Example 302 (16.4 mg, 0.036 mmol) in CH$_2$Cl$_2$ (0.2 mL) was treated with trifluoroacetic acid (0.5 mL) and stirred for 30 minutes. Th resulting solution was concentrated, diluted with MeOH and filtered. The product was purified by reversed-phase HPLC to afford Example 315 (7.9 mg, 62%). HPLC R$_t$=1.89 min. m/z=362 (M+H$^+$)

Example 316

5-Acetyl-5,6,11,12-tetrahydro-N-(phenylmethyl)-dibenz[b,f]azocin-9-amine

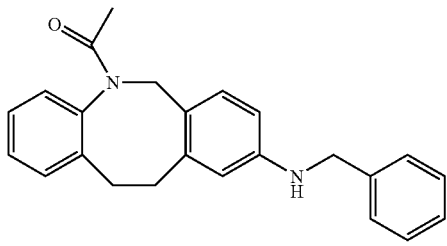

316A. (5-Acetyl-5,6,11,12-tetrahydrodibenz[b,f]azocin-9-yl)-carbamic acid, 1,1-dimethylethyl ester

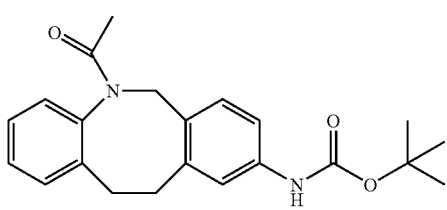

A clear solution of Example 270A (150 mg, 0.51 mmol), DIEA (0.11 mL, 0.61 mmol) in tBuOH (6 mL) was treated with diphenylphosphorylazide (0.14 mL, 0.61 mmol). The resulting solution was heated to 100° C. for 16 hours, cooled to room temperature and concentrated. The resulting residue was partitioned between water and EtOAc. The organic layer was dried (Na$_2$SO$_4$), filtered and concentrated. Flash chromatography (SiO$_2$, 1:1 Heptane/EtOAc) afforded the desired compound as a yellow solid (161 mg, 86%). HPLC R$_t$=3.92 min. m/z=367.

316B. 5-Acetyl-5,6,11,12-tetrahydro-dibenz[b,f]azocin-9-amine

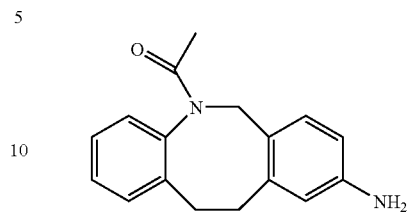

A solution of Example 316A (150 mg, 0.41 mmol) in CH$_2$Cl$_2$ (12 mL) was treated with trifluoroacetic acid (6 mL) and stirred at room temperature for 2 hours. The mixture was concentrated, taken up in EtOAc and washed with saturated aqueous NaHCO$_3$ solution. The organic layer was dried (Na$_2$SO$_4$), filtered and concentrated. Flash chromatography (SiO$_2$, 2:1 to 0:1 Heptane/EtOAc) afforded Example 316B (79 mg, 72%). HPLC R$_t$=2.13 min. m/z=267.

Example 316

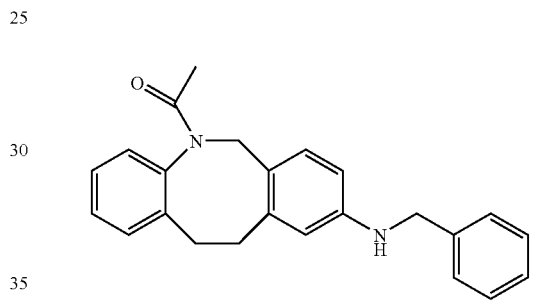

A solution of Example 316B (13 mg, 0.049 mmol) in dichloroethane (10 mL) under an argon atmosphere was treated with NaBH(OAc)$_3$ (17 mg) and benzaldehyde (0.005 mL). The reaction was stirred at room temperature overnight. Additional NaBH(OAc)$_3$ and benzaldehyde were added and stirring was continued for 5 hours. Saturated aqueous NaHCO$_3$ (1 mL) was added, the organic layer was dried (Na$_2$SO$_4$) and the mixture was concentrated. The product was purified by reversed-phase HPLC to afford 316 was a white solid (17 mg, 74%). HPLC R$_t$=3.24 min. m/z=357.

Example 317

N-(5-Acetyl-5,6,11,12-tetrahydrodibenz[b,f]azocin-9-yl)-benzamide

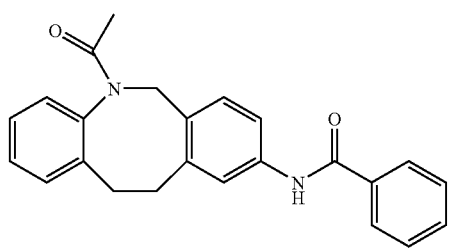

A solution of Example 316B (10 mg, 0.038 mmol) in CH$_2$Cl$_2$ (2 mL) was treated with pyridine (0.01 mL) and benzoylchloride (0.01 mL). The reaction was stirred under argon at room temperature, then quenched with saturated aqueous NaHCO₃ (1 mL). The aqueous layer was extracted with CH₂Cl₂ and the combine organic layers were dried (Na₂SO₄). The solution was passed through a short column of silica (100% EtOAc) and concentrated to afford Example 317 as a white solid (11 mg, 78%). HPLC $R_t$=3.68 min. m/z=371.

Example 318

N-(5-Acetyl-5,6,11,12-tetrahydrodibenz[b,f]azocin-9-yl)-acetamide

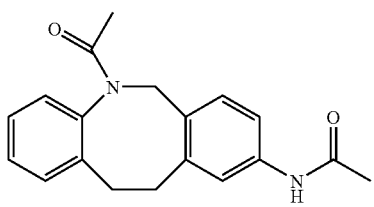

Example 318 was prepared in a manner analogous to Example 317. HPLC $R_t$=3.05 min. m/z=309.

Example 319

5-Acetyl-5,6,11,12-tetrahydro-9-(4-piperidinyl)-dibenz[b,f]azocine

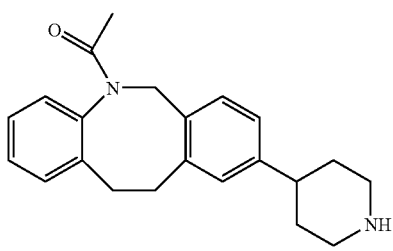

A solution of Example 125 (20 mg, 0.06 mmol) in AcOH (5 mL) was treated with PtO₂ (3 mg) and stirred under a H₂ atmosphere at room temperature for 1.5 hours. The reaction was filtered from catalyst and concentrated to afford Example 319 (4.5 mg, 18%). HPLC $R_t$=2.64 min. m/z=335.

Example 320

5-Acetyl-2-chloro-5,6,11,12-tetrahydro-9-(4-piperidinyl)-dibenz[b,f]azocine

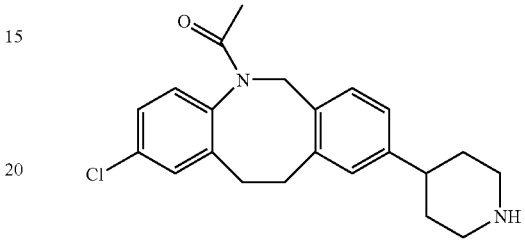

Example 320 (30 mg, 69%) was prepared from Example 139 (43 mg, 0.09 mmol) in a manner analogous to Example 319. HPLC $R_t$=2.92 min. m/z=369.

Example 321

5-Acetyl-9-(diethylnitroryl)-5,6,11,12-tetrahydro-dibenz[b,f]azocine

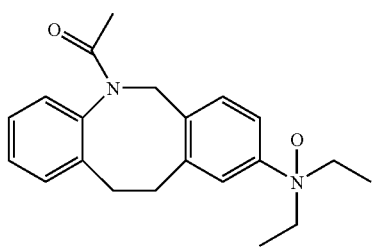

A clear solution of Example 301 (13 mg, 0.04 mmol) in CH₂Cl₂ (5 mL) was treated with mCPBA (17 mg, 0.06 mmol) at room temperature for two hours. The reaction mixture was concentrated and the product was purified by reversed-phase HPLC and free based with saturated aqueous NaHCO₃ to afford Example 321 (10 mg, 74%). HPLC $R_t$=2.58 min. m/z=339.

Examples 322 to 323

The compounds found in Table 27 were prepared according to the procedures described in Example 321.

TABLE 27

| Example No. | $X_1\text{---}X_2$ | $R_{11}$ | Compound name | [M + H] | HPLC Ret Time (min) |
|---|---|---|---|---|---|
| 322 | (pyrrolidine ring fragment) | 1-oxido-pyrrolidinyl | 5-Acetyl-5,6,11,12-tetrahydro-9-(1-oxido-1-pyrrolidinyl)-dibenz[b,f]azocine | 337 | 1.80 |
| 323 | (pyrrolidine ring fragment with double bond) | 1-oxido-pyrrolidinyl | 5-Acetyl-5,6-dihydro-9-(1-oxido-1-pyrrolidinyl)-dibenz[b,f]azocine | 335 | 1.88 |

Example 324

5-Acetyl-5,6-dihydro-dibenz[b,f]azocine-9-carbonitrile

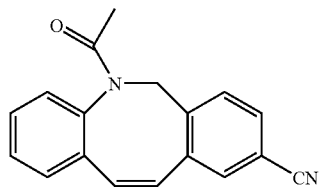

Example 2 (24 mg, 0.073 mmol), Pd(PPh$_3$)$_4$ (17 mg, 0.015 mmol), Zn(CN)$_2$ (5 mg, 0.044 mmol) and DMF (1.5 mL) were stirred under an argon atmosphere at 95° C. one hour. The reaction mixture was cooled to room temperature and diluted with MeOH, filtered and concentrated. The crude residue was purified by preparative reversed-phase HPLC to afford Example 324 (15 mg, 75%). HPLC R$_t$=2.83 min. m/z=275 (M+H$^+$)

Example 325

5-Acetyl-5,6-dihydro-dibenz[b,f]azocine-8-carbonitrile

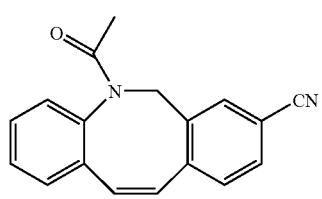

Example 325 was prepared in a manner similar to Example 324 starting with Example 15. HPLC R$_t$=2.81 min. m/z=275 (M+H$^+$).

Example 326

2-chloro-5-(cyclopropylcarbonyl)-5,6-dihydro-9-phenyl-dibenz[b,f]azocine

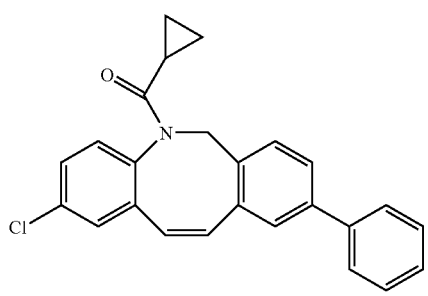

326A. 9-bromo-2-chloro-5-(cyclopropylcarbonyl)-5,6-dihydro-dibenz[b,f]azocine

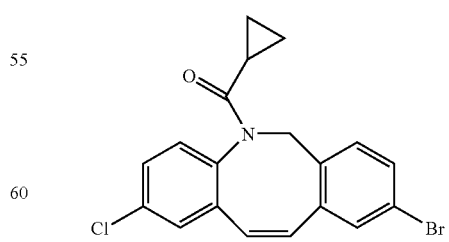

A solution of 9-Bromo-2-chloro-5,6-dihydro-dibenzo[b,f]azocine (30 mg, 0.09 mmol) (prepared in a manner analogous to that described for Example 1F) in dichloroethane was treated with pyridine (0.02 mL, 0.27 mmol) and cyclopropanecarbonyl chloride (0.011 mL, 0.12 mmol). The reaction mixture was stirred at room temperature for two hours then concentrated, diluted with MeOH and filtered. The crude product was purified by preparative reversed-phase HPLC to afford Example 326A (30 mg, 82%). HPLC $R_t$=4.05 min. m/z=388 (M+H$^+$)

Example 326

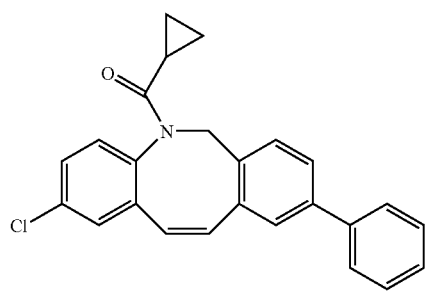

Example 326 was prepared from Example 326A according to the method described in Example 23. HPLC $R_t$=4.24 min. m/z=386 (M+H$^+$)

Examples 327 to 329

The compounds found in Table 28 were prepared according to the procedure described for Example 326 starting from the appropriate materials.

Example 330

2-chloro-5,6-dihydro-9-(6-methoxy-3-pyridinyl)-5-(methylsulfonyl)-dibenz[b,f]azocine

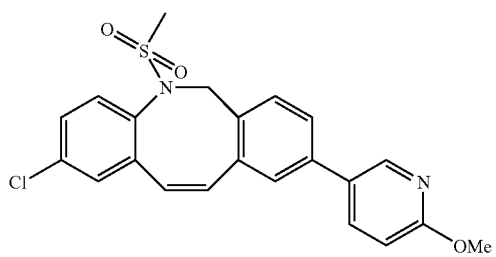

TABLE 28

| Example No. | $R_{10}$ | $R_{11}$ | Compound name | [M + H] | HPLC Ret Time (min) |
|---|---|---|---|---|---|
| 327 | H | 6-methoxy-3-pyridinyl | 2-chloro-5-(cyclopropylcarbonyl)-5,6-dihydro-9-(6-methoxy-3-pyridinyl)-dibenz[b,f]azocine | 417 | 4.01 |
| 328 | Br | H | 8-bromo-2-chloro-5-(cyclopropylcarbonyl)-5,6-dihydro-dibenz[b,f]azocine | 398 | 3.99 |
| 329 | 2-acetylphenyl | H | 8-(2-Acetylphenyl)-2-chloro-5-(cyclopropylcarbonyl)-5,6-dihydro-dibenz[b,f]azocine | 428 | 3.92 |

330A. 9-bromo-2-chloro-5,6-dihydro-5-(methylsulfonyl)-dibenz[b,f]azocine

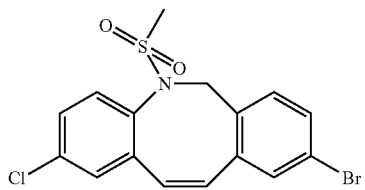

A solution of 9-Bromo-2-chloro-5,6-dihydro-dibenzo[b,f]azocine (30 mg, 0.09 mmol) (prepared in a manner analogous to that described for Example 1F) in dichloroethane was treated with pyridine (0.02 mL, 0.27 mmol) and methanesulfonyl chloride (0.009 mL, 0.12 mmol). The reaction mixture was stirred at room temperature for two hours then concentrated, diluted with MeOH and filtered. The crude product was purified by preparative reversed-phase HPLC to afford Example 330A (16 mg). HPLC $R_t$=3.66 min. m/z=398 (M+H$^+$)

Example 330

2-chloro-5,6-dihydro-9-(6-methoxy-3-pyridinyl)-5-(methylsulfonyl)-dibenz[b,f]azocine

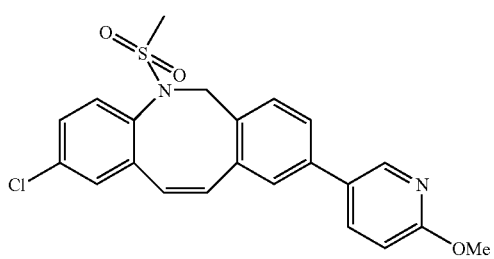

Example 330 as prepared from Example 330 according to the method described in Example 23A. HPLC $R_t$=3.64 min. m/z=427 (M+H$^+$)

Examples 331 to 332

The compounds found in Table 29 were prepared according to the procedure described for Example 330 starting from the appropriate materials.

TABLE 29

| Example No. | $R_{10}$ | $R_{11}$ | Compound name | [M + H] | HPLC Ret Time (min) |
|---|---|---|---|---|---|
| 331 | Br | H | 8-bromo-2-chloro-5,6-dihydro-5-(methylsulfonyl)-dibenz[b,f]azocine | 398 | 3.62 |
| 332 | (2-acetylphenyl group) | H | 8-(2-Acetylphenyl)-2-chloro-5,6-dihydro-5-(methylsulfonyl)-dibenz[b,f]azocine | 438 | 3.59 |

Example 333

2-chloro-9-phenyl-dibenz[b,f]azocine-5(6H)-carboxamide

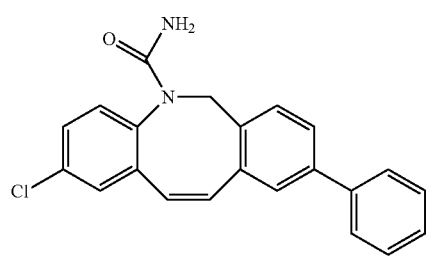

333A. 9-bromo-2-chloro-dibenz[b,f]azocine-5(6H)-carboxamide

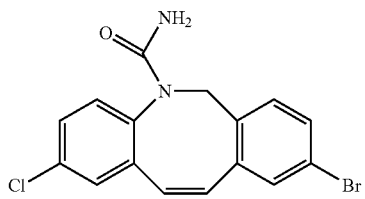

A solution of 9-Bromo-2-chloro-5,6-dihydro-dibenzo[b,f]azocine (30 mg, 0.09 mmol) (prepared in a manner analogous to that described for Example 1F) in dichloroethane was treated with pyridine (0.02 mL, 0.27 mmol) and phenyl isocyanatoformate (0.016 mL, 0.12 mmol). The reaction mixture was stirred at room temperature for two hours then treated with aqueous 1M NaOH (0.3 mL) for 15 minutes. The resulting mixture was concentrated, diluted with MeOH and filtered. The crude product was purified by preparative reversed-phase HPLC to afford Example 334A (26 mg). HPLC $R_t$=3.59 min. m/z=363 (M+H$^+$)

Example 334

2-chloro-9-phenyl-dibenz[b,f]azocine-5(6H)-carboxamide

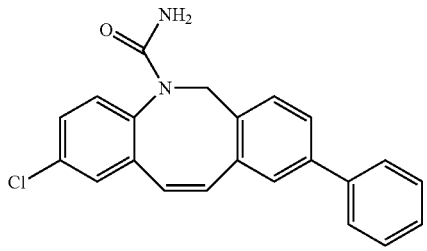

Example 334 was prepared from Example 334A according to the method described in Example 23A. HPLC $R_t$=3.86 min. m/z=361 (M+H$^+$)

Examples 335 to 337

The compounds found in Table 30 were prepared according to the procedure described for Example 334 starting from the appropriate materials.

TABLE 30

| Example No. | $R_{10}$ | $R_{11}$ | Compound name | [M + H] | HPLC Ret Time (min) |
|---|---|---|---|---|---|
| 335 | Br | H | 8-bromo-2-chloro-dibenz[b,f]azocine-5(6H)-carboxamide | 363 | 3.56 |
| 336 | 2-acetylphenyl | H | 8-(2-Acetylphenyl)-2-chloro-dibenz[b,f]azocine-5(6H)-carboxamide | 403 | 3.50 |
| 337 | H | 6-methoxy-3-pyridinyl | 2-chloro-9-(6-methoxy-3-pyridinyl)-dibenz[b,f]azocine-5(6H)-carboxamide | 392 | 3.56 |

Example 338

2-chloro-5,6-dihydro-9-(6-methoxy-3-pyridinyl)-5-(4-morpholinylsulfonyl)-dibenz[b,f]azocine

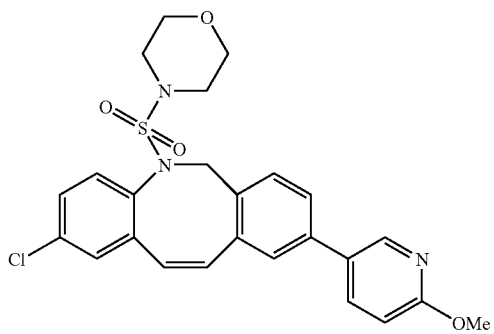

338A. 9-bromo-2-chloro-5,6-dihydro-5-(4-morpholinylsulfonyl)-dibenz[b,f]azocine

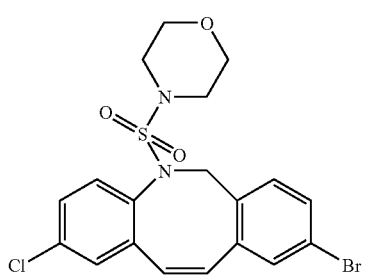

A solution of 9-Bromo-2-chloro-5,6-dihydro-dibenzo[b,f]azocine (30 mg, 0.09 mmol) (prepared in a manner analogous to that described for Example 1F) in dichloroethane was treated with pyridine (0.02 mL, 0.27 mmol) and morpholine-4-sulfonyl chloride (22 mg, 0.12 mmol). The reaction mixture was stirred at 100° C. for four hours then concentrated, diluted with MeOH and filtered. The crude product was purified by preparative reversed-phase HPLC to afford Example 338A (32 mg). HPLC $R_t$=3.89 min. m/z=469 (M+H$^+$)

Example 338

2-chloro-5,6-dihydro-9-(6-methoxy-3-pyridinyl)-5-(4-morpholinylsulfonyl)-dibenz[b,f]azocine

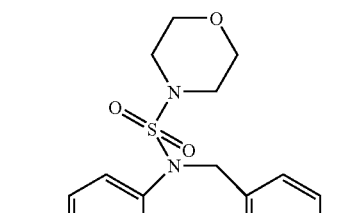

Example 338 was prepared from Example 338A according to the method described in Example 23A. HPLC $R_t$=3.90 min. m/z=498 (M+H$^+$)

Examples 339 to 340

The compounds found in Table 31 were prepared according to the procedure described for Example 338 starting from the appropriate materials.

TABLE 31

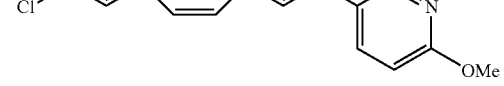

| Example No. | $R_{10}$ | $R_{11}$ | Compound name | [M + H] | HPLC Ret Time (min) |
|---|---|---|---|---|---|
| 339 | Br | H | 8-bromo-2-chloro-5,6-dihydro-5-(4-morpholinylsulfonyl)-dibenz[b,f]azocine | 469 | 3.89 |
| 340 | 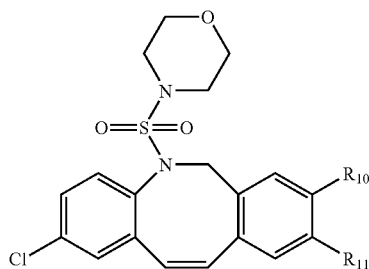 | H | 8-(2-Acetylphenyl)-2-chloro-5,6-dihydro-5-(4-morpholinylsulfonyl)-dibenz[b,f]azocine | 509 | 3.80 |

Example 341

9-bromo-11,12-dihydro-beta-oxo-dibenz[b,f]azocine-5(6H)-ethanamine

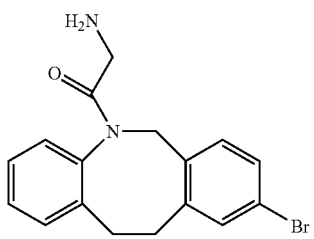

341A

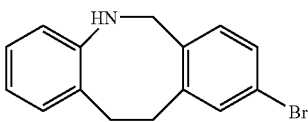

A solution of 9-Bromo-5,6-dihydro-dibenzo[b,f]azocine (prepare by the route described for Example 1F, starting from appropriate materials) (470 mg, 1.61 mmol) in MeOH (75 mL) was treated with 5% Rh/C (150 mg) under a $H_2$ atmosphere for 8 hours at room temperature. The resulting suspension was filtered to remove catalyst and the filtrate was concentrated. Flash chromatography ($SiO_2$, 8:1 then 4:1 then 2:1 Heptane/EtOAc) afforded Example 341A (300 mg, 65%).

Example 341

To a clear solution of Example 341A (20 mg, 0.069 mmol) and N-tButoxycarbonyl-glycine (25 mg, 0.14 mmol) in $CH_2Cl_2$ (2 mL) was added EDCI (33 mg, 0.17 mmol). The reaction mixture was stirred at room temperature for two hours, then filtered through a pad of silica, which was rinsed with EtOAc. The filtrate was concentrated and the residue was dissolved in TFA (1 mL) and stirred for one hour. The solvent was removed under reduced pressure and the residue treated with saturated aqueous $NaHCO_3$ and extracted with EtOAc. The organic extracts were dried ($Na_2SO_4$), filtered and concentrated to afford Example 341 as a yellow oil. (33 mg, 139%). HPLC $R_t$=2.50 min. (b) m/z=347 (M+H+).

Examples 342 to 345

The compounds found in Table 32 were prepared in a manner similar to Example 341, omitting the final TFA deprotection step.

TABLE 32

| Example No. | $R_9$ | Compound name | [M + H] | HPLC Ret Time (min) |
|---|---|---|---|---|
| 342 | cyclopropyl | 9-bromo-5-(cyclopropylcarbonyl)-5,6,11,12-tetrahydro-dibenz[b,f]azocine | 356 | 1.78(b) |
| 343 | benzyl | 9-bromo-5,6,11,12-tetrahydro-5-(phenylacetyl)-dibenz[b,f]azocine | 408 | 4.49 |
| 344 | ethyl | 9-bromo-5,6,11,12-tetrahydro-5-(1-oxopropyl)-dibenz[b,f]azocine | 346 | 4.22 |

TABLE 32-continued

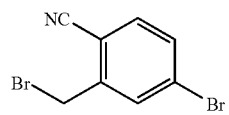

| Example No. | R₉ | Compound name | [M + H] | HPLC Ret Time (min) |
|---|---|---|---|---|
| 345 | 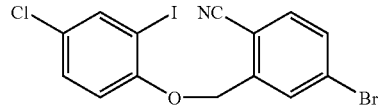 | 9-bromo-5,6,11,12-tetrahydro-5-(trifluoroacetyl)-dibenz[b,f]azocine | | 4.37 |

Example 346

9-bromo-11,12-dihydro-dibenz[b,f]azocine-5(6H)-carboxylic acid methyl ester

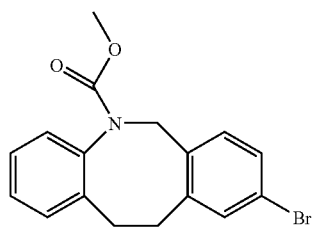

A solution of Example 341A (20 mg, 0.069 mmol) and pyridine (0.2 mmol) in CH₂Cl₂ (1 mL) was treated with methyl chlorofomate (0.015 mL, 0.2 mmol). The reaction was stirred at room temperature until complete. Saturated aqueous NaHCO₃ (0.1 mL) was added and stirring was continued for several minutes. The mixture was dried (Na₂SO₄), filtered and concentrated. Flash chromatography (SiO₂, 4:1 then 2:1 then 1:1 Heptane/EtOAc) afforded Example 346 (8 mg, 33%). HPLC R$_t$=4.21 min. m/z=370 [M+Na+].

Example 347

12-Acetyl-8-bromo-2-chloro-11,12-dihydro-6H-dibenz[b,f][1,4]oxazocine

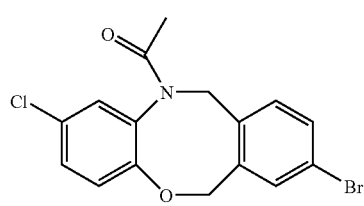

347A. Preparation of 4-Bromo-2-bromomethyl-benzonitrile

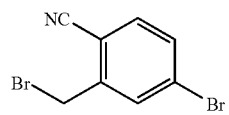

To a stirred mixture of 4-Bromo-2-methyl-benzonitrile (5.00 g, 25.5 mmol) in CCl₄ (40 mL) under argon was added N-bromosuccinamide (5.00 g, 28.1 mmol) and a catalytic amount of benzoyl peroxide. This mixture was heated at 85° C. for 2 days and cooled to room temperature. The precipitate was filtered off and the cake was rinsed with CCl₄ (2×10 mL). The filtrate was concentrated in vacuo to give 7.2 g crude 4-Bromo-2-bromomethyl-benzonitrile (quantitative yield) which was used without further purification.

347B. Preparation of 4-Chloro-2-iodo-phenol

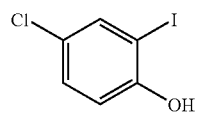

To 4-Chloro-2-iodo-1-methoxy-benzene (5.00 g, 18.6 mmol) in an ice bath under argon was added dropwise neat BBr₃ (2.20 mL, 23.2 mmol). This mixture was stirred at 0° C. for 3.5 hours and then quenched with MeOH (20 mL). This mixture was concentrated in vacuo to give 4.2 g of 4-Chloro-2-iodo-phenol in 88% yield. HPLC R$_t$=3.17 min (YMC S5 ODS column 4.6×50 mm, 10-90% aqueous methanol over 4 minutes containing 0.2% phosphoric acid, 4 mL/min, monitoring at 220 nm).

347C. Preparation of 4-Bromo-2-(4-chloro-2-iodo-phenoxymethyl)-benzonitrile

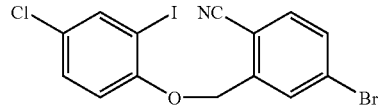

To a stirred mixture of 4-Bromo-2-bromomethyl-benzonitrile Example 347A (1.00 g, 3.64 mmol) and 4-Chloro-2-iodo-phenol Example 347B (0.94 g, 3.69 mmol) in dry DMF (8.0 mL) under argon was added 95% NaH (103 mg, 4.08 mmol). The reaction mixture was stirred at room temperature for 2.5 hours and quenched with water (30 mL). The resulting mixture was extracted with ether (180 mL). The organic layer was washed with water (1×30 mL), 1N NaOH solution (1×30 mL) and brine (1×30 mL). The organic layer was dried (MgSO$_4$), filtered and concentrated in vacuo to give 614 mg of crude 4-Bromo-2-(4-chloro-2-iodo-phenoxymethyl)-benzonitrile Example 347C which was used as is for the next transformation.

347D. Preparation of 5-Bromo-2-(4-chloro-2-iodo-phenoxymethyl)-benzylamine

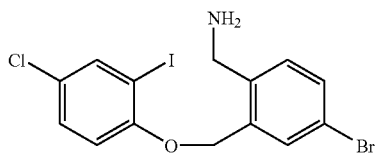

To a stirred mixture of 4-Bromo-2-(4-chloro-2-iodo-phenoxymethyl)-benzonitrile Example 347C (614 mg, 1.36 mmol) in anhydrous THF (4.0 mL) under argon was added dropwise 1M BH$_3$ in THF (5.40 mL, 5.40 mmol). The reaction mixture was heated at 80° C. for 40 minutes and cooled to room temperature. This mixture was quenched with water and concentrated in vacuo. The crude product was diluted with saturated NaHCO$_3$ solution (40 mL) and extracted with EtOAc (3×70 mL). The combined EtOAc extracts were washed with brine (1×30 mL), dried (MgSO$_4$), filtered and concentrated in vacuo to give 506 mg of crude product Example 347D. 90 mg of crude product Example 347D was purified by a Shimadzu auto prep HPLC, employing 30% to 100% 10 min gradient elution with 0.1% TFA in MeOH-water solvent system, 220 nM detection, 20 mL/min elution with a YMC ODS S5 20×100 mm column to give 25.9 mg of pure 5-Bromo-2-(4-chloro-2-iodo-phenoxymethyl)-benzylamine Example 347D. Calculated yield from 506 mg of crude Example 347D is 146 mg (24%). HPLC R$_f$=3.24 min (YMC S5 ODS column 4.6×50 mm, 10-90% aqueous methanol over 4 minutes containing 0.2% phosphoric acid, 4 mL/min, monitoring at 220 nm) LC/MS: M+H=452.

347E. Preparation of 9-Bromo-2-chloro-11,12-dihydro-6H-5-oxa-12-aza-dibenzo[a,e]cyclooctene

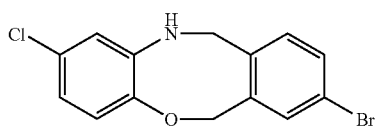

To stirred mixture of 4-Bromo-2-(4-chloro-2-iodo-phenoxymethyl)-benzylamine Example 347D (25.9 mg, 57.2 μmol), NaO-t-Bu (18.1 mg, 0.19 mmol), and BINAP (14.3 mg, 22.9 μmol) in anhydrous toluene (0.4 mL) under argon was added Pd(dba)$_2$ (6.60 mg, 11.4 umol). This reaction mixture in a sealed tube was heated at 95° C. for 75 min, cooled to room temperature and concentrated in vacuo. This was purified by a Shimadzu auto prep HPLC, employing 0% to 100% 10 min gradient elution with 0.1% TFA in MeOH-water solvent system, 220 nM detection, 20 mL/min elution with a YMC ODS S5 20×100 mm column to give 3.8 mg of 9-Bromo-2-chloro-11,12-dihydro-6H-5-oxa-12-aza-dibenzo[a,e]cyclooctene in 20% yield. HPLC R$_f$=3.67 min (YMC S5 ODS column 4.6×50 mm, 10-90% aqueous methanol over 4 minutes containing 0.2% phosphoric acid, 4 mL/min, monitoring at 220 nm) LC/MS: M+H=324.

Example 347

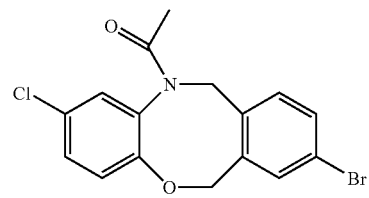

To a stirred solution of 9-Bromo-2-chloro-11,12-dihydro-6H-5-oxa-12-aza-dibenzo[a,e]cyclooctene Example 347E (3.8 mg, 11.7 umol) and DMAP (cat. amount) in toluene (0.3 mL) was added acetic anhydride (0.10 mL, 1.05 mmol) and pyridine (0.05 mL, 46.9 umol). This reaction mixture was heated at 70° C. for 30 minutes, cooled to room temperature and concentrated in vacuo. This was purified by a ISCO auto CombiFlash with a RediSep 4 g column, eluted with Hexane-CH$_2$Cl$_2$, detected at 220 nM to give 4.1 mg of 1-(9-Bromo-2-chloro-6,11-dihydro-5-oxa-12-aza-dibenzo[a,e]cyclooctene-12-yl)-ethanone Example 347E in 96% yield. HPLC R$_f$=3.56 min (YMC S5 ODS column 4.6×50 mm, 10-90% aqueous methanol over 4 minutes containing 0.2% phosphoric acid, 4 mL/min, monitoring at 220 nm) LC/MS: M+H=366.

Example 348

11-Acetyl-11,12-dihydro-2-phenyl-6H-dibenz[b,f][1,5]oxazocine

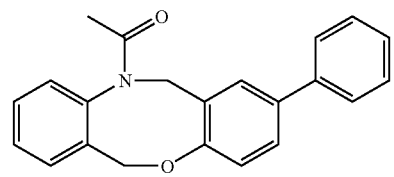

348A. Preparation of 2-(2-Bromo-benzyloxy)-5-chloro-benzonitrile

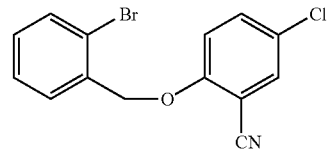

To a stirred mixture of 2-bromo-benzyl bromide (5.00 g, 20.0 mmol) and 2-cyano-4-chloro-phenol (13.2 g, 21.0 mmol) in anhydrous DMF under argon was added 95% NaH (0.56 g, 22.0 mmol) portionwise. This reaction mixture was stirred at room temperature for 1.5 hours and then quenched with water. The resulting mixture was diluted with ether (400 mL), and washed sequentially with water (3×100 mL), 1N NaOH solution (2×30 mL), saturated NaHCO$_3$ solution (1×60 mL) and brine (1×60 mL). The organic layer was dried (MgSO$_4$), filtered and concentrated in vacuo to give 5.30 g of 2-(2-Bromo-benzyloxy)-5-chloro-benzonitrile Example 348A in 82% yield. HPLC R$_t$=3.89 min (YMC S5 ODS column 4.6×50 mm, 10-90% aqueous methanol over 4 minutes containing 0.2% phosphoric acid, 4 mL/min, monitoring at 220 nm) LC/MS: M+H=322

348B. Preparation of 2-(2-Bromo-benzyloxy)-5-chloro-benzylamine

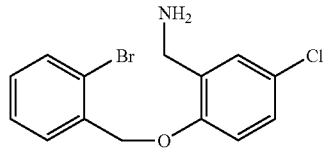

To a stirred solution of 2-(2-Bromo-benzyloxy)-5-chloro-benzonitrile Example 348A (1.52 g, 4.71 mmol) in DCE (50 mL) under argon was added BH$_3$ DMS (30.0 mL, 18.8 mmol). The reaction mixture was heated at 65° C. for 14 h and then cooled to room temperature. The mixture was quenched with 1N HCl solution slowly (25 mL). This solution was then mixed with 1N NaOH solution (30 mL), and extracted with EtOAc (3×80 mL). The combined EtOAc extracts were washed with saturated NaHCO$_3$ solution (1×40 mL) and brine (1×40 mL). The organic layer was dried (MgSO$_4$), filtered and concentrated in vacuo to give 0.92 g (60%) of crude 2-(2-Bromo-benzyloxy)-5-chloro-benzylamine Example 348B which was used as is without further purification. HPLC R$_t$=2.87 min (YMC S5 ODS column 4.6×50 mm, 10-90% aqueous methanol over 4 minutes containing 0.2% phosphoric acid, 4 mL/min, monitoring at 220 nm) LC/MS: M+H=326

348C. Preparation of 2-Chloro-11,12-dihydro-6H-5-oxa-11-aza-dibenzo[a,e]cyclooctene

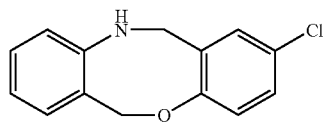

To a stirred mixture of 2-(2-Bromo-benzyloxy)-5-chloro-benzylamine Example 348B (112 mg, 0.34 mmol), BINAP (43.1 mg, 69.3 mmol), and NaO-t-Bu (100 mg, 34.7 mmol) in anhydrous toluene (3.0 mL) under argon was added Pd(dba)$_2$ (20.0 mg, 1.04 mmol). This mixture was heated at 120° C. in a sealed tube for 1 hour and then cooled to room temperature. The mixture was diluted with saturated NaHCO$_3$ solution (40 mL), further saturated with solid NaHCO$_3$, and then extracted with EtOAc (2×60 mL). The combined EtOAc extracts were dried (MgSO$_4$) and concentrated in vacuo. The crude was purified by a ISCO auto CombiFlash with a RediSep 10 g column, eluted with CH$_2$Cl$_2$-EtOAc, detected at 220 nM to give 44 mg of desired 2-Chloro-11,12-dihydro-6H-5-oxa-11-aza-dibenzo[a,e]cyclooctene Example 348C in 51% yield. HPLC R$_t$=2.05 min (YMC S5 ODS column 4.6×50 mm, 10-90% aqueous methanol over 4 minutes containing 0.2% phosphoric acid, 4 mL/min, monitoring at 220 nm) LC/MS: M+H=246

348D

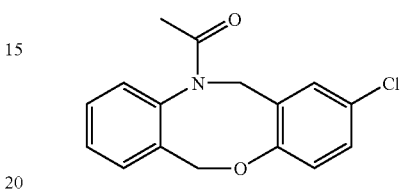

To a stirred solution of 2-Chloro-11,12-dihydro-6H-5-oxa-11-aza-dibenzo[a,e]cyclooctene Example 348C (43 mg, 0.18 mmol) and DMAP (4.27 mg, 34.9 µmol) in toluene (1.25 mL) was added acetic anhydride (36.0 µL, 0.39 mmol) and pyridine (13.9 mg, 0.18 mmol). This reaction mixture was heated at 80° C. for 50 min, cooled to room temperature and concentrated in vacuo. This was purified by a Shimadzu auto prep HPLC, employing 20% to 100% 10 min gradient elution with 0.1% TFA in MeOH-water solvent system, 220 nM detection, 20 mL/min elution with a YMC ODS S5 20×100 mm column to give 27.7 mg of desired 1-(2-Chloro-6H,12H-5-oxa-11-aza-dibenzo[a,e]cycloocten-11-yl)-ethanone Example 348D in 55% yield. HPLC R$_t$=3.09 min (YMC S5 ODS column 4.6×50 mm, 10-90% aqueous methanol over 4 minutes containing 0.2% phosphoric acid, 4 mL/min, monitoring at 220 nm) LC/MS: M+H=288

Example 348

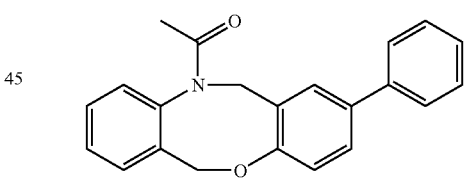

To a stirred mixture of 1-(2-Chloro-6H,12H-5-oxa-11-aza-dibenzo[a,e]cycloocten-11-yl)-ethanone Example 348D (21.5 mg, 74.7 umol), KF (14.3 mg, 0.25 mmol), phenylboranic acid (10.0 mg, 82.2 umol) and tri-t-butyl phosphine (4.54 mg, 22.4 umol) in dioxane (0.40 mL) under argon was added Pd$_2$(dba)$_3$ (6.84 mg, 7.47 umol). This mixture was heated at 80° C. for 19 hours and cooled to room temperature. To this cooled mixture under argon was added more Pd$_2$(dba)$_3$ and tri-t-butyl phosphine. This mixture was then heated at 100° C. for 24 h upon which time some more Pd$_2$(dba)$_3$ and tri-t-butyl phosphine were added. The mixture was heated at 80° C. for another 24 h and cooled to room temperature. This mixture was concentrated in vacuo and purified by a ISCO auto CombiFlash with a RediSep 4 g column, eluted with CH$_2$Cl$_2$-EtOAc, detected at 220 nM to give 4.3 mg of impure 1-(2-Phenyl-6H,12H-5-oxa-11-aza-dibenzo[a,e]cycloocten-11-yl)-ethanone Example 348. This was further purified by a Shimadzu auto prep HPLC, employing 30% to 100% 10 min gradient elution with 0.1% TFA in MeOH-water solvent system, 220 nM detection, 20 mL/min elution with a YMC ODS S5 20×100 mm column to give 3.3 mg of 1-(2-Phenyl-6H,12H-5-oxa-11-aza-dibenzo[a,e]cycloocten-11-yl)-ethanone Example 348 in 13% yield. HPLC $R_f$=3.53 min (YMC S5 ODS column 4.6×50 mm, 10-90% aqueous methanol over 4 minutes containing 0.2% phosphoric acid, 4 mL/min, monitoring at 220 nm) LC/MS: M+H=330

Example 349

12-Acetyl-3-chloro-11,12-dihydro-8-phenyl-,5,5-dioxide6H-dibenzo[b,f][1,4]thiazocine

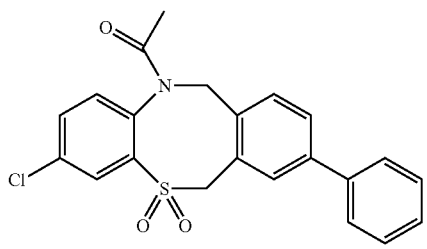

Example 349A

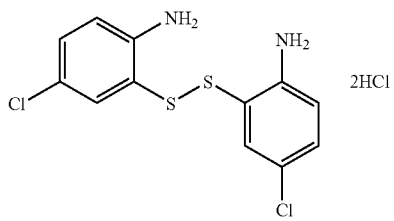

To a solution of KOH (35 g, 625 mmol) in water (50 ML) was added 2-amino-6-chlorobenzothiazole (5 g, 27.2 mmol) and the suspension was refluxed overnight under argon. The mixture was then cooled to 0° C. and neutralized to pH 6 with concentrated HCl. The resulting solid was filtered and dried in vacuo to afford Example 349A (4.0 g, 93%).

Example 349B

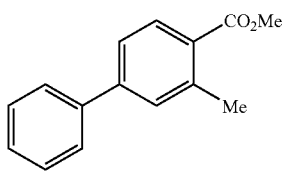

A solution of 4-Bromo-2-methyl-benzoic acid methyl ester (5.2 g, 22.7 mmol) and Pd(PPh$_3$)$_4$ (1.3 g, 1.1 mmol) in toluene (45 mL) was treated with a solution of phenyl boronic acid (4.1 g, 122 mmol) in EtOH (135 mL) and saturated aqueous NaHCO$_3$ (22.5 mL). The resulting solution was heated to reflux for 2.5 hours, cooled to room temperature and diluted with saturated aqueous NaCl. The mixture was extracted with EtOAc, dried (Na$_2$SO$_4$), filtered and concentrated. The crude mixture was purified by flash chromatography (SiO$_2$, 5% EtOAc/Hexanes) to afford Example 349B (3.4 g, 67%).

Example 349C

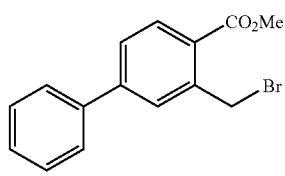

A solution Example 349B (3.4 g, 15 mmol) and benzoylperoxide (0.36 g, 1.5 mmol) in CCl$_4$ (300 mL) was treated with N-bromosuccinimide (2.46 g, 13.8 mmol) and heated to reflux for 16 hours. The reaction mixture was cooled to room temperature and filtered. The filtrate was concentrated and slurried in MeOH, filtered and dried in vacuo to provide Example 349C (2.3 g, 50%).

Example 349D

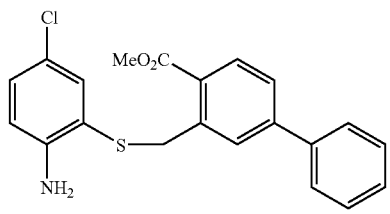

A mixture of Example 349A (234 mg, 0.6 mmol) and dithiothreitol (140 mg, 0.9 mmol) in DMF was stirred at room temperature under argon for 2.5 hours. This mixture was then treated with Example 349C (550 mg, 1.8 mmol) and diisopropylethylamine (1.05 mL, 6 mmol) and stirring was continued at room temperature for an additional two hours. The resulting mixture was partitioned between saturated aqueous NaHCO$_3$ (25 mL) and EtOAc (75 mL). The organic phase was separated and washed with brine (20 mL), dried (Na$_2$SO$_4$), filtered and concentrated. The crude mixture was purified by flash chromatography (SiO$_2$, 8:1 to 4:1 to 2:1 Heptane/EtOAc) to afford Example 349D (390 mg, 85%).

Example 349E

A clear solution of Example 349D (310 mg, 0.81 mmol) in THF (25 mL) was treated with LiAlH₄ (40 mg, 1 mmol) and warmed to 50° C. for 30 minutes. The reaction was quenched with the addition of acetone and the mixture was concentrated. The residue was taken up in EtOAc (100 mL) and saturated aqueous NaHCO₃ (20 mL), stirred for 30 minutes and the layers were separated. The organic layer was dried (Na₂SO₄), filtered through a pad of SiO₂ and concentrated. The crude alcohol was dissolved in acetonitrile (200 mL) and Ph₃PBr₂ (633 mg, 1.5 mmol) was added. The reaction was stirred at room temperature for 15 minutes then imidazole (100 mg, 1.5 mmol) was added. The mixture was heated to 55° C. for eight hours. Additional Ph₃PBr₂ (1 equiv.) and imidazole were added and heating was continued. After two additional hours, more Ph₃PBr₂ (1 equiv.) and imidazole were added and the reaction temperature was increased to 80° C. for two hours. The reaction mixture was concentrated and the residue was partitioned between saturated aqueous NaHCO₃ and EtOAc. The organic layer was separated and dried (Na₂SO₄), filtered and concentrated. The crude product was purified by flash chromatography (SiO₂, 10:1 to 0:1 Heptane/EtOAc) to afford the title compound (140 mg, 81%).

Example 349F

12-Acetyl-3-chloro-11,12-dihydro-8-phenyl-6H-dibenzo[b,f][1,4]thiazocine

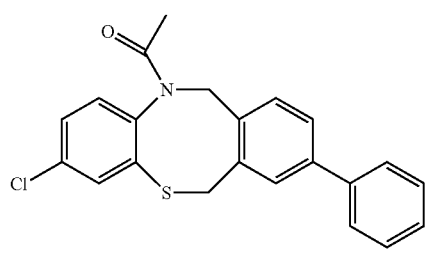

A solution of Example 349E (140 mg, 0.41 mmol) was dissolved in CH₂Cl₂ (10 mL) and Et₃N (0.15 mL) and acetyl chloride (0.05 mL) were added. The reaction mixture was stirred at room temperature for 20 minutes and additional Et₃N and acetyl chloride was added. The reaction was stirred for an additional 30 minutes and saturated aqueous NaHCO₃ (3 mL) was added. The organic layer was separated and dried (Na₂SO₄) and filtered through a pad of silica eluting with EtOAc. The filtrate was concentrated and purified by flash chromatography (SiO₂, 10% toluene/CH₂Cl₂ then 5% toluene/CH₂Cl₂ then 2% EtOAc/CH₂Cl₂ then 4% toluene/4% bEtOAc/CH₂Cl₂ to give the desired product (95 mg, 61%). HPLC $R_t$=4.65 min. m/z=380 (M+H⁺)

Example 349G

12-Acetyl-3-chloro-11,12-dihydro-8-phenyl-,5-oxide6H-dibenzo[b,f][1,4]thiazocine

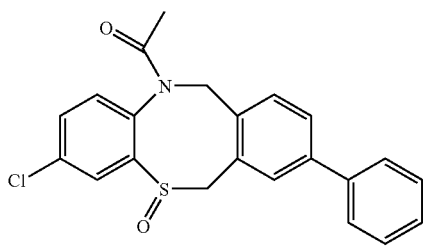

A clear solution of Example 349F (16 mg, 0.042 mmol) in CH₂Cl₂ (15 mL) was treated with mCPBA (14 mg, 0.049 mmol) at 0° C. After stirring at this temperature for 2 hours, saturated aqueous NaHCO₃ was added. The organic layer was separated and dried (Na₂SO₄), filtered and concentrated. Flash chromatography (SiO₂, 1:1 then 0:1 Heptane/EtOAc) afforded the desired compound (7 mg, 42%). HPLC $R_t$=3.88 min. m/z=396 (M+H⁺)

Example 349

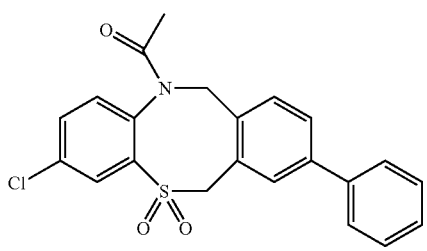

A solution of Example 349G in CH₂Cl₂ was treated with mCPBA and stirred at room temperature for seven hours. The mixture was then treated with 2M NaOH and the organic layer was separated, dried (Na₂SO₄), filtered through a pad of silica and concentrated. The resulting solid was crystallized from EtOH/H₂O to afford a white solid contaminated with benzoic acid. The solid was dissolved in hot DMSO/EtOH and precipitated with water to afford the title compound (0.84 mg). HPLC $R_t$=4.03 min. m/z=412 (M+H⁺).

Examples 350 to 355

The compounds listed in Table 33 were prepared in a manner analogous to that described for Example 349 starting with the appropriate materials.

TABLE 33

| Example No. | $R_7$ | $R_8$ | $R_{10}$ | $R_{11}$ | Compound name | [M + H] | HPLC Ret Time (min) |
|---|---|---|---|---|---|---|---|
| 350 | Me | Me | H | H | 12-Acetyl-11,12-dihydro-2,3-dimethyl-6H-dibenzo[b,f][1,4]thiazocine | 298 | 2.30(b) |
| 351 | H | Cl | F | H | 12-Acetyl-2-chloro-9-fluoro-11,12-dihydro-6H-dibenzo[b,f][1,4]thiazocine | 322 | 1.80(b) |
| 352 | H | Cl | H | Cl | 12-Acetyl-2,7-dichloro-11,12-dihydro-6H-dibenzo[b,f][1,4]thiazocine | 338 | 3.97 |
| 353 | H | Cl | H | Br | 12-Acetyl-8-bromo-2-chloro-11,12-dihydro-6H-dibenzo[b,f][1,4]thiazocine | 382 | 4.03 |
| 354 | H | Cl | H | Ph | 12-Acetyl-8-bromo-2-chloro-11,12-dihydro-6H-dibenzo[b,f][1,4]thiazocine | 380 | 4.25 |
| 355 | Cl | Cl | H | H | 12-Acetyl-2,3-dichloro-11,12-dihydro-6H-dibenzo[b,f][1,4]thiazocine | 338 | 4.03 |

What is claimed is:

1. A compound of formula I:

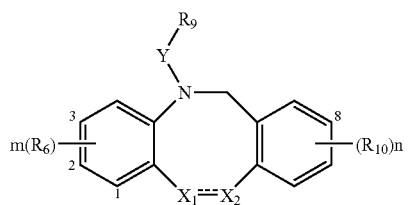

or an enantiomer, diastereomer, tautomer, or pharmaceutically acceptable salt thereof, wherein the symbols have the following meanings and are, for each occurrence, independently selected:

Y is —C(=O)— or —S(=O)$_2$—;

$X_1$=$X_2$ is —$CR_1$=$CR_3$—, —$CR_1R_2$—$CR_3R_4$—, —C(=O)—$CR_3R_4$—, or —$CR_1R_2$—C(=O)—;

$R_2$, $R_4$, $R_6$ and $R_{10}$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, S(=O)$R_e$, S(=O)$_2R_e$, S(=O)$_2OR_e$, $NR_bR_c$, $NR_bS$(=O)$_2R_e$, S(=O)$_2NR_bR_c$, C(=O)$OR_e$, C(=O)$R_a$, C(=O)$NR_bR_c$, OC(=O)$R_a$, OC(=O)$NR_bR_c$, $NR_bC$(=O)$OR_e$, $NR_aC$(=O)$NR_bR_c$, $NR_aS$(=O)$_2NR_bR_c$, or $NR_bC$(=O)$R_a$, wherein: $R_2$ and $R_4$ together may optionally form a 3-7 membered optionally substituted carbocyclic ring or 3-7 membered optionally substituted heterocyclic ring;

$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, S(=O)$R_e$, S(=O)$_2R_e$, C(=O)$OR_e$, C(=O)$R_a$, $NR_bR_c$, $NR_bC$(=O)$R_a$, $NR_bC$(=O)$OR_e$, C(=O)$NR_bR_c$, OC(=O)$R_a$, or OC(=O)$NR_bR_c$, wherein $R_1$ and $R_3$ together may optionally form a 3-7 membered optionally substituted carbocyclic ring or 3-7 membered optionally substituted heterocyclic ring;

$R_9$ is H, alkyl or substituted alkyl, cycloalkyl or substituted cycloalkyl, cycloalkenyl or substituted cycloalkenyl, heterocycle or substituted heterocycle, aryl or substituted aryl, $OR_e$, or $NR_bR_c$;

m is 1-4; and n is 1-4;

provided that:

at least one of $R_6$ and $R_{10}$ is not H; and when $X_1$=$X_2$ is —$CH_2$—$CH_2$—, $R_9$ is not H, aryl or substituted aryl, or heteroaryl or substituted heteroaryl.

2. The compound of claim 1, wherein:

$R_2$, $R_4$, $R_6$ and $R_{10}$ are each independently hydrogen, halogen, cyano, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, S(=O)$R_e$, S(=O)$_2R_e$, S(=O)$_2OR_e$, $NR_bR_c$, $NR_bS$(=O)$_2R_e$, S(=O)$_2NR_bR_c$, C(=O)$OR_e$, C(=O)$R_a$, C(=O)$NR_b$ $R_c$, OC(=O)$R_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$,
  wherein: $R_2$ and $R_4$ together may optionally form a 3-7 membered carbocyclic ring or 3-7 membered heterocyclic ring;
$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein $R_1$ and $R_3$ together may optionally form a 3-7 membered optionally substituted carbocyclic ring or 3-7 membered optionally substituted heterocyclic ring; and
$R_9$ is H, alkyl or substituted alkyl, cycloalkyl or substituted cycloalkyl, or NR$_b$R$_c$.

3. The compound of claim 1, wherein:
$R_6$ and $R_{10}$ are each independently hydrogen, halogen, cyano, nitro, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$;
$R_2$ and $R_4$ are each independently hydrogen, cyano, nitor, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein $R_2$ and $R_4$ together may optionally form a 3-6 membered optionally substituted carbocyclic ring or 3-6 membered optionally substituted heterocyclic ring;
$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein $R_1$ and $R_3$ together may optionally form a 3-6 membered optionally substituted carbocyclic ring or 3-6 membered optionally substituted heterocyclic ring; and
$R_9$ is H, $C_1$-$C_4$ alkyl or substituted $C_1$-$C_4$ alkyl, cycloalkyl or substituted cycloalkyl, or NR$_b$R$_c$.

4. The compound of claim 1 having the following structure Ia,

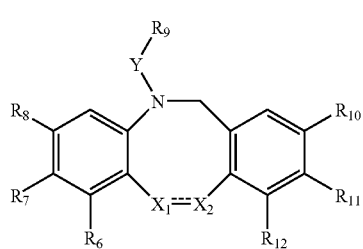

(Ia)

wherein:
$X_1$=$X_2$ is —CR$_1$=CR$_3$—, —CR$_1$R$_2$—CR$_3$R$_4$—, or —C(=O)—CR$_3$R$_4$—;
$R_6$, $R_7$, $R_8$, $R_{10}$, $R_{11}$, and $R_{12}$ are each independently hydrogen, halogen, cyano, nitor, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_a$ is hydrogen, alkyl or substituted alkyl, alkenyl or substituted alkenyl, alkynyl or substituted alkynyl, cycloalkyl or substituted cycloalkyl, heterocycle or substituted heterocycle, aryl or substituted aryl;
$R_2$ and $R_4$ are each independently hydrogen, cyano, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein $R_2$ and $R_4$ together may optionally form a 3-6 membered optionally substituted carbocyclic ring or 3-6 membered optionally substituted heterocyclic ring;
$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein $R_1$ and $R_3$ together may optionally form a 3-6 membered optionally substituted carbocyclic ring or 3-6 membered optionally substituted heterocyclic ring; and
$R_9$ is H, $C_1$-$C_4$ alkyl or substituted $C_1$-$C_4$ alkyl, cycloalkyl or substituted cycloalkyl, or NR$_b$R$_c$.

5. The compound of claim 1 having the following structure Ib,

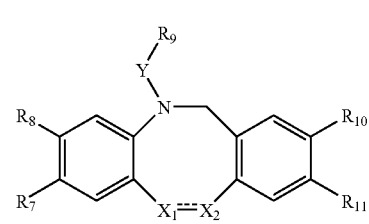

(Ib)

wherein:
$X_1$=$X_2$ is —CR$_1$=CR$_3$—, —CR$_1$R$_2$—CR$_3$R$_4$—, or —C(=O)—CR$_3$R$_4$—;
$R_7$, $R_8$, $R_{10}$ and $R_{11}$ are each independently hydrogen, halogen, cyano, nitro, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$;
$R_2$ and $R_4$ are each independently hydrogen, cyano, nitro, alkyl or substituted alkyl, cycloalkyl or substituted cycloalkyl, heterocycle or substituted heterocycle, aryl or substituted aryl, $OR_a$, $SR_a$, $S(=O)R_e$, $S(=O)_2R_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, or $NR_bC(=O)R_a$, wherein $R_2$ and $R_4$ together may optionally form a 3-6 membered optionally substituted carbocyclic ring or 3-6 membered optionally substituted heterocyclic ring;

$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $C(=O)NR_bR_c$, $OC(=O)R_a$, or $OC(=O)NR_bR_c$, wherein $R_1$ and $R_3$ together may optionally form a 3-6 membered optionally substituted carbocyclic ring or 3-6 membered optionally substituted heterocyclic ring; and $R_9$ is H, alkyl or substituted alkyl, cycloalkyl or substituted cycloalkyl, heterocycle or substituted heterocycle, aryl or substituted aryl, or $NR_bR_c$;

provided that:

at least one of $R_7$, $R_8$, $R_{10}$ and $R_{11}$ is not H.

6. The compound of claim 5, wherein $R_9$ is H, methyl, trifluoromethyl, ethyl, isopropyl, cyclopropyl, or $NH_2$, or

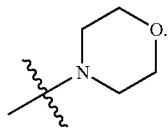

7. The compound of claim 6, wherein $R_7$ and $R_8$ are each independently hydrogen, halogen, cyano, nitro, SMe, $S(=O)_2$ Me, or OMe, and wherein at least one of $R_7$ and $R_8$ is not hydrogen.

8. The compound of claim 7, wherein Y is —C(=O)—.

9. The compound of claim 8, wherein $X_1=X_2$ is —CH=CH—, —$CH_2$—$CH_2$—, or

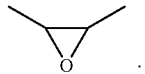

10. The compound of claim 9, wherein $R_9$ is methyl; $R_{10}$ and $R_{11}$ are each independently hydrogen, halogen, trifluoromethyl, trifluoromethoxy, cyano, alkyl or substituted alkyl, cycloalkyl or substituted cycloalkyl, heterocycle or substituted heterocycle, aryl or substituted aryl, $OR_a$, $SR_a$, $S(=O)R_c$, $S(=O)_2R_e$, $NR_bR_c$, $NR_bS(=O)_2R_e$, $C(=O)OR_e$, $C(=O)R_e$, $C(=O)NR_bR_c$, $OC(=O)R_a$, $NR_bC(=O)OR_e$, or $NR_bC(=O)R_a$.

11. A pharmaceutical composition comprising at least one compound according to claim 1 and a pharmaceutically-acceptable carrier or diluent.

12. A method for treating a condition or disorder comprising administering to a mammalian species in need thereof a therapeutically effective amount of at least one compound according to claim 1, wherein said condition or disorder is selected from the group consisting of benign prostate hypertrophia, benign prostatic hyperplasia, adenomas and neoplasies of the prostate, prostate cancer, hirsutism, and polycystic ovary syndrome.

13. The method of claim 12, wherein said condition or disorder is prostate cancer.

* * * * *

UNITED STATES PATENT AND TRADEMARK OFFICE
CERTIFICATE OF CORRECTION

PATENT NO.         : 7,417,040 B2
APPLICATION NO.  : 11/066373
DATED              : August 26, 2008
INVENTOR(S)       : Fink et al.

Page 1 of 1

It is certified that error appears in the above-identified patent and that said Letters Patent is hereby corrected as shown below:

In Column 203, Line 29,
"$R_2$ and $R_4$ are each independently hydrogen, cyano, nitor," should read:
-- $R_2$ and $R_4$ are each independently hydrogen, cyano, nitro, --

In Column 204, Line 5,
"hydrogen, halogen, cyano, nitor, alkyl or substituted" should read:
-- hydrogen, halogen, cyano, nitro, alkyl or substituted --

In Column 206, Line 3,
"$S(=O)_2$ Me, or OMe, and wherein at least one of $R_7$ and $R_8$" should read:
-- $S(=O)_2$Me, or OMe, and wherein at least one of $R_7$ and $R_8$ --

Signed and Sealed this

Twenty-fourth Day of March, 2009

JOHN DOLL
*Acting Director of the United States Patent and Trademark Office*